(12) United States Patent
Alcouffe et al.

(10) Patent No.: US 8,859,544 B2
(45) Date of Patent: Oct. 14, 2014

(54) INDOLIZINE DERIVATIVES, PROCESS FOR THE PREPARATION THEREOF AND THERAPEUTIC USE THEREOF

(75) Inventors: Chantal Alcouffe, Paris (FR); Corentin Herbert, Paris (FR); Gilbert Lassalle, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/808,483

(22) PCT Filed: Jul. 4, 2011

(86) PCT No.: PCT/IB2011/052953
§ 371 (c)(1),
(2), (4) Date: Jan. 4, 2013

(87) PCT Pub. No.: WO2012/004731
PCT Pub. Date: Jan. 12, 2012

(65) Prior Publication Data
US 2013/0116249 A1 May 9, 2013

(30) Foreign Application Priority Data

Jul. 6, 2010 (FR) ..................................... 10 55477

(51) Int. Cl.
| C07D 471/04 | (2006.01) |
| A61K 45/06 | (2006.01) |
| A61K 31/5377 | (2006.01) |
| A61K 31/517 | (2006.01) |
| A61K 31/4709 | (2006.01) |
| A61K 9/20 | (2006.01) |
| C07D 207/32 | (2006.01) |
| C07D 207/36 | (2006.01) |
| C07D 211/82 | (2006.01) |

(52) U.S. Cl.
CPC .......... *C07D 471/04* (2013.01); *A61K 31/5377* (2013.01); *A61K 31/517* (2013.01); *A61K 45/06* (2013.01); *A61K 9/2054* (2013.01); *C07D 207/32* (2013.01); *A61K 31/4709* (2013.01); *A61K 9/2059* (2013.01); *A61K 9/2018* (2013.01); *C07D 207/36* (2013.01); *C07D 211/82* (2013.01)
USPC ................... 514/233.2; 514/266.21; 514/312; 544/128; 544/284; 546/153; 546/165

(58) Field of Classification Search
None
See application file for complete search history.

(56) References Cited

U.S. PATENT DOCUMENTS

2006/0199962 A1 9/2006 Alcouffe et al.
2009/0030034 A1 1/2009 Badorc et al.

FOREIGN PATENT DOCUMENTS

| WO | WO 03/084956 A1 | 10/2003 |
| WO | WO 03/084959 A1 | 10/2003 |
| WO | WO 2004/054507 A2 | 7/2004 |
| WO | WO 2005/028476 A1 | 3/2005 |
| WO | WO 2005/028479 A2 | 3/2005 |
| WO | WO 2006/097625 A1 | 9/2006 |
| WO | WO 2007/060318 A1 | 5/2007 |
| WO | WO 2007/080325 A1 | 7/2007 |
| WO | WO 2008/012690 A2 | 1/2008 |

OTHER PUBLICATIONS

Wesche et al., 437 Biochem. J. 199-213 (2011).*
Schultz et al., 19 J. Clinical Invest. 709-719 (1989).*

(Continued)

*Primary Examiner* — Janet L Andres
*Assistant Examiner* — Timothy R Rozof
(74) *Attorney, Agent, or Firm* — Scully, Scott, Murphy & Presser P.C.

(57) ABSTRACT

The invention relates to compounds corresponding to formula (I):

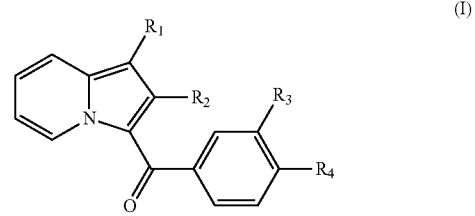

(I)

in which
$R_3$ and $R_4$ together form, with the carbon atoms of the phenyl nucleus to which they are attached, a 6-membered nitrogenous heterocycle corresponding to one of formula (A), (B) or (C) below:

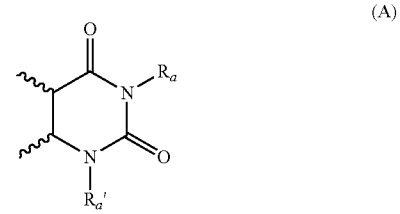

(A)

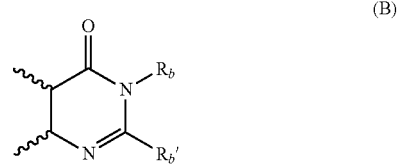

(B)

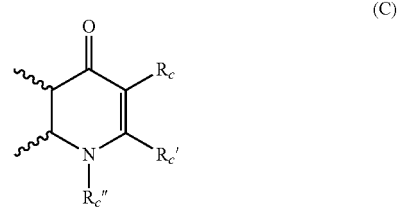

(C)

in which the wavy lines represent the phenyl nucleus to which $R_3$ and $R_4$ are attached.
Preparation process and therapeutic use.

24 Claims, No Drawings

(56) References Cited

OTHER PUBLICATIONS

International Search Report, dated Sep. 16, 2011, issued in PCT/IB2011/052953.

Costa Rican Office Action dated May 7, 2013 directed to Costa Rican Patent Application No. 2013-0001.

Ecuadorian Notice of Opposition dated Feb. 12, 2014 received from related Application No. SP-2013-12362.

* cited by examiner

INDOLIZINE DERIVATIVES, PROCESS FOR THE PREPARATION THEREOF AND THERAPEUTIC USE THEREOF

The present invention relates to indolizine derivatives which are inhibitors of FGFs (Fibroblast Growth Factors), to the process for the preparation thereof and to the therapeutic use thereof.

FGFs are a family of polypeptides synthesized by a large number of cells during embryonic development and by cells of adult tissues in various pathological conditions.

Indolizine derivatives, which are antagonists of the binding of FGFs to their receptors, are described in international patent applications WO 03/084956 and WO 2005/028476, while imidazo[1,5-a]pyridine derivatives which are FGF antagonists are described in international patent application WO 2006/097625. Novel indolizine derivatives, which are antagonists of the binding of FGFs to their receptors, have now been identified.

The subject of the present invention is thus compounds, indolizine derivatives, corresponding to formula (I):

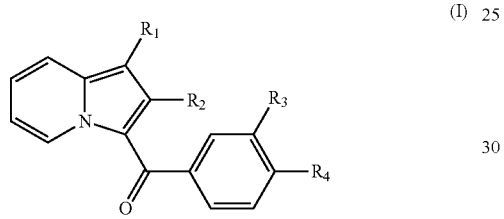

(I)

in which:
$R_1$ represents
  a hydrogen or halogen atom,
  an alkyl group optionally substituted with —$COOR_5$,
  an alkenyl group optionally substituted with —$COOR_5$,
  a —$COOR_5$ or —$CONR_5R_6$ group,
  an —$NR_5COR_6$ or —$NR_5$—$SO_2R_6$ group,
  an —$OR_5$, —O-Alk-$OR_5$, —O-Alk-$COOR_5$, —O-Alk-$OR_5$, —O-Alk-$NR_5R_5$, —O-Alk-$NR_7R_5$ group,
  or
  an aryl group, in particular phenyl, or a heteroaryl group, said aryl or heteroaryl group being optionally substituted with one or more groups selected from: halogen atoms, alkyl groups, cycloalkyl groups, —$COOR_5$, —$CF_3$, —$OCF_3$, —CN, —$C(NH_2)NOH$, —$OR_5$, —O-Alk-$COOR_5$, —O-Alk-$NR_5R_6$, —O-Alk-$NR_7R_6$, -Alk-$OR_5$, -Alk-$COOR_5$, —$CONR_5R_6$, —CO—$NR_5$—$OR_6$, —CO—$NR_5$—$SO_2R_7$, —$CONR_5$-Alk-$NR_5R_6$, —$CONR_5$-Alk-$NR_7R_6$, -Alk-$NR_5R_6$, —$NR_5R_6$, —$NC(O)N(CH_3)_2$, —CO-Alk, —$CO(OAlk)_6OH$, $COO$-Alk-$NR_5R_6$, $COO$-Alk-$NR_7R_8$ and 5-membered heteroaryl groups, said heteroaryl groups being optionally substituted with one or more groups selected from halogen atoms and alkyl, —$CF_3$, —CN, —$COOR_5$, -Alk-$OR_5$, -Alk-$COOR_5$, —$CONR_5R_6$, —$CONR_7R_8$, —CO—$NR_5$—$OR_6$, —CO—$NR_5$—$SO_2R_6$, —$NR_5R_6$ and -Alk-$NR_5R_6$ groups, or with a hydroxyl group or with an oxygen atom,
n is an integer ranging from 1 to 3,
$R_2$ represents:
  a hydrogen atom,
  an alkyl group,
  a phenyl group optionally substituted with one or more alkyl groups,
$R_3$ and $R_4$ together form, with the carbon atoms of the phenyl nucleus to which they are attached, a 6-membered nitrogenous heterocycle corresponding to one of formula (A), (B) or (C) below:

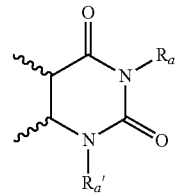

(A)

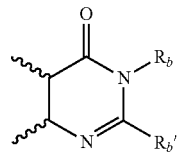

(B)

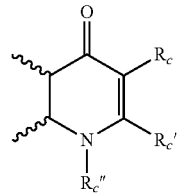

(C)

in which the wavy lines represent the phenyl nucleus to which $R_3$ and $R_4$ are attached and:
$R_a$ represents a hydrogen atom or an alkyl, haloalkyl, -Alk-$CF_3$, -Alk-$COOR_5$, -Alk'-$COOR_5$, -Alk-$CONR_5R_6$, -Alk'-$CONR_5R_6$, -Alk-$CONR_7R_3$, -Alk-$NR_5R_6$, -AlkCONR_5—$OR_6$, -Alk-$NR_7R_8$, -Alk-cycloalkyl, -Alk-O—$R_5$, -Alk-S—$R_5$, -Alk-CN, —$OR_5$, —OAlkCOOR_5, —$NR_5R_6$, —$NR_5$—$COOR_6$, -Alk-aryl, -Alk-O-aryl, -Alk-O-heteroaryl, -Alk-heteroaryl or heteroaryl group, where the aryl or heteroaryl group is optionally substituted with one or more halogen atoms and/or alkyl, cycloalkyl, —$CF_3$, —$OCF_3$, —O—$R_5$ or —S—$R_5$ groups,
$R_{a'}$ represents a hydrogen atom or a linear, branched, cyclic or partially cyclic alkyl group, or an -Alk-$OR_5$, -Alk-$NR_5R_6$ or -Alk-$NR_7R_8$ group, $R_{a'}$ being optionally substituted with one or more halogen atoms,
$R_b$ represents a hydrogen atom or an alkyl or -Alk-$COOR_5$ group,
$R_{b'}$ represents a hydrogen atom or an alkyl, haloalkyl, cycloalkyl, phenyl or -Alk-$COOR_5$ group,
$R_c$ represents a hydrogen atom or an alkyl, —CN, —$COOR_5$, —CO—$NR_5R_6$, —$CONR_7R_5$—CO—$NR_5$-Alk-$NR_5R_6$, —$CONR_5$-Alk-$OR_5$, —$CONR_5SO_2R_5$, -Alk-aryl or -Alk-heteroaryl group, where the aryl or heteroaryl group is optionally substituted with one or more halogen atoms and/or alkyl, cycloalkyl, —$CF_3$, —$OCF_3$, —O-alkyl or —S-alkyl groups,
$R_{c'}$ represents a hydrogen atom or an alkyl group,
$R_{c''}$ represents a hydrogen atom or an alkyl, alkenyl, haloalkyl, cycloalkyl, -Alk-$NR_5R_6$, -Alk-$NR_7R_8$, -Alk-$OR_5$ or -Alk-$SR_5$ group, $R_5$ and $R_6$, which may be identical or different, represent hydrogen atoms, haloalkyl groups or alkyl groups, cycloalkyl groups or an Ms (mesyl) group, $R_7$ and $R_8$, which may be identical or different, represent hydrogen atoms or alkyl or phenyl groups, or else $R_7$ and $R_8$ together form a 3- to 8-membered saturated ring which can optionally contain a heteroatom, Alk represents a linear or branched alkylene chain, and Alk' represents a linear, branched, cyclic or partially cyclic alkylene chain, these compounds being optionally in the form of a pharmaceutically acceptable salt thereof.

The compounds of formula (I) may comprise one or more asymmetric carbon atoms. They can therefore exist in the form of enantiomers or of diastereoisomers. These enantiomers and diastereoisomers, and also mixtures thereof, including racemic mixtures, are part of the invention.

The compounds of formula (I) can exist in the form of bases or of acids or can be salified with acids or bases, in particular pharmaceutically acceptable acids or bases. Such addition salts are part of the invention. These salts are advantageously prepared with pharmaceutically acceptable acids or bases, but the salts of other acids or bases that are of use, for example, for purifying or isolating the compounds of formula (I) are also part of the invention.

The compounds of formula (I) can also exist in the form of hydrates or of solvates, namely in the form of associations or combinations with one or more molecules of water or with a solvent. Such hydrates or solvates are also part of the invention.

In the context of the invention, and unless otherwise mentioned in the text, the term:

"alkyl" is intended to mean: a linear or branched, saturated hydrocarbon-based aliphatic group containing from 1 to 6 carbon atoms;

"cycloalkyl" is intended to mean: a cyclic alkyl group comprising from 3 to 8 ring members, containing between 3 and 6 carbon atoms and optionally comprising one or more heteroatoms, for example 1 or 2 heteroatoms, such as nitrogen and/or oxygen, said cycloalkyl group being optionally substituted with one or more halogen atoms and/or alkyl groups. By way of examples, mention may be made of cyclopropyl, cyclopentyl, piperazinyl, pyrrolidinyl and piperidinyl groups;

"partially cyclic alkyl group" is intended to mean: an alkyl group of which only a part forms a ring;

"alkylene" is intended to mean: a linear or branched divalent alkyl group containing from 1 to 6 carbon atoms;

"halogen" is intended to mean: a chlorine, fluorine, bromine or iodine atom, preferably a chlorine or fluorine atom;

"haloalkyl" is intended to mean: an alkyl chain in which all or some of the hydrogen atoms are replaced with halogen atoms, such as fluorine atoms;

"alkenyl" is intended to mean: an alkyl group comprising an ethylenic unsaturation; and "aryl" is intended to mean: a cyclic aromatic group containing between 5 and 10 carbon atoms, for example a phenyl group;

"heteroaryl" is intended to mean: a cyclic aromatic group containing between 3 and 10 atoms, including one or more heteroatoms, for example between 1 and 4 heteroatoms, such as nitrogen, oxygen or sulphur, this group comprising one or more, preferably one or two, rings. The heterocycles may comprise several condensed rings.

The heteroaryls are optionally substituted with one or more alkyl groups or an oxygen atom. By way of examples, mention may be made of thienyl, pyridinyl, pyrazolyl, imidazolyl, thiazolyl and triazolyl groups;

"5-membered heteroaryl" is intended to mean: a heteroaryl group consisting of a 5-membered ring comprising 1 to 4 heteroatoms (such as oxygen and/or nitrogen atoms), optionally substituted with one or more alkyl groups or a hydroxyl group or with an oxygen atom. Mention may, for example, be made of oxadiazolyl and tetrazolyl groups.

Among the compounds of formula (I) according to the invention, mention may be made of a subgroup of compounds in which $R_1$ represents an —$OR_5$, —O-Alk-$OR_5$, —$COOR_5$ or —O-Alk-$COOR_5$ group or a phenyl group optionally substituted with one or more alkyl or —$COOR_5$ groups, in which $R_5$ represents a hydrogen atom or an alkyl group containing from 1 to 4 carbon atoms, and Alk represents an alkylene chain containing 1 or 2 carbon atoms, or a heteroaryl group, preferably a pyridinyl group.

Another subgroup of compounds of formula (I) according to the invention is such that $R_1$ represents an —$OR_5$, —O-Alk-$OR_5$ or —O-Alk-$COOR_5$ group or a phenyl group optionally substituted with one or more alkyl or —$COOR_5$ groups, in which $R_5$ represents a hydrogen atom or a methyl group, and Alk represents an alkylene chain containing 1 or 2 carbon atoms, or a heteroaryl group, preferably a pyridinyl group.

Advantageously, $R_1$ represents an —$OR_5$, —O-Alk-$OR_5$ or —O-Alk-$COOR_5$ group or a phenyl group optionally substituted with a —$COOR_5$ group, in which $R_5$ represents a hydrogen atom or a methyl group, and Alk represents an alkylene chain containing 2 carbon atoms.

Among the compounds of formula (I) according to the invention, mention may be made of another subgroup of compounds in which $R_2$ represents an alkyl group containing from 1 to 4 carbon atoms or a phenyl group.

Advantageously, $R_2$ represents a methyl or phenyl group.

Among the compounds of formula (I) according to the invention, mention may be made of another subgroup of compounds in which $R_3$ and $R_4$ together form, with the carbon atoms of the phenyl nucleus to which they are attached, a 6-membered nitrogenous heterocycle corresponding to one of formula (A), (B) or (C) defined above and in which:

$R_a$ represents a hydrogen atom or an alkyl or haloalkyl, —$OR_5$, -Alk-$OR_5$, -Alk'-$COOR_5$, —$NR_5R_6$, -Alk-$NR_7R_a$, -Alk-CN, —$NR_5$—$COOR_6$, -Alk'-CO—$NR_5R_6$, -Alk-CO—$NR_5$—$OR_6$ or —O-Alk-$COOR_5$ group, or a heteroaryl, -Alk-heteroaryl or -Alk-aryl group in which the aryl or heteroaryl group is optionally substituted with an alkyl group or a halogen atom, $R_{a'}$ represents a hydrogen atom or an alkyl or -Alk-$OR_5$ group, $R_b$ represents a hydrogen atom or an alkyl or -Alk-$COOR_5$ group, $R_{b'}$ represents a hydrogen atom or an alkyl, haloalkyl or -Alk-$COOR_5$ group, $R_c$ represents a hydrogen atom or an alkyl, —$COOR_5$, CN, —CO—$NR_5R_6$, —CO—$NR_7R_5$, Alk-heteroaryl or heteroaryl group, $R_{c'}$ represents a hydrogen atom or an alkyl group, $R_{c''}$ represents a hydrogen atom or an alkyl or alkenyl group, said alkyl or alkenyl groups mentioned above containing from 1 to 4 carbon atoms, $R_5$ and $R_6$ represent hydrogen atoms or alkyl or haloalkyl groups, said alkyl and haloalkyl groups containing from 1 to 4 carbon atoms, $R_7$ and $R_8$ represent hydrogen atoms or alkyl groups containing from 1 to 4 carbon atoms, or together form a 5- or 6-membered saturated ring, Alk represents a linear or branched alkylene chain containing from 1 to 4 carbon atoms, and Alk' represents a linear, branched, cyclic or partially cyclic alkylene chain containing from 1 to 4 carbon atoms.

Among the compounds of formula (I), mention may also be made of the compounds of the subgroup defined above in which $R_3$ and $R_4$ together form, with the carbon atoms of the phenyl nucleus to which they are attached, a 6-membered nitrogenous heterocycle corresponding to either of formulae (A) and (C).

Another subgroup corresponds to the compounds of formula (I) in which $R_3$ and $R_4$ together form, with the carbon atoms of the phenyl nucleus to which they are attached, a nitrogenous heterocycle of formula (C) in which:

$R_c$ represents a hydrogen atom or an alkyl, —COOR$_5$, CN, —CO—NR$_5$R$_6$, —CO—NR$_7$R$_5$, Alk-heteroaryl or heteroaryl group, $R_{c'}$ represents a hydrogen atom or an alkyl group, $R_{c''}$ represents a hydrogen atom or an alkyl or alkenyl group, said alkyl or alkenyl groups mentioned above containing from 1 to 4 carbon atoms, $R_5$ and $R_6$ represent hydrogen atoms or alkyl or haloalkyl groups, said alkyl and haloalkyl groups containing from 1 to 4 carbon atoms, $R_7$ and $R_8$ represent hydrogen atoms or alkyl groups containing from 1 to 4 carbon atoms, or together form a 5- or 6-membered saturated ring, Alk represents a linear or branched alkylene chain containing from 1 to 4 carbon atoms, and Alk' represents a linear, branched, cyclic or partially cyclic alkylene chain containing from 1 to 4 carbon atoms.

Among the compounds which are the subjects of the invention, mention may be made of the following compounds:

6-[(1-methoxy-2-methylindolizin-3-yl)carbonyl]-1,2-dimethyl-4-oxo-1,4-dihydroquinoline-3-carboxamide 6-[(1-methoxy-2-methylindolizin-3-yl)carbonyl]-1-methyl-4-oxo-1,4-dihydroquinoline-3-carboxylic acid 2-{6-[(1-methoxy-2-methylindolizin-3-yl)carbonyl]-2,4-dioxo-1,4-dihydroquinazolin-3(2H)-yl}-N,N'-dimethylacetamide 6-[(1-methoxy-2-methyl indolizin-3-yl)carbonyl]-3-propylquinazoline-2,4(1H,3H)-dione {6-[(1-methoxy-2-methylindolizin-3-yl)carbonyl]-2,4-dioxo-1,4-dihydroquinazolin-3(2H)-yl}acetic acid methyl {6-[(1-methoxy-2-methylindolizin-3-yl)carbonyl]-2,4-dioxo-1,4-dihydroquinazolin-3(2H)-yl}acetate 6-[(1-methoxy-2-methylindazin-3-yl)carbonyl]-2-methylquinazolin-4(3H)-one 1-{6-[(1-methoxy-2-methylindolizin-3-yl)carbonyl]-2,4-dioxo-1,4-dihydroquinazolin-3(2H)-yl}-N,N-dimethylcyclopropanecarboxamide 6-[(1-methoxy-2-methylindolizin-3-yl)carbonyl]-1,2-dimethyl-4-oxo-1,4-dihydroquinoline-3-carboxamide 6-[(1-methoxy-2-methylindolizin-3-yl)carbonyl]-3-methylquinazoline-2,4(1H,3H)-dione.

6-[(1-methoxy-2-methylindolizin-3-yl)carbonyl]-N-methyl-4-oxo-1,4-dihydroquinoline-3-carboxamide N-1-dimethyl-6-[(2-methylindolizin-3-yl)carbonyl]-4-oxo-1,4-dihydroquinoline-3-carboxamide.

In the following text, the term "protective group" is intended to mean a group which makes it possible, firstly, to protect a reactive function such as a hydroxyl or an amine during a synthesis and, secondly, to regenerate the intact reactive function at the end of synthesis. Examples of protective groups and also methods of protection and deprotection are given in "Protective Groups in Organic Synthesis", Green et al., 3$^{rd}$ Edition (John Wiley & Sons, Inc., New York).

In the remainder of the text, the term "leaving group" is intended to mean a group that can be readily cleaved from a molecule by breaking a heterolytic bond, with the departure of a pair of electrons. This group can thus be readily replaced with another group during a substitution reaction, for example. Such leaving groups are, for example, halogens or an activated hydroxyl group, such as a mesyl, tosyl, triflate, acetyl, para-nitrophenyl, etc. Examples of leaving groups and also methods for the preparation thereof are given in "Advances in Organic Chemistry", J. March, 3$^{rd}$ Edition, Wiley Interscience, p. 310-316.

In accordance with the invention, the compounds of general formula (I) can be prepared according to the processes hereinafter.

Scheme 1 presents a pathway for obtaining the compounds of formula (I) in which $R_3$ and $R_4$ together form a nitrogenous heterocycle of formula (A) as defined above, $R_1$ represents an —OR$_5$, —O-Alk-OR$_5$, —COOR$_5$, —O-Alk-COOR$_5$, —O-Alk-OR$_5$, O-Alk-NR$_5$R$_6$ or —O-Alk-NR$_7$R$_5$ group, and $R_2$ represents a group as defined above.

Scheme 1 (Method 1):

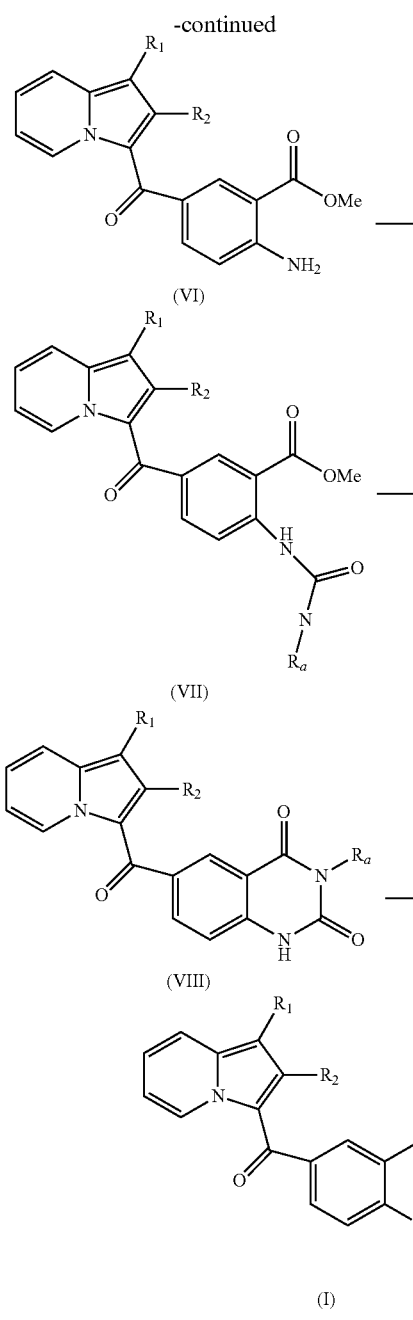

Scheme 2 presents a pathway for obtaining the compounds of formula (I) in which $R_3$ and $R_4$ together form a nitrogenous heterocycle of formula (A) as defined above, $R_1$ is as defined above, except for an —$OR_5$, —O-Alk-$OR_5$, —$COOR_5$, —O-Alk-$COOR_5$, —O-Alk-$OR_5$, O-Alk-$NR_5R_6$ or —O-Alk-$NR_7R_5$ group, and $R_2$ represents a group as defined above.

Scheme 2 (Method 2):

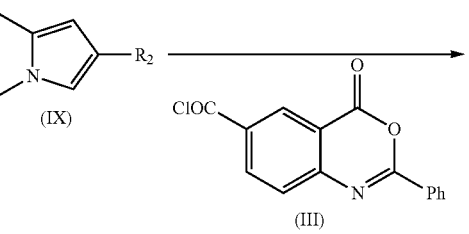

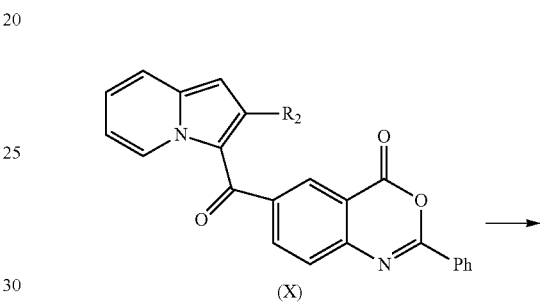

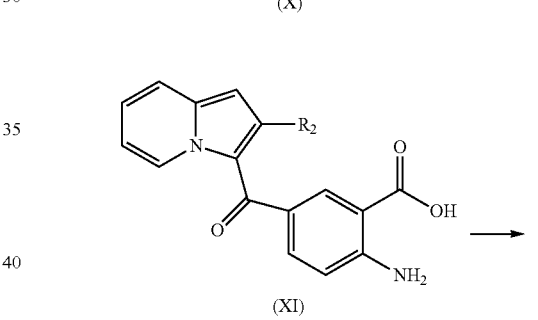

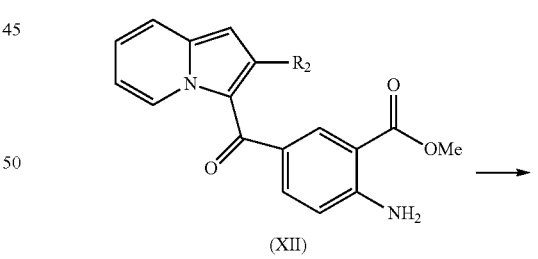

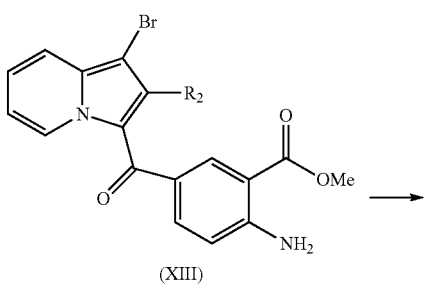

The compound of formula II (obtained according to a Tschitschibabin reaction described in WO 03084956) in which $R_1$ and $R_2$ are as defined for the compound of formula I, is condensed with the compound of formula III in order to obtain the compound of formula IV. The compound of formula IV is subjected to a basic hydrolysis reaction in order to obtain the compound of formula V. The esterification of the compound of formula V produces the compound of formula VI. By reacting triphosgene, the isocyanate corresponding to the compound of formula VI is formed, which is condensed with an amine of formula $R_aNH_2$ in order to obtain the urea of formula VII. The compound of formula VII is subjected to a cyclization reaction in a basic medium in order to obtain the compound of formula VIII. The compound VIII is subjected to an alkylation reaction in the presence of a base and of a halogenated derivative Ra'X in order to obtain the compound of formula I in which $R_2$ is as defined above.

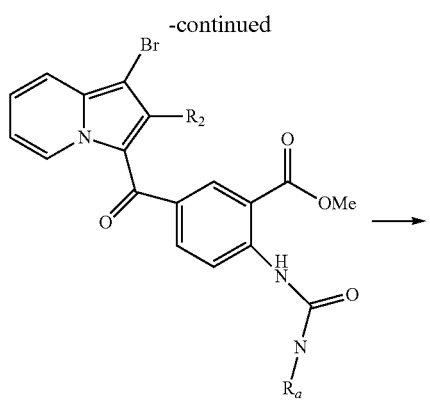

(XIV)

(XV)

(XVI)

(I)

The compound of formula IX (obtained according to a Tschitschibabin reaction described in WO 03084956), in which $R_2$ is as defined for the compound of formula I, is condensed with the compound of formula III in order to obtain the compound of formula X. The compound of formula X is subjected to a basic hydrolysis reaction in order to obtain the compound of formula XI. The esterification of the compound of formula XI results in the compound of formula XII. By reacting N-Bromosuccinimide, the compound of formula XIII is formed. By reacting triphosgene, the isocyanate corresponding to the compound of formula XIII is formed, which is condensed with an amine of formula $R_a NH_2$ in order to obtain the urea of formula XIV. The compound of formula XIV is subjected to a cyclization reaction in a basic medium, in order to obtain the compound of formula XV. The compound of formula XV is subjected, in the presence of a palladium catalyst, of a ligand and of a base, to a reaction with phenylboronic or heteroarylboronic or phenylboronate ester or heteroarylboronate ester derivatives according to a Suzuki coupling, or else to a cyanation reaction with zinc cyanide, followed by an acid hydrolysis, in order to obtain the compound of formula XVI. The compound XVI is subjected to an alkylation reaction in the presence of a base and of a halogenated derivative Ra'X in order to obtain the compound of formula I in which $R_2$ is as defined above and $R_1$ is as defined above, except for an —$OR_5$, —O-Alk-$OR_5$, —$COOR_5$, —O-Alk-$COOR_5$, —O-Alk-$OR_5$, O-Alk-$NR_5R_6$ or —O-Alk-$NR_7R_6$ group.

Scheme 3 presents a pathway for obtaining the compounds of formula (I) in which $R_3$ and $R_4$ together form a nitrogenous heterocycle of formula (B) as defined above, and in which $R_1$ is as defined above except for a aryl or heteroaryl group optionally substituted with one or more alkyl, —$OR_5$, —$NR_5R_6$ or —$COOR_5$ groups, and $R_2$ is as defined above.

Scheme 3 (Method 3):

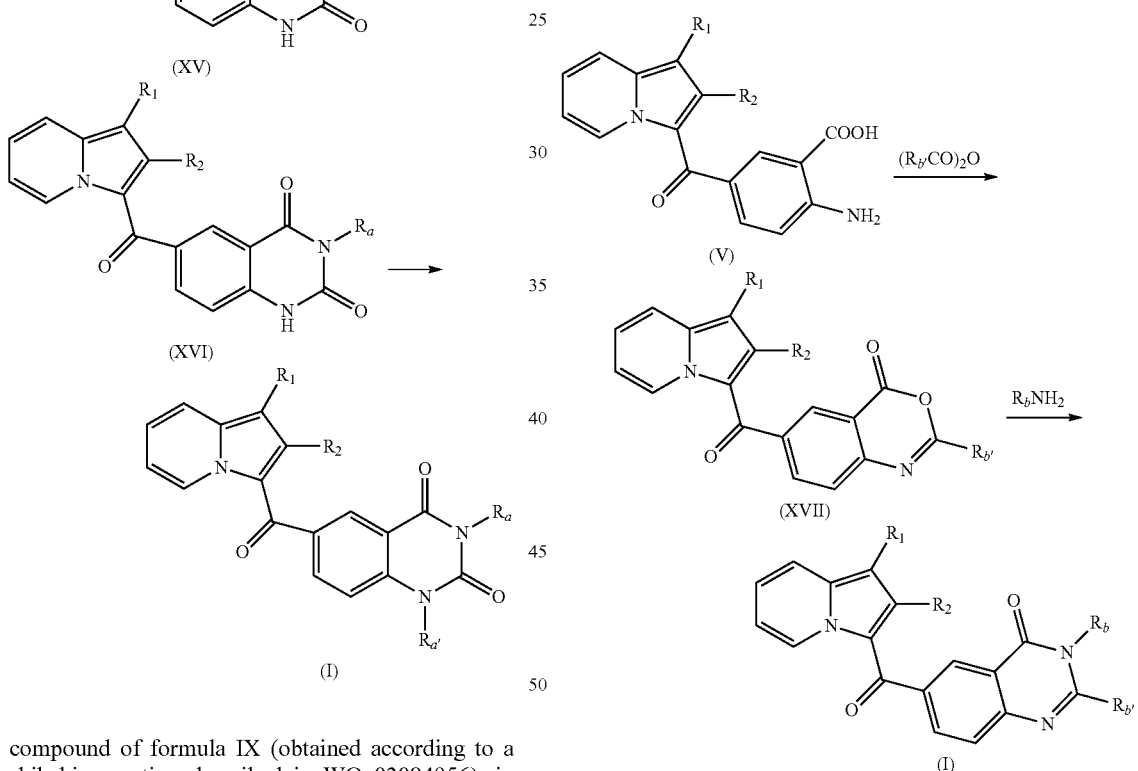

The compound of formula V in which $R_1$ is as defined above, except for a phenyl group optionally substituted with one or more alkyl or —$COOR_5$ groups, is subjected to a condensation reaction with an acid anhydride in order to obtain the compound of formula XVII in which $R_1$ and $R_2$ are as defined above. The compound XVII is subjected to a substitution reaction in order to obtain the compound of formula I in which $R_1$ and $R_2$ are as defined above.

Scheme 4 presents a pathway for obtaining the compounds of formula (I) in which $R_3$ and $R_4$ together form a nitrogenous heterocycle of formula (B) as defined above, and in which $R_1$ represents an aryl or heteroaryl group optionally substituted with one or more alkyl, —OR$_5$, —NR$_5$R$_6$ or —COOR$_5$ groups, and R$_2$ represents a group as defined above.

Scheme 4 (Method 4):

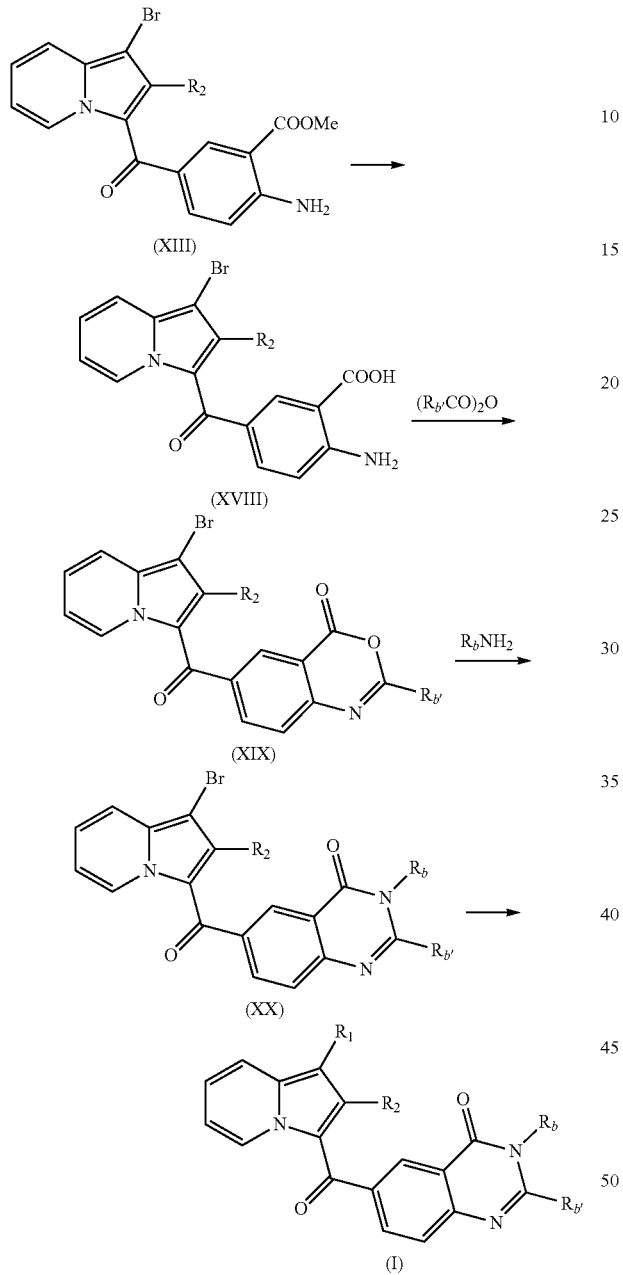

The compound of formula XIII is subjected to a saponification reaction in a basic medium in order to obtain the compound XVIII. The compound XVIII is subjected to a condensation reaction with an acid anhydride in order to obtain the compound of formula XIX. The compound XIX is subjected to a substitution reaction in order to obtain the compound of formula XX. The compound of formula XX is subjected, in the presence of a palladium catalyst, of a ligand and of a base, to a reaction with phenylboronic or heteroarylboronic or phenylboronate ester or heteroarylboronate ester derivatives according to a Suzuki coupling, in order to obtain the compound of formula I in which R$_1$ and R$_2$ are as defined above.

Scheme 5 presents a pathway for obtaining the compounds of formula (I) in which R$_3$ and R$_4$ together form a nitrogenous heterocycle of formula (C) as defined above, and in which R$_1$ represents an —OR$_5$, —O-Alk-OR$_5$, —COOR$_5$, —O-Alk-COOR$_5$, —O-Alk-OR$_5$, O-Alk-NR$_5$R$_6$ or —O-Alk-NR$_7$R$_8$ group, and R$_2$ is as defined above.

Scheme 5 (Method 5):

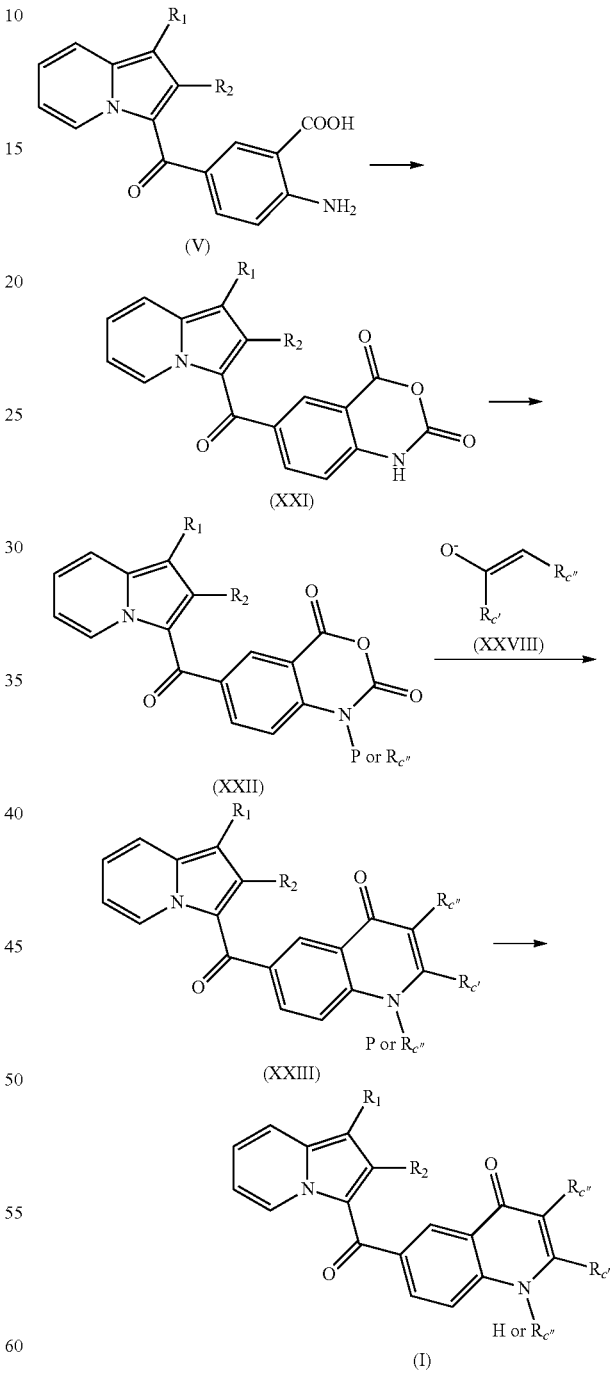

The compound V is subjected to a condensation reaction in order to obtain the compound XXI. The compound XXI is subjected to an alkylation reaction in the presence of a base and of a halogenated derivative R$_{c''}$X or of a protective group in order to obtain the compound XXII. The compound XXII is subjected to a condensation reaction with a malonic derivative in order to obtain the compound XXIII in which Rc' and Rc are as defined above. The compound XXIII is subjected to a deprotection reaction in order to obtain the compounds of formula I in which $R_1$ and $R_2$ are as defined above.

Scheme 6 presents a pathway for obtaining the compounds of formula (I) in which $R_3$ and $R_4$ together form a nitrogenous heterocycle of formula (C) as defined above and in which $R_1$ represents an aryl or heteroaryl group, where the aryl or heteroaryl group is optionally substituted with one or more alkyl, —$OR_5$, —$NR_5R_6$ or —$COOR_5$ groups, and $R_{c''}$ preferentially represents an alkyl and $R_{c''}$ and $R_2$ are as defined above.

Scheme 6 (Method 6):

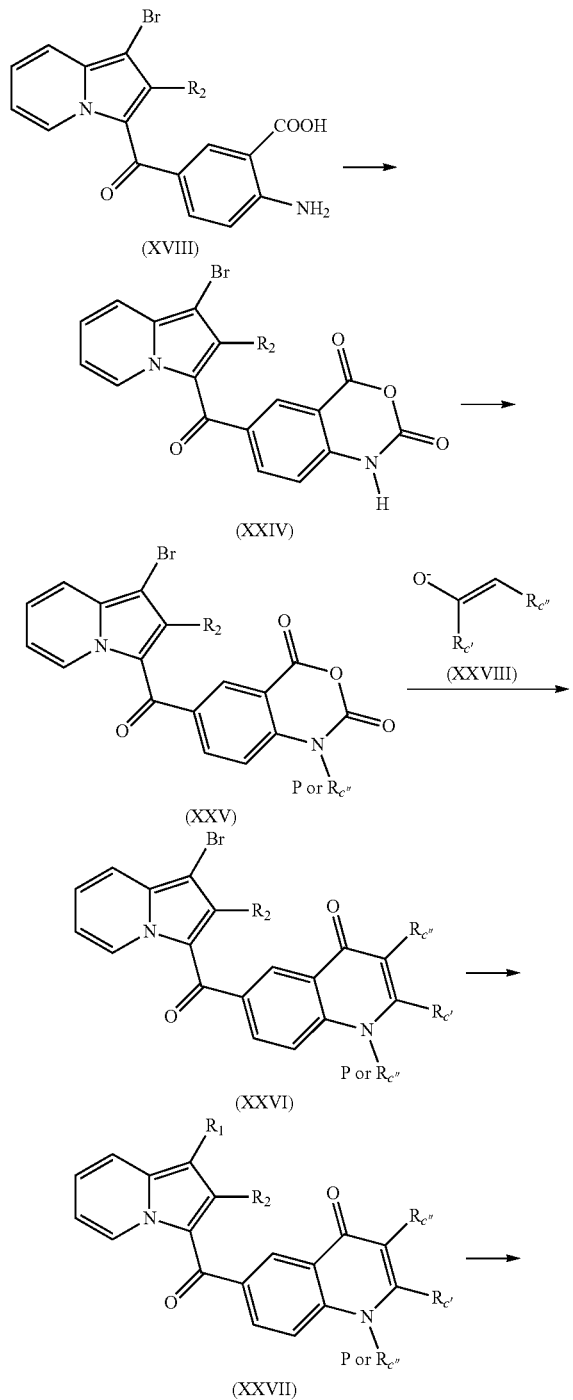

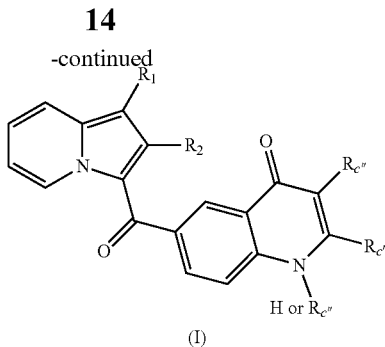

The compound XVIII is subjected to a condensation reaction in order to obtain the compound XXIV. The compound XXIV is subjected to an alkylation reaction in the presence of a base and of a halogenated derivative $R_{c''}X$ or of a protective group in order to obtain the compound XXV. The compound XXV is subjected to a condensation reaction with a malonic derivative in order to obtain the compound XXVI in which Rc' and Rc are as defined above. The compound XXVI is subjected, in the presence of a palladium catalyst, of a ligand and of a base, to a reaction with phenylboronic or heteroarylboronic or phenylboronate ester or heteroarylboronate ester derivatives according to a Suzuki coupling, in order to obtain the compound of formula XXVII. The compound XXVII is subjected to a deprotection reaction in order to obtain the compounds of formula I in which $R_1$ and $R_2$ are as defined above.

Scheme 7 presents a pathway for obtaining the compounds of formula (I) in which $R_3$ and $R_4$ together form a nitrogenous heterocycle of formula (C) with $R_{c'}$ representing a hydrogen and $R_c$ and $R_{c''}$ as defined above, and in which $R_1$ represents a hydrogen or an —$OR_5$, —O-Alk-$OR_5$, —$COOR_5$, —O-Alk-$COOR_5$, —O-Alk-$OR_5$, O-Alk-$NR_5R_6$ or —O-Alk-$NR_7R_8$ group, and $R_2$ is as defined above.

Scheme 7 (Method 7):

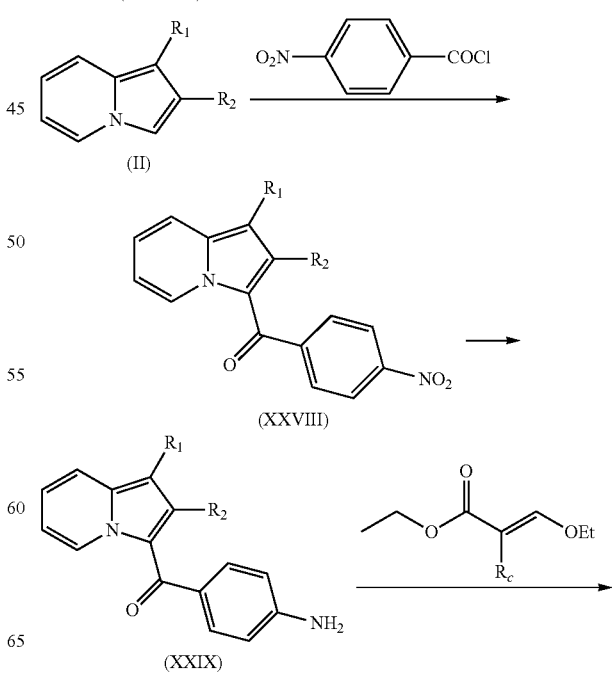

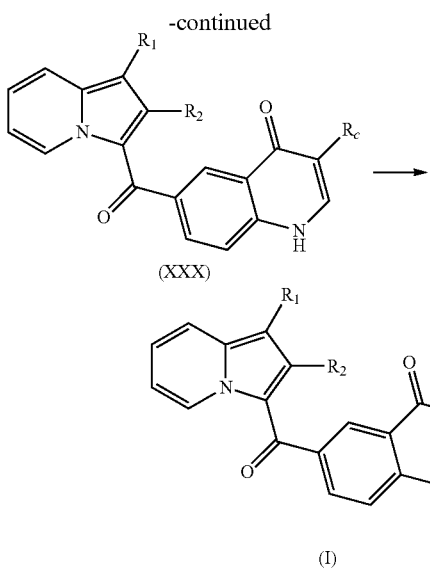

The compound of formula II, in which $R_1$ and $R_2$ are as defined above, is condensed with 4-nitrobenzoic acid chloride in order to obtain the compound XXVIII. The compound XXVIII is subjected to a reduction in the presence of iron and of acetic acid in order to obtain the compound XXIX. The compound XXIX is subjected to a condensation reaction in order to obtain the compound XXX. The compound XXX is subjected to an alkylation reaction in the presence of a halide $R_{c''}X$ and of a base in order to obtain the compound of formula I in which $R_1$ and $R_2$ are as defined above.

In the preceding schemes, the starting compounds and the reactants, when the method for preparing them is not described, are commercially available or described in the literature, or else can be prepared according to methods which are described therein or which are known to those skilled in the art.

A subject of the invention, according to another of its aspects, is also the compounds of formulae (I) to (XXX) defined above. These compounds are of use as synthesis intermediates for the compounds of formula (I).

The following examples describe the preparation of certain compounds in accordance with the invention. These examples are not limiting and merely illustrate the present invention. The numbers of the compounds exemplified refer back to those given in the table hereinafter, which illustrates the chemical structures and the physical properties of some compounds according to the invention.

The reactants and intermediates, when their preparation is not explained, are known in the literature or commercially available. Some intermediates that are of use for preparing the compounds of formula I may also serve as final products of formula (I), as will become apparent in the examples given hereinafter. Similarly, some compounds of formula (I) of the invention can serve as intermediates that are of use for preparing other compounds of formula (I) according to the invention.

By way of example, the compounds of formula (I) are selected from the following compounds:
2-{6-[(1-methoxy-2-methylindolizin-3-yl)carbonyl]-2,4-dioxo-1,4-dihydroquinazolin-3(2H)-yl}-N,N'-dimethylacetamide,
2-{6-[(1-methoxy-2-methylindolizin-3-yl)carbonyl]-1-methyl-2,4-dioxo-1,4-dihydroquinazolin-3(2H)-yl}-N,N'-dimethylacetamide,
6-[(1-methoxy-2-methylindolizin-3-yl)carbonyl]-3-[(3-methyl-1,2,4-oxadiazol-5-yl)methyl]quinazoline-2,4(1H,3H)-dione,
3-{3-(2,4-dioxo-3-propyl-1,2,3,4-tetrahydroquinazolin-6-yl)carbonyl}-2-methylindolizin-1-yl}benzoic acid,
{6-[(1-methoxy-2-phenylindolizin-3-yl)carbonyl]-2,4-dioxo-1,4-dihydroquinazolin-3(2H)-yl}-acetic acid,
Ethyl({6-[(1-methoxy-2-methylindolizin-3-yl)carbonyl]-2,4-dioxo-1,4-dihydroquinazolin-3(2H)-yl}oxy)acetate,
3-amino-6-[(1-methoxy-2-methylindolizin-3yl)carbonyl]quinazoline-2,4(1H,3H)-dione,
6-[(1-methoxy-2-methylindolizin-3-yl)carbonyl]-2-methylquinazolin-4(3H)-one,
3-{2-methyl-3-[(2-methyl-4-oxo-3,4-dihydroquinazolin-6-yl)carbonyl]indolizin-1-yl}benzoic acid,
6-{[1(2-methoxyethoxy)-2-methylindolizin-3-yl]carbonyl}-3-propylquinazoline-2,4(1H,3H)-dione,
6-[(1-methoxy-2-methylindolizin-3-yl)carbonyl]-1-methyl-4-oxo-1,4-dihydroquinoline-3-carboxylic acid,
6-[(1-methoxy-2-methylindolizin-3-yl)carbonyl]-2-methyl-4-oxo-1,4-dihydroquinoline-3-carboxylic acid,
6-[(1-methoxy-2-methylindolizin-3-yl)carbonyl]-N-methyl-4-oxo-1,4-dihydroquinoline-3-carboxamide,
N-1-dimethyl-6-[(2-methylindolizin-3-yl)carbonyl]-4-oxo-1,4-dihydroquinoline-3-carboxamide,
N-1-dimethyl-6-{[2-methyl-1-(pyridin-4-yl)indolizin-3-yl]carbonyl}-4-oxo-1,4-dihydroquinoline-3-carboxamide hydrochloride.

Abbreviations
DMF: N,N-dimethylformamide
THF: tetrahydrofuran
DBU: 1,8-diazabicyclo[5.4.0]undec-7-ene
HBTU: O-benzotriazol-1-yl-N,N,N',N'-tetramethyluronium hexafluorophosphate
DIEA: Diisopropylethylamine
DME: Ethylene glycol dimethyl ether
TOTU: O-[(ethoxycarbonyl)cyanomethyleneamino]-N,N,N',N'-tetramethyluronium tetra-fluoroborate The NMR analyses were carried out on Bruker Avance 250 MHz, 300 MHz and 400 MHz instruments.

The melting points were measured on a Buchi B-450 instrument.

The mass spectrometry analyses were carried out on a Waters Alliance 2695 (UV: PDA996, MS: LCZ), Alliance 2695 (UV: PDA 996, MS: ZQ (simple Quad) ZQ1), Alliance 2695 (UV: PDA 996, MS: ZQ (simple Quad) ZQ2), Waters UPLC Acquity (UV: Acquity PDA, MS: SQD (simple Quad) SQVV), Agilent MSD, Waters ZQ, or Waters SQD instrument.

EXAMPLE 1

Compound No 35

2-{6-[(1-Methoxy-2-methylindolizin-3-yl)carbonyl]-2,4-dioxo-1,4-dihydroquinazolin-3(2H)-yl}-N,N'-dimethylacetamide Methyl 2-amino-5-[(1-methoxy-2-methylindolizin-3-yl)carbonyl]benzoate 1.51 ml (24.26 mmol) of methyl iodide are added, under an inert atmosphere at ambient temperature, to 8 g (23.1 mmol) of the sodium salt of 2-amino-5-[(1-methoxy-2-methylindolizin-3-yl)carbonyl]benzoic acid (described in WO 03/084956) in 130 ml of DMF. After stirring for 1 hour, water is added. The precipitate formed is filtered off, rinsed with water, and then dried under reduced pressure at 50° C. overnight. 7.17 g of a yellow solid are obtained.
MH+: 339

Methyl 2-({[2-(dimethylamino)-2-oxoethyl]
carbamoyl}amino)-5-[(1-methoxy-2-methylin-
dolizin-3-yl)carbonyl]benzoate 0.798 g (2.69 mmol) of triphosgene diluted in 10 ml of dioxane is added, under an inert atmosphere at ambient temperature, to 1.3 g (3.84 mmol) of methyl 2-amino-5-[(1-methoxy-2-methylindolizin-3-yl)carbonyl]benzoate in 50 ml of dioxane. After stirring for 1 hour, 1.25 g (7.68 mmol) of N,N-dimethylglycinamide acetate and 2.68 ml (19.21 mmol) of triethylamine are added. The reaction medium is stirred overnight at ambient temperature and then hydrolysed with water. The aqueous phase is extracted with dichloromethane. The organic phase obtained is dried over sodium sulphate, filtered, and then concentrated under reduced pressure. 1.8 g of a yellow solid are obtained.
Melting point: 228° C.
MH+=467

2-{6-[(1-Methoxy-2-methylindolizin-3-yl)carbonyl]-
2,4-dioxo-1,4-dihydroquinazolin-3(2H)-yl}-N,N'-
dimethylacetamide 0.69 ml (4.63 mmol) of DBU is added, at ambient temperature under an inert atmosphere, to 1.8 g (3.86 mmol) of methyl 2-({[2-(dimethylamino)-2-oxoethyl]carbamoyl}amino)-5-[(1-methoxy-2-methylindolizin-3-yl)carbonyl]benzoate in 25 ml of THF. The reaction medium is stirred overnight at ambient temperature. The THF is concentrated under reduced pressure. The residue is taken up in water. The aqueous phase is extracted with dichloromethane. The organic phase obtained is dried over sodium sulphate, filtered, and then concentrated under reduced pressure. The yellow solid obtained is purified by silica gel column chromatography, elution being carried out with a dichloromethane/methanol (95/5) mixture. The orange foam obtained is taken up in a minimum amount of methanol. After the addition of water, the precipitate obtained is filtered off, rinsed with water, and then dried under reduced pressure at 50° C. overnight. 1.14 g of a yellow powder are obtained.
Melting point: 290° C.
MH+=435
$^1$H-NMR (D6-DMSO, 400 MHz) δ ppm:
1.82 (s, 3H), 2.85 (s, 3H), 3.08 (s, 3H), 3.83 (s, 3H), 4.75 (s, 2H), 6.95 (t, J=6.85 Hz, 1H), 7.19-7.24 (m, 1H), 7.32 (d, J=8.43, 1H), 7.66 (d, J=8.87 Hz, 1H), 7.91 (d, J=8.47 Hz, 1H), 8.09 (d, J=2.02 Hz, 1H), 9.53 (d, J=7.26 Hz, 1H), 11.83 (s, 1H).

EXAMPLE 2

Compound No. 68

2-{6-[(1-Methoxy-2-methylindolizin-3-yl)carbonyl]-
1-methyl-2,4-dioxo-1,4-dihydroquinazolin-3(2H)-
yl}-N,N-dimethylacetamide 0.04 ml (0.69 mmol) of methyl iodide and 0.225 g (0.69 mmol) of caesium carbonate are added, under an inert atmosphere at ambient temperature, to 0.150 g (0.35 mmol) of 2-{6-[(1-methoxy-2-methylindolizin-3-yl)carbonyl]-2,4-dioxo-1,4-dihydroquinazolin-3(2H)-yl}-N,N'-dimethylacetamide in 5 ml of DMF. The reaction medium is stirred for 2.5 hours at ambient temperature and then hydrolysed with water. The aqueous phase is extracted with ethyl acetate. The organic phase obtained is washed with water, dried over sodium sulphate, filtered, and then concentrated under reduced pressure. The residue is purified by silica gel column chromatography, elution being carried out with a dichloromethane/methanol (95/5) mixture. The solid obtained is taken up in a minimum amount of methanol. After the addition of water, the precipitate obtained is filtered off, rinsed with water, and then dried under reduced pressure at 50° C. overnight. 0.135 g of a yellow solid is obtained.
Melting point: 276° C.
MH+: 449
$^1$H-NMR (D6-DMSO, 400 MHz) δ ppm:
1.82 (s, 3H), 2.85 (s, 3H), 3.09 (s, 3H), 3.60 (s, 3H), 3.83 (s, 3H), 4.81 (s, 2H), 6.97 (t, J=7.05 Hz, 1H), 7.21-7.26 (m, 1H), 7.62 (d, J=8.75 Hz, 1H), 7.67 (d, J=8.75 Hz, 1H), 8.02 (d, J=8.67H, 1H), 8.19 (d, J=2.19 Hz, 1H), 9.75 (d, J=7.13 Hz, 1H).

EXAMPLE 3

Compound No. 36

6-[(1-Methoxy-2-methylindolizin-3-yl)carbonyl]-3-
[(3-methyl-1,2,4-oxadiazol-5-yl)methyl]quinazoline-
2,4(1H,3H)-dione Methyl {6-[(1-methoxy-2-methylindolizin-3-yl)car-
bonyl]-2,4-dioxo-1,4-dihydroquinazolin-3(2H)-
yl}acetate 1.22 g (4.14 mmol) of triphosgene diluted in 15 ml of dioxane are added, under an inert atmosphere at ambient temperature, to 2 g (5.91 mmol) of methyl 2-amino-5-[(1-methoxyindolizin-3-yl)carbonyl]benzoate in 65 ml of dioxane. The reaction medium is stirred for 1 hour at ambient temperature and then 1.48 g (11.82 mmol) of methyl glycinate and 4.12 ml (29.55 mmol) of triethylamine are added. The reaction medium is stirred for 18 hours and then 1.08 g (5.91 mmol) of DBU are added. After stirring for 24 hours, the medium is hydrolysed with water. The aqueous phase is extracted with dichloromethane. The organic phase obtained is washed with water, dried over sodium sulphate, filtered, and then concentrated under reduced pressure. The solid is purified by silica gel column chromatography, elution being carried out with a dichloromethane/methanol (95/5) mixture. The solid obtained is recrystallized, under hot conditions, from methanol. 1.5 g of a yellow solid are obtained.
Melting point: 253° C.
MH+=422

6-[(1-Methoxy-2-methylindolizin-3-yl)carbonyl]-3-
[(3-methyl-1,2,4-oxadiazol-5-yl)methyl]quinazoline-
2,4(1H,3H)-dione 0.14 g (0.37 mmol) of HBTU, 0.21 ml (1.23 mmol) of DIEA and then 0.18 g (1.23 mmol) of (1E)-N'-hydroxyethanimidamide are added, under an inert atmosphere at ambient temperature, to 0.1 g (0.25 mmol) of methyl {6-[(1-methoxy-2-methylindolizin-3-yl)carbonyl]-2,4-dioxo-1,4-dihydroquinazolin-3(2H)-yl}acetate in 5 ml of DMF. The reaction medium is heated at 90° C. for 24 hours. After hydrolysis with water, the reaction medium is extracted with ethyl acetate. The organic phase is washed with a saturated aqueous solution of sodium hydrogen carbonate and then with water, dried over sodium sulphate, filtered, and then concentrated under reduced pressure. The yellow solid obtained is purified by silica gel column chromatography, elution being carried out with a dichloromethane/methanol (95/5) mixture. 0.046 g of a yellow solid is obtained.

Melting point: 176° C.
MH+: 446
$^1$H-NMR (D6-DMSO, 500 MHz) δ ppm:
1.82 (s, 3H), 2.30 (s, 3H), 3.82 (s, 3H), 5.36 (s, 2H), 6.96 (t, J=7.04 Hz, 1H), 7.20-7.24 (m, 1H), 7.35 (d, J=8.48 Hz, 1H), 7.66 (d, J=8.81 Hz, 1H), 7.94 (d, J=8.32 Hz, 1H), 8.11 (d, J=1.92 Hz, 1H), 9.54 (d, J=7.43 Hz, 1H), 12.01 (s, 1H).

EXAMPLE 4

Compound No. 14

Sodium salt of 3-{(3-[(2,4-dioxo-3-propyl-1,2,3,4-tetrahydroquinazolin-6-yl)carbonyl}-2-methylindolizin-1-yl]benzoic acid Methyl 2-amino-5-[(1-bromo-2-methylindolizin-3-yl)carbonyl]benzoate 0.492 g (2.73 mmol) of N-bromosuccinimide is added, under an inert atmosphere at ambient temperature, to 0.812 g (2.6 mmol) of methyl 2-amino-5-[(2-methylindolizin-3-yl)carbonyl]benzoate in 17 ml of dichloromethane. The reaction medium is stirred for 2 hours and then hydrolysed with water. The aqueous phase is extracted with dichloromethane. The organic phase obtained is washed with a saturated aqueous solution of sodium hydrogen carbonate and then with a saturated aqueous solution of sodium chloride, dried over sodium sulphate, filtered, and then concentrated under reduced pressure. The solid obtained is purified by silica gel column chromatography, elution being carried out with dichloromethane. 0.9 g of a yellow solid is obtained.

MH+: 387, 389

Methyl 2-amino-5-({1-[3-(methoxycarbonyl)phenyl]-2-methylindolizin-3-yl}carbonyl)benzoate 0.229 g (1.27 mmol) of [3-(methoxycarbonyl)phenyl]boronic acid, 0.492 g (2.12 mmol) of potassium phosphate dihydrate and 0.024 g (0.02 mmol) of tetrakis(triphenylphosphine)palladium are added, under an argon atmosphere at ambient temperature, to 0.410 g (1.06 mmol) of methyl 2-amino-5-[(1-bromo-2-methylindolizin-3-yl)carbonyl]benzoate in 8 ml of a DME/H$_2$O (5/1) mixture. The reaction medium is heated at 90° C. for 18 hours. The reaction medium is extracted with dichloromethane, washed with a saturated aqueous solution of sodium chloride, dried over sodium sulphate, filtered, and then concentrated under reduced pressure. The solid obtained is purified by silica gel column chromatography, elution being carried out with dichloromethane. 309 mg of a yellow solid are obtained.

Melting point: 232° C.
MH+: 443

Methyl 5-({1-[3-(methoxycarbonyl)phenyl]-2-methylindolizin-3-yl}carbonyl)-2-[(propylcarbamoyl)amino]benzoate 0.143 mg (0.47 mmol) of triphosgene diluted in 2 ml of dioxane are added, under an inert atmosphere at ambient temperature, to 308 mg (0.68 mmol) of methyl 2-amino-5-({1-[3-(methoxycarbonyl)phenyl]-2-methylindolizin-3-yl}carbonyl)benzoate in 5.6 ml of dioxane. The reaction medium is stirred for 2 hours at ambient temperature and then 0.28 ml (2.03 mmol) of triethylamine, and 0.11 ml (1.35 mmol) of n-propylamine diluted in 4 ml of dioxane are added. After stirring for 2 hours, the reaction medium is hydrolysed with water. The aqueous phase is extracted with dichloromethane. The organic phase obtained is washed with a 1N aqueous solution of hydrochloric acid, and then with a saturated aqueous solution of sodium chloride, dried over sodium sulphate, filtered, and concentrated under reduced pressure. The solid obtained is purified by silica gel column chromatography, elution being carried out with a dichloromethane/methanol (95/5) mixture.

215 mg of a yellow solid are obtained.
Melting point: 143° C.
MH+: 496

Sodium salt of 3-{3-[(2,4-dioxo-3-propyl-1,2,3,4-tetrahydroquinazolin-6-yl)carbonyl]-2-methylindolizin-1-yl}benzoic acid 0.96 ml (0.96 mmol) of a 1N aqueous solution of sodium hydroxide is added, at ambient temperature, to 0.203 mg (0.39 mmol) of methyl 5-({1-[3-(methoxy-carbonyl)phenyl]-2-methylindolizin-3-yl}carbonyl)-2-[(propylcarbamoyl)amino]benzoate in 4 ml of methanol. The reaction medium is refluxed for 7 hours.

The reaction medium is acidified with a 1N aqueous solution of hydrochloric acid. The precipitate obtained is filtered off, rinsed with water, and dried under reduced pressure at 50° C. overnight.

0.31 ml (0.31 mmol) of a 1N aqueous solution of sodium hydroxide is added, at ambient temperature, to 0.158 g (0.33 mmol) of the solid obtained. The reaction medium is stirred for one hour and then diisopropyl ether is added. The precipitate obtained is filtered off, rinsed with diisopropyl ether, and then dried under reduced pressure at 50° C. overnight. 155 mg of a yellow solid are obtained.

Melting point: 361° C.
MH+: 504
$^1$H-NMR (D6-DMSO, 400 MHz) δ ppm:
0.88 (t, J=7.97 Hz, 3H), 1.52-1.64 (m, 2H), 1.96 (s, 3H), 3.80-3.88 (m, 2H), 6.94 (t, J=6.78 Hz, 1H), 7.12 (d, J=8.38 Hz, 1H), 7.16-7.22 (m, 1H), 7.34 (d, J=7.58 Hz, 1H), 7.39 (t, J=758 Hz, 1H), 7.51 (d, J=8.78 Hz, 1H), 7.80-7.86 (m, 2H), 7.92-7.95 (m, 1H), 8.17 (d, J=2 Hz, 1H), 9.33 (d, J=7.58 Hz, 1H).

EXAMPLE 5

Compound No. 24

Sodium salt of {6-[(1-methoxy-2-phenylindolizin-3-yl)carbonyl]-2,4-dioxo-1,4-dihydroquinazolin-3(2H)-yl}acetic acid 6-[(1-Methoxy-2-phenylindolizin-3-yl)carbonyl]-2-phenyl-4H-3,1-benzoxazin-4-one 2.25 ml (16.12 mmol) of triethylamine and 3 g (13.44 mmol) of 1-methoxy-2-phenylindolizine (according to the method described in WO 03/084956) diluted in 20 ml of dichloroethane are added, under an inert atmosphere at ambient temperature, to 4.22 g (14.78 mmol) of 4-oxo-2-phenyl-4H-3,1-benzoxazine-6-carboxylic acid (described in WO 06/097625) in 100 ml of dichloroethane. After stirring overnight at ambient temperature, the reaction medium is filtered, and rinsed with dichloroethane. The filtrate is washed with water, dried over sodium sulphate, filtered, and concentrated under reduced pressure. The residue is filtered through a silica pâté, elution being carried out with dichloromethane. 4.4 g of a yellow solid are obtained.

MH+: 473

2-Amino-5-[(1-methoxyindolizin-3-yl)carbonyl]benzoic acid 1.56 g (27.94 mmol) of potassium hydroxide dissolved in 4 ml of water are added, at ambient temperature, to 4.4 g (9.31 mmol) of 6-[(1-methoxy-2-phenylindolizin-3-yl)carbonyl]-2-phenyl-4H-3,1-benzoxazin-4-one in 50 ml of N-methylpyrrolidone. The reaction medium is heated at 80° C. for 24 hours. The reaction medium is poured into a 1N aqueous solution of hydrochloric acid. The precipitate formed is filtered off and rinsed with water. The residue obtained is purified by silica gel column chromatography, elution being carried out with a dichloromethane/methanol (95/5) mixture. 3.05 g of a green solid are obtained.

Melting point: 106° C.
MH+: 387

Methyl 2-amino-5-[(1-methoxy-2-phenylindolizin-3-yl)carbonyl]benzoate 0.54 ml (8.63 mmol) of methyl iodide and 2.8 g (8.63 mmol) of caesium carbonate are added, under an inert atmosphere at ambient temperature, to 3.03 g (7.84 mmol) of 2-amino-5-[(1-methoxyindolizin-3-yl)carbonyl]benzoic acid in 50 ml of DMF. After stirring for 3 hours at ambient temperature, water is added. The precipitate formed is filtered off, rinsed with water, and then dried under reduced pressure at 50° C. overnight. The solid obtained is purified by silica gel column chromatography, elution being carried out with dichloromethane. 1.98 g of a yellow solid are obtained.

MH+: 401

Ethyl {6-[(1-methoxy-2-phenylindolizin-3-yl)carbonyl]-2,4-dioxo-1,4-dihydroquinazolin-3(2H)-yl}acetate 0.208 g (0.7 mmol) of triphosgene diluted in 15 ml of dioxane is added, under an inert atmosphere at ambient temperature, to 0.4 g (1 mmol) of methyl 2-amino-5-[(1-methoxyindolizin-3-yl)carbonyl]benzoate in 50 ml of dioxane. After stirring for 1 hour, 0.279 g (2 mmol) of ethyl glycinate and 0.70 ml (5 mmol) of triethylamine are added. After stirring at ambient temperature for 2 hours, the reaction medium is hydrolysed with water. After an overnight period at ambient temperature, the aqueous phase is extracted with dichloromethane. The organic phase obtained is washed with a saturated aqueous solution of sodium chloride, dried over sodium sulphate, filtered, and then concentrated under reduced pressure. The solid obtained is purified by silica gel column chromatography, elution being carried out with a dichloromethane/methanol (95/5) mixture. 0.362 g of a yellow solid is obtained.

Melting point: 221° C.
MH+=498

Sodium salt of {6-[(1-methoxy-2-phenylindolizin-3-yl)carbonyl]-2,4-dioxo-1,4-dihydroquinazolin-3(2H)-yl}acetic acid 0.75 ml (0.75 mmol) of a 1N aqueous solution of sodium hydroxide is added, at ambient temperature, to 0.312 mg (0.63 mmol) of ethyl {6-[(1-methoxy-2-phenylindolizin-3-yl)carbonyl]-2,4-dioxo-1,4-dihydroquinazolin-3(2H)-yl}acetate in 10 ml of methanol. The reaction medium is refluxed for 7 hours.

The reaction medium is acidified with a 1N aqueous solution of hydrochloric acid. The precipitate obtained is filtered off, rinsed with water, and dried under reduced pressure at 50° C. overnight.

0.52 ml (0.52 mmol) of a 1N aqueous solution of sodium hydroxide is added, at ambient temperature, to 0.250 g (0.53 mmol) of the solid obtained. The reaction medium is stirred for one hour and then diisopropyl ether is added. The precipitate obtained is filtered off, rinsed with diisopropyl ether, and then dried under reduced pressure at 50° C. overnight. 0.237 g of a yellow solid is obtained.

Melting point: 337° C.
MH+: 470
$^1$H-NMR (D6-DMSO, 400 MHz) δ ppm:
3.64 (s, 3H), 4.07 (s, 2H), 6.70 (d, J=8.55 Hz, 1H), 7.00-7.1 (m, 6H), 7.21-7.27 (m, 1H), 7.49 (d, J=8.37 Hz, 1H), 7.76 (d, J=9.07 Hz, 1H), 7.88 (d, J=1.92 Hz, 1H), 9.55 (d, J=7.15 Hz, 1H), 11.27 (s, 1H).

EXAMPLE 6

Compound No. 34

Ethyl({6-[(1-methoxy-2-methylindolizin-3-yl)carbonyl]-2,4-dioxo-1,4-dihydroquinazolin-3(2H)-yl}oxy)acetate Methyl 5-[(1-methoxy-2-methylindolizin-3-yl)carbonyl]-2-{[(prop-2-en-1-yloxy)-carbamoyl]amino}benzoate 0.251 g (0.83 mmol) of triphosgene diluted in 3 ml of dioxane is added, under an inert atmosphere at ambient temperature, to 0.4 g (1.18 mmol) of methyl 2-amino-5-[(1-methoxy-2-methylindolizin-3-yl)carbonyl]benzoate in 10 ml of dioxane. After stirring for 2.5 hours, 0.267 g (2.36 mmol) of O-prop-2-en-1-ylhydroxylamine and 0.82 ml (5.91 mmol) of triethylamine are added. The reaction medium is stirred for one hour and then hydrolysed with water. The aqueous phase is extracted with dichloromethane. The organic phase obtained is washed with a 1N aqueous solution of hydrochloric acid and a saturated aqueous solution of sodium chloride, and then dried over sodium sulphate, filtered, and concentrated under reduced pressure. 0.581 g of a yellow solid is obtained.

MH+: 438

6-[(1-Methoxy-2-methylindolizin-3-yl)carbonyl]-3-(prop-2-en-1-yloxy)-quinazoline-2,4(1H,3H)-dione 1.27 ml (1.27 mmol) of a 1N aqueous solution of sodium hydroxide are added, at ambient temperature, to 0.370 mg (0.85 mmol) of methyl 5-[(1-methoxy-2-methylindolizin-3-yl)carbonyl]-2-{[(prop-2-en-1-yloxy)carbamoyl]amino}benzoate in 5 ml of methanol. The reaction medium is refluxed for 1 hour.

The reaction medium is acidified with a 1N aqueous solution of hydrochloric acid.

The aqueous phase is extracted with ethyl acetate. The organic phase is washed with a saturated aqueous solution of sodium chloride, dried over sodium sulphate, filtered, and concentrated under reduced pressure. The solid obtained is purified by silica gel column chromatography, elution being carried out with dichloromethane. 0.293 g of a yellow solid is obtained.

Melting point: 258° C.
MH+: 406

3-Hydroxy-6-[(1-methoxy-2-methylindolizin-3-yl)carbonyl]quinazoline-2,4(1H,3H)-dione 0.15 ml (1.18 mmol) of phenylsilane and 0.030 g (0.03 mmol) of tetrakis(triphenylphosphine)palladium are added, under an inert atmosphere at 0° C., to 0.276 g (0.65 mmol) of 6-[(1-methoxy-2-methylindolizin-3-yl)carbonyl]-3-(prop-2-en-1-yloxy)-quinazoline-2,4(1H,3H)-dione in 7 ml of dichloromethane. The reaction medium is stirred for 4 hours at ambient temperature and then filtered. The precipitate is rinsed with dichloromethane. The solid is taken up in a 1N aqueous solution of sodium hydroxide.

After the addition of a 1N aqueous solution of hydrochloric acid, the precipitate obtained is filtered off, rinsed with water, and dried under reduced pressure overnight at 50° C. 0.208 mg of a yellow solid is obtained.

Melting point: 300° C.
MH+: 366

Ethyl({6-[(1-methoxy-2-methylindolizin-3-yl)carbonyl]-2,4-dioxo-1,4-dihydroquinazolin-3(2H)-yl}oxy)acetate 0.11 ml (0.99 mmol) of ethyl bromoacetate and then 0.14 ml (0.99 mmol) of triethylamine are added, at ambient temperature under an inert atmosphere, to 0.36 g (0.99 mmol) of 3-hydroxy-6-[(1-methoxy-2-methylindolizin-3-yl)carbonyl]quinazoline-2,4(1H,3H)-dione in 12.5 ml of ethanol. The reaction medium is stirred for 18 hours and then 0.14 ml (0.99 mmol) of triethylamine and 0.11 ml (0.99 mmol) of ethyl bromoacetate are added. After stirring for 18 hours at ambient temperature, the reaction medium is concentrated under reduced pressure. The residue obtained is purified by silica gel column chromatography, elution being carried out with a dichloromethane/methanol mixture. 217 mg of a yellow powder are obtained.

MH+=452
Melting point=230° C.
$^1$H-NMR (D6-DMSO, 400 MHz) δ ppm:
1.05-1.25 (t, 3H), 1.82 (s, 3H), 3.64 (s, 3H), 4.16-4.22 (q, 2H), 4.77 (s, 2H), 6.97-6.97 (t, 1H), 7.20-7.24 (t, 1H), 7.28-7.30 (d, 1H), 7.65-7.67 (d, 1H), 7.88-7.91 (d, 1H), 8.08 (s, 1H), 9.52-9.54 (d, 1H), 11.9 (s, 1H).

EXAMPLE 7

Compound No. 51

3-Amino-6-[(1-methoxy-2-methylindolizin-3yl)carbonyl]quinazoline-2,4(1H,3H)-dione 0.123 g (0.41 mmol) of triphosgene is added, under an inert atmosphere at ambient temperature, to 0.2 g (0.6 mmol) of methyl 2-amino-5-[(1-methoxy-2-methylindolizin-3-yl)carbonyl]benzoate in 10 ml of dioxane. After stirring for 10 minutes, 58 μl (1.2 mmol) of hydrazine hydrate and 0.4 ml (3 mmol) of triethylamine are added. The reaction medium is stirred for 3 hours and then hydrolysed with water. The aqueous phase is extracted with ethyl acetate. The organic phase obtained is dried over sodium sulphate, filtered, and then concentrated under reduced pressure. The solid obtained is purified by silica gel column chromatography, elution being carried out with a dichloromethane/methanol (95/5) mixture. 16 mg of a yellow solid are obtained.

Melting point: 220° C.
MH+=365
$^1$H-NMR (D6-DMSO, 400 MHz) δ ppm:
1.81 (s, 3H), 3.82 (s, 3H), 5.52 (s, 2H), 6.95 (t, J=6.95 Hz, 1H), 7.18-7.24 (m, 1H), 7.31 (d, J=8.69 Hz, 1H), 7.66 (d, J=8.69 Hz, 1H), 7.88 (d, J=8.69 Hz, 1H), 8.09 (d, J=2.09 Hz, 1H), 9.52 (d, J=6.95 Hz, 1H), 1.90 (s, 1H).

EXAMPLE 8

Compound No. 15

6-[(1-Methoxy-2-methylindolizin-3-yl)carbonyl]-2-methylquinazolin-4(3H)-one

6-[(1-Methoxy-2-methylindolizin-3-yl)carbonyl]-2-methyl-4H-3,1-benzoxazin-4-one 0.100 g (0.31 mmol) of 2-amino-5-[(1-methoxy-2-methylindolizin-3-yl)-carbonyl]benzoic acid (Example 150 described in WO 03/084956) in 1 ml of acetic anhydride is refluxed for 3 hours. The reaction medium is concentrated under reduced pressure. 0.107 g of a yellow solid is obtained.

Melting point: 218° C.

6-[(1-Methoxy-2-methylindolizin-3-yl)carbonyl]-2-methylquinazolin-4(3H)-one 0.100 g (0.29 mmol) of 6-[(1-methoxy-2-methylindolizin-3-yl)carbonyl]-2-methyl-4H-3,1-benzoxazin-4-one in 2 ml of a 20% aqueous ammonia solution are heated for 2 hours at 50° C. and then hydrolysed with 3 ml of 10% aqueous sodium hydroxide solution and brought to 50° C. for 2 hours. The reaction medium is acidified with a 1N aqueous solution of hydrochloric acid, to pH=9. The precipitate obtained is filtered off, rinsed with water and then dried under reduced pressure at 40° C. overnight. The solid obtained is purified by silica gel column chromatography, elution being carried out with a dichloromethane/methanol (90/10) mixture. 67 mg of a yellow solid are obtained.

Melting point: 290° C.
MH+: 348
$^1$H-NMR (D6-DMSO, 400 MHz) δ ppm:
1.75 (s, 3H), 2.39 (s, 3H), 3.82 (s, 3H), 6.98 (t, J=7.07 Hz, 1H), 7.22-7.27 (m, 1H), 7.66-7.70 (m, 2H), 7.94 (d, J=8.19 Hz, 1H), 8.20 (d, J=2.23 Hz, 1H), 9.61 (d, J=7.07 Hz, 1H), 12.39 (s, 1H).

EXAMPLE 9

Compound No. 43

Sodium salt of 3-{(2-methyl-3-[(2-methyl-4-oxo-3,4-dihydroquinazolin-6-yl)-carbonyl]indolizin-1-yl}benzoic acid

2-Amino-5-[(1-bromo-2-methylindolizin-3-yl)carbonyl]benzoic acid 4.92 ml (4.92 mmol) of a 1N aqueous solution of sodium hydroxide are added, at ambient temperature, to 1.91 g (4.69 mmol) of methyl 2-amino-5-[(1-bromo-2-methylindolizin-3-yl)carbonyl]benzoate in 30 ml of methanol. The reaction medium is refluxed for 10 hours and then hydrolysed with a 1N aqueous solution of hydrochloric acid. The aqueous phase is extracted with ethyl acetate. The organic phase obtained is washed with water, dried over sodium sulphate, filtered, and concentrated under reduced pressure. The solid obtained is rinsed with diisopropyl ether and dichloromethane, and dried under reduced pressure overnight at 50° C. 1.55 g of a yellow solid are obtained.

MH+: 374
Melting point: 230° C.

6-[(1-Bromo-2-methylindolizin-3-yl)carbonyl]-2-methylquinazolin-4(3H)-one 0.450 g (1.15 mmol) of 2-amino-5-[(1-bromo-2-methylindolizin-3-yl)carbonyl]-benzoic acid in 3.79 ml of acetic anhydride are refluxed for 1.5 hours under an inert atmosphere. The reaction medium is concentrated under reduced pressure.

0.457 g (1.15 mmol) of the solid obtained in 8 ml of a 0.5N aqueous solution of ammonia in dioxane are heated at 50° C. for 1 hour. After the addition of diisopropyl ether, the precipitate formed is filtered off, rinsed with water, and then dried under reduced pressure at 50° C. overnight 182 mg of a yellow solid are obtained.

MH+: 348

Methyl 3-{2-methyl-3-[(2-methyl-4-oxo-3,4-dihydroquinazolin-6-yl)-carbonyl]indolizin-1-yl}benzoate 0.139 g (0.78 mmol) of [3-(methoxycarbonyl)phenyl]boronic acid, 0.321 g (1.29 mmol) of potassium phosphate dihydrate dissolved in 0.81 ml of water, and 0.0149 g (0.01 mmol) of tetrakis(triphenylphosphine)palladium are added, under an argon atmosphere at ambient temperature, to 0.256 g (0.65 mmol) of 6-[(1-bromo-2-methylindolizin-3-yl)carbonyl]-2-methylquinazolin-4(3H)-one in 9 ml of DMF. The reaction medium is microwave-heated at 150° C. for 15 minutes. After dilution with ethyl acetate, the organic phase is washed with a 1N aqueous solution of hydrochloric acid and then a saturated aqueous solution of sodium chloride, dried over sodium sulphate, filtered, and then concentrated under reduced pressure. The solid obtained is purified by silica gel column chromatography, elution being carried out with a dichloromethane/methanol (95/2) mixture. 172 mg of a yellow solid are obtained.

Melting point: 232° C.
MH+: 452

Sodium salt of 3-{2-methyl-3-[(2-methyl-4-oxo-3,4-dihydroquinazolin-6-yl)carbonyl]indolizin-1-yl}benzoic acid 0.45 ml (0.45 mmol) of a 1N aqueous solution of sodium hydroxide is added, at ambient temperature, to 0.171 g (0.38 mmol) of methyl 3-{2-methyl-3-[(2-methyl-4-oxo-3,4-dihydroquinazolin-6-yl)carbonyl]indolizin-1-yl}benzoate in 4 ml of methanol. The reaction medium is refluxed for 10 hours and then hydrolysed with a 1N aqueous solution of hydrochloric acid. The aqueous phase is extracted with ethyl acetate. The organic phase obtained is washed with water, dried over sodium sulphate, filtered, and concentrated under reduced pressure. The solid obtained is rinsed with water and then dried under reduced pressure overnight at 50° C. 0.12 ml (0.12 mmol) of a 1N aqueous solution of sodium hydroxide is added, at ambient temperature, to 0.056 g of the solid obtained, in 4 ml of methanol. The reaction medium is stirred for one hour and then diisopropyl ether is added. The precipitate obtained is filtered off, rinsed with diisopropyl ether, and then dried under reduced pressure at 50° C. overnight. 58 mg of a yellow solid are obtained.

Melting point: 344° C.
MH+: 438
$^1$H-NMR (D6-DMSO, 400 MHz) δ ppm:
1.83 (s, 3H), 2.40 (s, 3H), 7.04 (t, J=6.70 Hz, 1H), 7.25-7.44 (m, 3H), 7.55 (d, J=8.04 Hz, 1H), 7.70 (d, J=8.71 Hz, 1H), 7.85 (d, J=6.70 Hz, 1H), 7.92 (s, 1H), 8.04 (d, J=8.04 Hz, 1H), 8.31 (s, 1H), 9.59 (d, J=6.70 Hz, 1H), 12.53 (s, 1H).

EXAMPLE 10

Compound No. 48

6-{[1(2-Methoxyethoxy)-2-methylindolizin-3-yl]carbonyl}-3-propylquinazoline-2,4(1H,3H)-dione Methyl 2-amino-5-[(1-hydroxy-2-methylindolizin-3-yl)carbonyl]benzoate 0.365 mg (5.79 mmol) of ammonium formate and 0.102 g (0.1 mmol) of palladium-on-carbon (10%) are added, at ambient temperature under an inert atmosphere, to 0.8 g (1.93 mmol) of methyl 2-amino-5-{[1-(benzyloxy)-2-methylindolizin-3-yl]carbonyl}benzoate in 30 ml of DMF. The reaction medium is stirred for 3 hours at ambient temperature and then filtered. The palladium is rinsed with ethyl acetate. The organic phase is washed with water, dried over sodium sulphate, filtered, and concentrated under reduced pressure. A green oil is obtained.

MH+: 325

Methyl 2-amino-5-{[1-(2-methoxyethoxy)-2-methylindolizin-3-yl]carbonyl}-benzoate 0.161 g (1.16 mmol) of 1-bromo-2-methoxyethane and 0.359 mg (1.16 mmol) of caesium carbonate are added, under an inert atmosphere at ambient temperature, to 0.313 g (0.97 mmol) of methyl 2-amino-5-{[1-hydroxy-2-methylindolizin-3-yl]-carbonyl}benzoate in 10 ml of DMF. The reaction medium is stirred for 24 hours at ambient temperature, hydrolysed with water, and then acidified with a 1N aqueous solution of hydrochloric acid. The aqueous phase is extracted with ethyl acetate. The organic phase obtained is washed with a saturated aqueous solution of sodium chloride, dried over sodium sulphate, filtered, and then concentrated under reduced pressure. The solid obtained is purified by silica gel column chromatography, elution being carried out with a dichloromethane/methanol (95/5) mixture. 150 mg of a yellow oil are obtained.

MH+: 383

Methyl 5-{[1-(2-methoxyethoxy)-2-methylindolizin-3-yl]carbonyl}-2-[(propylcarbamoyl)amino]benzoate 0.108 g (0.37 mmol) of triphosgene diluted in 1 ml of dioxane is added, under an inert atmosphere at ambient temperature, to 0.2 g (0.52 mmol) of methyl 2-amino-5-{[1-(2-methoxyethoxy)-2-methylindolizin-3-yl]carbonyl}benzoate in 5 ml of dioxane. The reaction medium is stirred for 1 hour at ambient temperature and then 0.22 ml (1.57 mmol) of triethylamine and 0.09 ml (1.05 mmol) of n-propylamine are added. After stirring for 18 hours, the reaction medium is hydrolysed with water. The aqueous phase is extracted with dichloromethane. The organic phase obtained is dried over sodium sulphate, filtered, and concentrated under reduced pressure. The solid obtained is purified by silica gel column chromatography, elution being carried out with a dichloromethane/methanol (95/5) mixture. 170 mg of a yellow solid are obtained.
Melting point: 125° C.
MH+: 468

6-{[1(2-Methoxyethoxy)-2-methylindolizin-3-yl]carbonyl}-3-propylquinazoline-2,4(1H,3H)-dione 0.44 ml (0.44 mmol) of a 1N aqueous solution of sodium hydroxide is added, at ambient temperature, to 0.17 g (0.36 mmol) of methyl 5-{[1-(2-methoxyethoxy)-2-methylindolizin-3-yl]carbonyl}-2-[(propylcarbamoyl)amino]benzoate in 5 ml of methanol. The reaction medium is refluxed for 7 hours.

The reaction medium is acidified with a 1N aqueous solution of hydrochloric acid. The precipitate obtained is filtered off, rinsed with water, and dried under reduced pressure at 50° C. overnight.

79 mg of a yellow solid are obtained.
Melting point: 215° C.
MH+: 436
$^1$H-NMR (D6-DMSO, 400 MHz) δ ppm:
0.89 (t, J=7.17 Hz, 3H), 1.55-1.67 (m, 2H), 1.82 (s, 3H), 3.31 (s, 3H), 3.56-3.61 (m, 2H), 3.83-3.90 (m, 2H), 4.05-4.10 (m, 2H), 6.95 (t, J=7.17 Hz, 1H), 7.19-7.24 (m, 1H), 7.27 (d, J=8.44 Hz, 1H), 7.63 (d, J=8.86 Hz, 1H), 7.87 (d, J=8.44 Hz, 1H), 8.10 (d, J=2.11 Hz, 1H), 9.51 (d, J=7.17 Hz, 1H), 1.7 (s, 1H).

EXAMPLE 11

Compound No. 62

Sodium salt of 6-[(1-methoxy-2-methylindolizin-3-yl)carbonyl]-1-methyl-4-oxo-1,4-dihydroquinoline-3-carboxylic acid (1-Methoxy-2-methylindolizin-3-yl)(4-nitrophenyl)methanone 1.8 ml (12.92 mmol) of triethylamine are added, at ambient temperature under an inert atmosphere, to 1.7 g (10.77 mmol) of 1-methoxy-2-methylindolizine in 15 ml of dichloroethane, followed, dropwise, by 2.2 g (11.85 mmol) of 4-nitrobenzoic acid chloride. The reaction medium is stirred for 30 minutes at ambient temperature, hydrolysed with a saturated aqueous solution of sodium hydrogen carbonate and then extracted with dichloromethane. The organic phase is washed with a saturated aqueous solution of sodium chloride, dried over sodium sulphate, and then concentrated under reduced pressure. The residue obtained is washed with diethyl ether. 3 g of an orange solid are obtained.
MH+: 311
Melting point: 151° C.

(4-Aminophenyl)(1-methoxy-2-methylindolizin-3-yl)methanone 1.93 g (34.46 mmol) of iron and 8.21 ml (143.57 mmol) of glacial acetic acid are added to 2.97 g (9.57 mmol) of (1-methoxy-2-methylindolizin-3-yl)(4-nitrophenyl)methanone in 120 ml of a 2/1 mixture of water and ethanol. The reaction medium is heated at 80° C. for 3 hours. The reaction medium is extracted with ethyl acetate. The organic phase is washed with a saturated aqueous solution of sodium hydrogen carbonate and then with a saturated aqueous solution of sodium chloride, dried over sodium sulphate, and then concentrated under reduced pressure. The residue obtained is purified by silica gel column chromatography, elution being carried out with a dichloromethane/methanol (90/10) mixture. 2.58 g of a yellow solid are obtained.
MH+: 281

Ethyl 6-[(1-methoxy-2-methylindolizin-3-yl)carbonyl]-4-oxo-1,4-dihydroquinoline-3-carboxylate 0.36 ml of diethyl ethoxymethylene malonate is added, under an inert atmosphere at ambient temperature, to 0.4 g (1.43 mmol) of (4-aminophenyl)(1-methoxy-2-methylindolizin-3-yl)methanone in 6 ml of toluene. The reaction medium is heated at 110° C. for 1 h 45 and then concentrated under reduced pressure. The residue obtained is dissolved in 8.2 ml of diphenyl ether and then heated at 230° C. for 1 h 20. After the addition of diisopropyl ether and pentane at ambient temperature, the precipitate formed is filtered off and rinsed with pentane. The residue obtained is purified by silica gel column chromatography, elution being carried out with a dichloromethane/methanol (90/10) mixture. 142 mg of a yellow powder are obtained.
Melting point: 271° C.
MH+: 405

Ethyl 6-[(1-methoxy-2-methylindolizin-3-yl)carbonyl]-1-methyl-4-oxo-1,4-dihydroquinoline-3-carboxylate 3.8 g (27.89 mmol) of potassium carbonate and 1.74 ml (27.89 mmol) of methyl iodide are added, at ambient temperature under an inert atmosphere, to 10 g (23.24 mmol) of ethyl 6-[(1-methoxy-2-methylindolizin-3-yl)carbonyl]-4-oxo-1,4-dihydroquinoline-3-carboxylate in 100 ml of DMF. The reaction medium is heated at 90° C. for 1 h 30. The reaction medium is filtered through talc, diluted with dichloromethane, and then washed with water. The organic phase is dried with sodium sulphate and then concentrated under reduced pressure. The residue obtained is purified by silica gel column chromatography, elution being carried out with a dichloromethane/methanol (90/10) mixture. 9.1 g of a yellow solid are obtained.
Melting point: 258° C.
MH+: 419

Sodium salt of 6-[(1-methoxy-2-methylindolizin-3-yl)carbonyl]-1-methyl-4-oxo-1,4-dihydroquinoline-3-carboxylic acid 0.34 ml (0.34 mmol) of a 1N aqueous solution of sodium hydroxide is added, at ambient temperature, to 0.348 g (0.83 mmol) of ethyl 6-[(1-methoxy-2-methylindolizin-3-yl)carbonyl]-1-methyl-4-oxo-1,4-dihydroquinoline-3-carboxylate in a 4 ml mixture of t-butanol and water (1/1). The reaction medium is refluxed for 2 hours.

The reaction medium is acidified with a 1N aqueous solution of hydrochloric acid. The precipitate obtained is purified by silica gel column chromatography, elution being carried out with a dichloromethane/methanol (95/5) mixture.

0.56 ml (0.56 mmol) of a 1N aqueous solution of sodium hydroxide is added to 0.231 g of the solid obtained, in 4 ml of methanol. The reaction medium is stirred for one hour and then diethyl ether is added. The precipitate obtained is filtered off, rinsed with diethyl ether and then dried under reduced pressure at 50° C. overnight. 265 mg of a yellow solid are obtained.
Melting point 258° C.
MH+: 391
$^1$H-NMR (D6-DMSO, 400 MHz) δ ppm:
1.75 (s, 3H), 3.8 (s, 3H), 3.96 (s, 3H), 6.96 (t, J=6.43 Hz, 1H), 7.22 (t, J=6.89 Hz, 1H), 7.66 (d, J=8.72 Hz, 1H), 7.82 (d, J=8.27 Hz, 1H), 7.96 (d, J=8.27 Hz, 1H), 8.45 (s, 1H), 8.69 (s, 1H), 9.57 (d, J=7.35 Hz, 1H).

EXAMPLE 12

Compound No. 73

Sodium salt of 6-[(1-methoxy-2-methylindolizin-3-yl)carbonyl]-2-methyl-4-oxo-1,4-dihydroquinoline-3-carboxylic acid 6-[(1-Methoxy-2-methylindolizin-3-yl)carbonyl]-1-prop-2-en-1-yl-2H-3,1-benzoxazine-2,4(1H)-dione 0.5 ml (5.71 mmol) of allyl bromide and 0.19 g (4.28 mmol) of sodium hydride at 60% are added, under an inert atmosphere at ambient temperature, to 1 g (2.85 mmol) of 6-[(1-methoxy-2-methylindolizin-3-yl)carbonyl]-2H-3,1-benzoxazine-2,4(1H)-dione in 15 ml of DMF. The reaction medium is stirred for 2 hours at ambient temperature and then concentrated under reduced pressure. After the addition of ice to the residue, the precipitate formed is filtered off, rinsed with water, and dried under reduced pressure at 50° C. overnight. 0.773 g of a yellow solid is obtained.
MH+: 391

Ethyl 6-[(1-methoxy-2-methylindolizin-3-yl)carbonyl]-2-methyl-4-oxo-1-prop-2-en-1-yl-1,4-dihydroquinoline-3-carboxylate 0.49 ml (3.80 mmol) of ethyl acetoacetate diluted in 20 ml of anhydrous DMF is added, under an inert atmosphere at ambient temperature, to 0.66 g (1.52 mmol) of 6-[(1-methoxy-2-methylindolizin-3-yl)carbonyl]-1-prop-2-en-1-yl-2H-3,1-benzoxazine-2,4(1H)-dione in 30 ml of DMF. The reaction medium is stirred at ambient temperature overnight and then extracted with ethyl acetate. The organic phase obtained is washed with a saturated aqueous solution of sodium chloride, dried over sodium sulphate, filtered, and then concentrated under reduced pressure.
The residue obtained is purified by silica gel column chromatography, elution being carried out with a dichloromethane/methanol (95/5) mixture. 0.441 g of a yellow solid is obtained.
Melting point: 101° C.
MH+: 459

Ethyl 6-[(1-methoxy-2-methylindolizin-3-yl)carbonyl]-2-methyl-4-oxo-1,4-dihydroquinoline-3-carboxylate 6.7 mg (0.02 mmol) of dichloro(2,6,10-dodecatriene)-1,12-diyl ruthenium(IV) are added, at ambient temperature under an inert atmosphere, to 0.307 (0.67 mol) of ethyl 6-[(1-methoxy-2-methylindolizin-3-yl)carbonyl]-2-methyl-4-oxo-1-prop-2-en-1-yl-1,4-dihydroquinoline-3-carboxylate in 12 ml of a mixture of DMFt-butanol and water (1/1). The reaction medium is microwave-heated for 30 minutes at 120° C. and then extracted with ethyl acetate. The organic phase obtained is washed with a saturated aqueous solution of sodium chloride, dried over sodium sulphate, filtered, and concentrated under reduced pressure. The precipitate obtained is purified by silica gel column chromatography, elution being carried out with a dichloromethane/methanol (95/5) mixture. 94 mg of a yellow solid are obtained.
Melting point: 257° C.
MH+: 419

سodium salt of 6-[(1-methoxy-2-methylindolizin-3-yl)carbonyl]-2-methyl-4-oxo-1,4-dihydroquinoline-3-carboxylic acid 0.32 ml (0.32 mmol) of a 1N aqueous solution of sodium hydroxide is added, at ambient temperature, to 0.066 g (0.16 mmol) of ethyl 6-[(1-methoxy-2-methylindolizin-3-yl)carbonyl]-2-methyl-4-oxo-1,4-dihydroquinoline-3-carboxylate in 4 ml of ethanol. The reaction medium is refluxed for 2 hours.
The reaction medium is acidified with a 1N aqueous solution of hydrochloric acid. The precipitate obtained is purified by silica gel column chromatography, elution being carried out with a dichloromethane/methanol (95/5) mixture.
0.04 ml (0.04 mmol) of a 1N aqueous solution of sodium hydroxide is added to 0.019 g of the solid obtained, in 2 ml of methanol. The reaction medium is stirred for one hour and then diethyl ether is added. The precipitate obtained is filtered off, rinsed with diethyl ether and then dried under reduced pressure at 50° C. overnight. 16 mg of a yellow solid are obtained.
MH+: 391
$^1$H-NMR (D6-DMSO, 400 MHz) δ ppm:
1.79 (s, 3H), 2.76 (s, 3H), 3.83 (s, 3H), 6.91 (t, J=6.28 Hz, 1H), 7.17 (t, J=7.70 Hz, 1H), 7.61-7.77 (m, 3H), 8.31 (s, 1H), 9.50 (d, J=6.56 Hz, 1H).

EXAMPLE 13

Compound No. 96

6-[(1-Methoxy-2-methylindolizin-3-yl)carbonyl]-N-methyl-4-oxo-1,4-dihydroquinoline-3-carboxamide 6-[(1-Methoxy-2-methylindolizin-3-yl)carbonyl]-4-oxo-1,4-dihydroquinoline-3-carboxylic acid 3.07 ml (37.09 mmol) of a 1N aqueous solution of sodium hydroxide are added, at ambient temperature, to 3 g (7.42 mmol) of ethyl 6-[(1-methoxy-2-methylindolizin-3-yl)carbonyl]-4-oxo-1,4-dihydroquinoline-3-carboxylate in 36 ml of a mixture of t-butanol and water (1/1). The reaction medium is refluxed for 2 hours.
The reaction medium is acidified with a 1N aqueous solution of hydrochloric acid. The precipitate obtained is rinsed with ethyl acetate, with methanol and then with water, and dried under reduced pressure overnight at 50° C. 1.8 g of a yellow-green solid are obtained.
At the same time, the organic phase is washed with a saturated solution of sodium chloride, dried over sodium sulphate, and concentrated under reduced pressure. The residue obtained is rinsed with ether, and dried under reduced pressure overnight at 50° C. 0.85 g of a yellow solid is obtained.
Melting point: 289° C.
MH+: 377

6-[(1-Methoxy-2-methylindolizin-3-yl)carbonyl]-N-methyl-4-oxo-1,4-dihydroquinoline-3-carboxamide 0.36 g (5.31 mmol) of methylamine hydrochloride, 1.3 g (3.99 mmol) of TOTU and 1.37 g (10.63 mmol) of DIEA are added to 1 g (2.66 mmol) of 6-[(1-methoxy-2-methylindolizin-3-yl)carbonyl]-4-oxo-1,4-dihydroquinoline-3-carboxylic acid in 23 ml of anhydrous DMF. The reaction medium is stirred at ambient temperature under a nitrogen atmosphere for 8 h. 0.36 g (5.33 mmol) of methylamine hydrochloride is added to the reaction medium. After 18 h at ambient temperature, the reaction medium is hydrolysed with a 1N solution of HCl and then extracted with ethyl acetate. The organic phase is washed with a saturated solution of sodium chloride, dried over sodium sulphate, and then concentrated under reduced pressure. The residue obtained is purified by silica gel column chromatography, elution being carried out with a dichloromethane/methanol (90/10) mixture. 0.06 g of a yellow solid is obtained.

Melting point: 324° C.
MH+=390
¹H-NMR (D6-DMSO, 400 MHz) δ ppm:
1.75 (s, 3 H) 2.86 (d, J=4.8 Hz, 3 H) 3.82 (s, 3 H) 6.99 (td, J=6.9, 1.3 Hz, 1 H) 7.25 (ddd, J=8.8, 6.8, 0.9 Hz, 1 H) 7.68 (d, J=8.8 Hz, 1 H) 7.81 (d, J=8.5 Hz, 1 H) 7.96 (dd, J=8.6, 2.0 Hz, 1 H) 8.40 (d, J=1.9 Hz, 1 H) 8.80 (s, 1 H) 9.61 (d, J=7.1 Hz, 1 H) 9.70-9.82 (m, 1 H) 12.88 (br. s., 1 H).

EXAMPLE 14

Compound No. 105

N-1-Dimethyl-6-[(2-methylindolizin-3-yl)carbonyl]-4-oxo-1,4-dihydroquinoline-3-carboxamide (2-Methylindolizin-3-yl)(4-nitrophenyl)methanone 4.54 ml (32.52 mmol) of triethylamine are added, at ambient temperature under an inert atmosphere, to 3.56 g (27.14 mmoles) of 2-methylindolizine in 15 ml of dichloroethane, followed, dropwise, by 5.53 g (29.85 mmol) of 4-nitrobenzoic acid chloride. The reaction medium is stirred for 18 h at ambient temperature, hydrolysed with a saturated aqueous solution of sodium hydrogen carbonate and then extracted with dichloromethane. The organic phase is washed with a saturated aqueous solution of sodium chloride, dried over sodium sulphate, and then concentrated under reduced pressure. The residue obtained is washed with diethyl ether. 5.69 g of a yellow solid are obtained.
MH+: 281
Melting point: 149° C.

(4-Aminophenyl)(2-methylindolizin-3-yl)methanone 5.66 g (86.57 mmol) of zinc and 20.63 ml (360.71 mmol) of glacial acetic acid are added to 6.74 g (24.05 mmol) of (2-methylindolizin-3-yl)(4-nitrophenyl)methanone in 120 ml of a 2/1 mixture of water and ethanol. The reaction medium is heated at 80° C. for 4 hours. 0.57 g (8.7 mmol) of zinc and 2.06 ml of glacial acetic acid are added. Refluxing is maintained for 1 hour. At ambient temperature, the reaction medium is filtered off. The residue obtained is rinsed with ethyl acetate and with methyl THF. The organic phase is washed with a saturated aqueous solution of sodium hydrogen carbonate and then with a saturated aqueous solution of sodium chloride, dried over sodium sulphate, and then concentrated under reduced pressure. The residue obtained is purified by silica gel column chromatography, elution being carried out with a dichloromethane/methanol (90/10) mixture. 4.9 g of a yellow solid are obtained.
MH+: 251
Melting point: 186° C.

Ethyl 6-[(2-methylindolizin-3-yl)carbonyl]-4-oxo-1,4-dihydroquinoline-3-carboxylate 1.69 ml of diethyl ethoxymethylene malonate are added, under an inert atmosphere at ambient temperature, to 1.83 g (6.8 mmol) of (4-aminophenyl)(2-methylindolizin-3-yl) methanone in 23 ml of toluene. The reaction medium is heated at 110° C. for 1 h 45 and then concentrated under reduced pressure. The residue obtained is dissolved in 45 ml of diphenyl ether and then heated at 230° C. for 30 minutes. After the addition of diisopropyl ether at ambient temperature, the precipitate formed is filtered off, rinsed with diisopropyl ether, with methanol and then with dichloromethane, and dried under reduced pressure at 50° C. overnight 1.2 g of a yellow powder are obtained.
MH+: 375
Melting point: 287° C.

Ethyl 6-[(2-methylindolizin-3-yl)carbonyl]-1-methyl-4-oxo-1,4-dihydroquinoline-3-carboxylate 1.53 g (11.12 mmol) of potassium carbonate and 0.69 ml (11.12 mmol) of methyl iodide are added, at ambient temperature under an inter atmosphere, to 3.73 g (9.27 mmol) of ethyl 6-[(2-methylindolizin-3-yl)carbonyl]-4-oxo-1,4-dihydroquinoline-3-carboxylate in 100 ml of DMF. The reaction medium is heated at 90° C. for 2 h. 0.384 g (2.78 mmol) of potassium carbonate and 0.173 ml (2.78 mmol) of methyl iodide are added and then the heating is continued for 40 minutes. The reaction medium is hydrolysed with water and then extracted with ethyl acetate and with dichloromethane. The organic phase is washed with a saturated solution of sodium chloride, dried over sodium sulphate, and then concentrated under reduced pressure. The residue obtained is purified by silica gel column chromatography, elution being carried out with a dichloromethane/methanol (90/10) mixture. 3.15 g of a yellow solid are obtained.
Melting point: 232° C.
MH+: 389

6-[(2-Methylindolizin-3-yl)carbonyl]-1-methyl-4-oxo-1,4-dihydroquinoline-3-carboxylic acid 0.27 ml (3.22 mmol) of a 1N aqueous solution of sodium hydroxide is added, at ambient temperature, to 0.5 g (1.29 mmol) of ethyl 6-[(2-methylindolizin-3-yl)carbonyl]-1-methyl-4-oxo-1,4-dihydroquinoline-3-carboxylate in 9 ml of a mixture of t-butanol and water (1/1). The reaction medium is refluxed for 1 hour, acidified with a 1N aqueous solution of hydrochloric acid at ambient temperature, and then extracted with dichloromethane. The organic phase is washed with water, dried over sodium sulphate, and concentrated under reduced pressure. The residue obtained is rinsed with ether and then dried under reduced pressure at 50° C. 448 mg of a yellow solid are obtained.
Melting point: 308° C.
MH+: 361

N-1-Dimethyl-6-[(2-methylindolizin-3-yl)carbonyl]-4-oxo-1,4-dihydroquinoline-3-carboxamide 0.16 g (2.44 mmol) of methylamine hydrochloride, 0.6 g (1.59 mmol) of HBTU and 0.74 ml (4.27 mmol) of DIEA are added to 0.44 g (1.22 mmol) of 6-[(2-methylindolizin-3-yl) carbonyl]-1-methyl-4-oxo-1,4-dihydroquinoline-3-carboxylic acid in 7 ml of anhydrous DMF. The reaction medium is stirred at ambient temperature under a nitrogen atmosphere for 5 h 30. 0.16 g (2.44 mmol) of methylamine hydrochloride, 602 mg (1.29 mmol) of HBTU and 0.74 ml (4.27 mmol) of DIEA are added to the reaction medium. After 48 h at ambient temperature, the reaction medium is hydrolysed with a saturated solution of sodium hydrogen carbonate and then extracted with dichloromethane. The organic phase is washed with a saturated solution of sodium chloride, dried over sodium sulphate, and then concentrated under reduced pressure. The residue obtained is purified by silica gel column chromatography, elution being carried out with a dichloromethane/methanol (90/10) mixture. 0.273 g of a yellow solid is obtained.
Melting point: 328° C.
MH+=374
¹H-NMR (D6-DMSO, 400 MHz) δ ppm:
1.85 (s, 3 H) 2.86 (d, J=4.8 Hz, 3 H) 4.08 (s, 3 H) 6.53 (s, 1 H) 7.01 (td, J=6.9, 1.3 Hz, 1 H) 7.24-7.33 (m, 1 H) 7.67 (d, J=8.8 Hz, 1 H) 7.96 (d, J=8.8 Hz, 1 H) 8.06 (dd, J=8.7, 2.1 Hz, 1 H) 8.48 (d, J=2.0 Hz, 1 H) 8.92 (s, 1 H) 9.61 (d, J=7.0 Hz, 1 H) 9.67-9.76 (m, 1 H).

EXAMPLE 15

Compound No. 106

N-1-Dimethyl-6-{[2-methyl-1-(pyridin-4-yl)indolizin-3-yl]carbonyl}-4-oxo-1,4-dihydroquinoline-3-carboxamide hydrochloride 6-[(1-Bromo-2-methylindolizin-3-yl)carbonyl]-N-1-dimethyl-4-oxo-1,4-dihydroquinoline-3-carboxamide 0.108 mg (0.6 mmol) of N-bromosuccinimide is added, at ambient temperature under a nitrogen atmosphere, to 0.188 g (0.5 mmol) of N-1-dimethyl-6-[(2-methylindolizin-3-yl)carbonyl]-4-oxo-1,4-dihydroquinoline-3-carboxamide in 6 ml of dichloromethane. After stirring for 3 h at ambient temperature, the reaction medium is hydrolysed with a saturated solution of sodium hydrogen carbonate and then extracted with dichloromethane. The organic phase is washed with a saturated solution of sodium chloride, dried over sodium sulphate, and then concentrated under reduced pressure. The residue obtained is purified by silica gel column chromatography, elution being carried out with a dichloromethane/methanol (90/10) mixture. 0.217 g of a yellow solid is obtained.

MH+=453

N-1-Dimethyl-6-{[2-methyl-1-(pyridin-4-yl)indolizin-3-yl]carbonyl}-4-oxo-1,4-dihydroquinoline-3-carboxamide 0.061 g (0.29 mmol) of 4-(4,4,5,5-tetramethyl-1,3,2-dioxaborolan-2-yl)pyridine, 0.178 g (0.72 mmol) of potassium phosphate dihydrate and 0.0055 g (0.004 mmol) of tetrakis(triphenylphosphine)palladium are added, under an argon atmosphere at ambient temperature, to 0.108 g (0.24 mmol) of 6-[(1-bromo-2-methylindolizin-3-yl)carbonyl]-N-1-dimethyl-4-oxo-1,4-dihydroquinoline-3-carboxamide in 2.5 ml of DMF. The reaction medium is microwave-heated for 15 minutes at 150° C. The reaction medium is filtered through talc. The residue obtained is washed with dichloromethane and with methanol. The organic phase is concentrated under reduced pressure. The residue obtained is purified by silica gel column chromatography, elution being carried out with a dichloromethane/methanol (90/10) mixture. 53 mg of a yellow solid are obtained.

This solid is taken up in 2 ml of methanol. 0.16 ml (0.16 mmol) of a 1N solution of HCl is added at ambient temperature under a nitrogen atmosphere. After stirring for 5 minutes, ether is added. The precipitate obtained is filtered off, rinsed with ether, and then dried under reduced pressure at 50° C. overnight. 55 mg of a yellow solid are obtained.

Melting point: 228° C.
MH+=451
$^{1}$H-NMR (D6-DMSO, 400 MHz) δ ppm:
1.99 (s, 3 H) 2.87 (d, J=4.7 Hz, 3 H) 4.09 (s, 3 H) 7.20 (t, J=6.5 Hz, 1 H) 7.48-7.55 (m, 1 H) 7.93 (d, J=9.0 Hz, 1 H) 7.99 (d, J=8.9 Hz, 1 H) 8.02 (d, J=5.6 Hz, 2 H) 8.19 (dd, J=8.8, 2.0 Hz, 1 H) 8.65 (d, J=2.0 Hz, 1 H) 8.83 (d, J=6.5 Hz, 2 H) 8.94 (s, 1 H) 9.46 (d, J=7.0 Hz, 1 H) 9.65-9.74 (m, 1 H).

The table which follows illustrates the chemical structures and the physical properties of some compounds according to the invention. In this table:
- Me and Et represent, respectively, methyl and ethyl groups;
- the wavy line represents the bond attached to the rest of the molecule;
- Mp represents the melting point of the compound, expressed in degrees Celsius;
- M+H$^+$ represents the mass of the compound, obtained by LC-MS (Liquid Chromatography-Mass Spectroscopy).

TABLE (I)

| No. | R$_1$ | R$_2$ | (R$_3$/R$_4$ aryl group) | Salt | Mp (° C.) | M+H$^+$ |
|---|---|---|---|---|---|---|
| 1 | —OMe | Me | 6-methyl-3-propyl-quinazoline-2,4-dione | / | 292 | 392 |
| 2 | —OMe | Me | 6-methyl-quinazoline-2,4-dione | / | 343 | 350 |

TABLE-continued
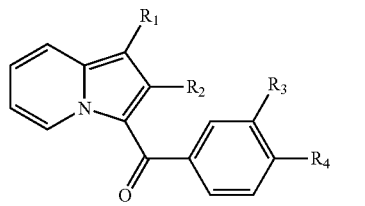
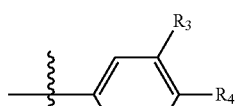
| No. | R₁ | R₂ | (Ar) | Salt | Mp (°C.) | M + H⁺ |
|---|---|---|---|---|---|---|
| 3 | —OMe | Me | 6-methylquinazolin-4(3H)-one | / | 285 | 334 |
| 4 | —OMe | Me | 3,6-dimethylquinazoline-2,4(1H,3H)-dione | / | 298 | 364 |
| 5 | —OMe | Me | 3-isopropyl-6-methylquinazoline-2,4(1H,3H)-dione | / | 277 | 392 |
| 6 | —OMe | Me | 6-methyl-3-(2-(piperidin-1-yl)ethyl)quinazoline-2,4(1H,3H)-dione | HCl | 268 | 461 |
| 7 | —OMe | Me | 3-(2-(dimethylamino)ethyl)-6-methylquinazoline-2,4(1H,3H)-dione | / | 260 | 421 |
| 8 | —OMe | Me | 6-methyl-3-(2-(pyrrolidin-1-yl)ethyl)quinazoline-2,4(1H,3H)-dione | HCl | 255 | 447 |

TABLE-continued
(I)
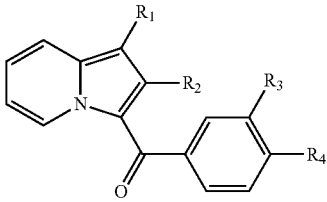
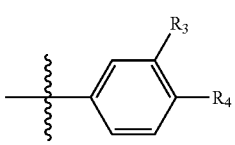
| No. | R₁ | R₂ | (structure) | Salt | Mp (°C.) | M + H⁺ |
|---|---|---|---|---|---|---|
| 9 | —OMe | Me | 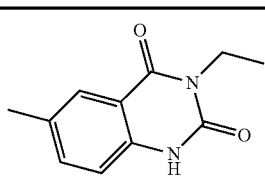 | / | 317 | 378 |
| 10 | —OMe | Me | 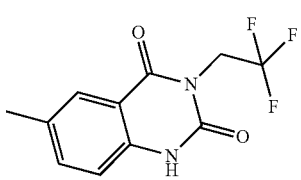 | / | 345 | 432 |
| 11 | —OMe | Me | 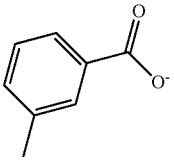 | Na | 351 | 408 |
| 13 | —OMe | Me | 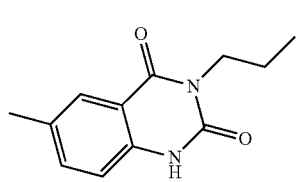 | / | 313 | 407 |
| 14 | 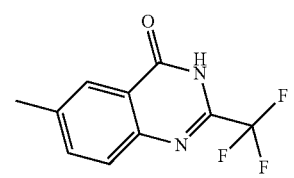 | Me | | Na | 361 | 482 |
| 15 | —OMe | Me | | / | 287 | 348 |
| 16 | —OMe | Me | | / | 291 | 402 |

TABLE-continued
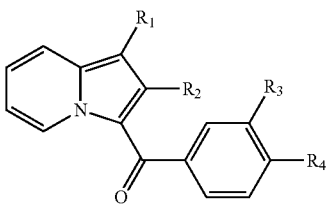
(I)
| No. | R₁ | R₂ | [structure] | Salt | Mp (°C.) | M + H⁺ |
|---|---|---|---|---|---|---|
| 17 | —OMe | Me | 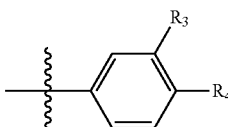 | / | 294 | 394 |
| 18 | —OMe | Me | 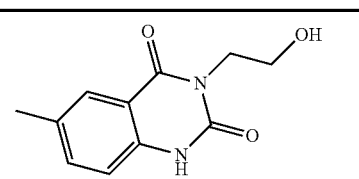 | / | 292 | 408 |
| 19 | —OMe | Me | 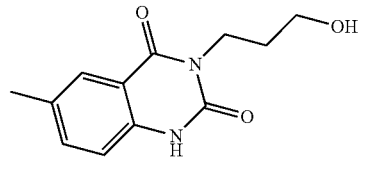 | / | 211 | 420 |
| 20 | —OMe | Me | 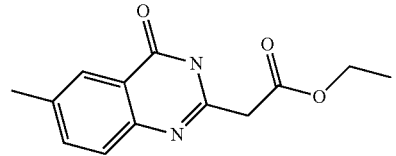 | / | 254 | 422 |
| 21 | —OMe | Me | 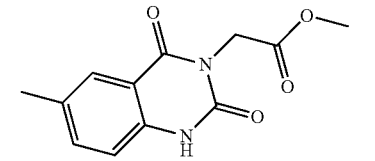 | Na | 333 | 422 |
| 22 | phenyl | Me | 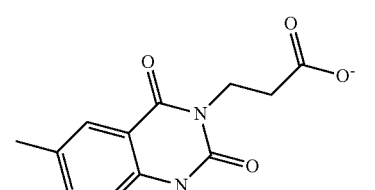 | / | 246 | 482 |
| 23 | —OMe | Me | 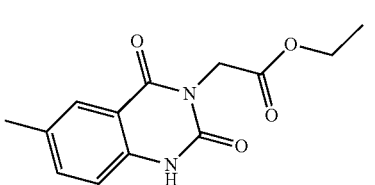 | / | 147 | 406 |

TABLE-continued
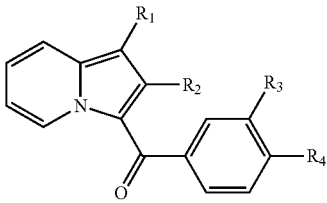
(I)
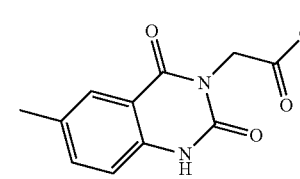
| No. | R₁ | R₂ | | Salt | Mp (° C.) | M + H⁺ |
|---|---|---|---|---|---|---|
| 24 | —OMe | phenyl | 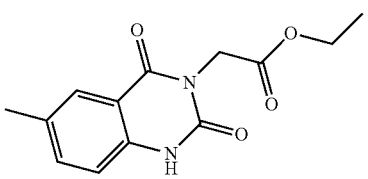 [SMILES: CCOC(=O)Cn1c(=O)[nH]c2ccc(C)cc2c1=O] | Na | 337 | 470 |
| 25 | —OMe | phenyl | 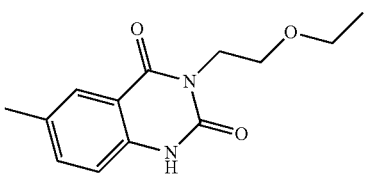 [SMILES: CCOCCn1c(=O)[nH]c2ccc(C)cc2c1=O] | / | 220 | 498 |
| 26 | —OMe | Me | 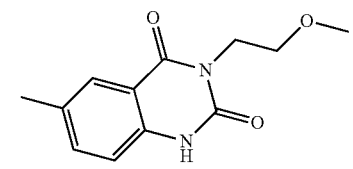 | / | 213 | 422 |
| 27 | —OMe | Me | 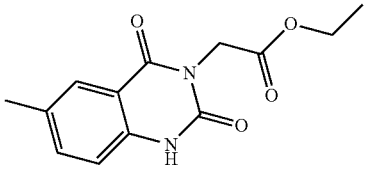 | / | 266 | 408 |
| 28 | —OMe | Me | 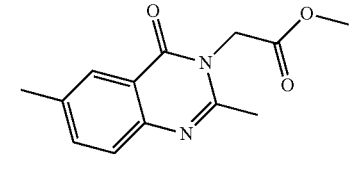 | / | 230 | 436 |
| 29 | —OMe | Me | | / | 191 | 420 |

TABLE-continued
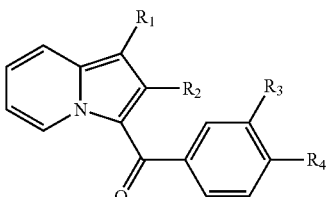
(I)
| No. | R₁ | R₂ | [Ar group] | Salt | Mp (° C.) | M + H⁺ |
|---|---|---|---|---|---|---|
| 30 | —OMe | Me | 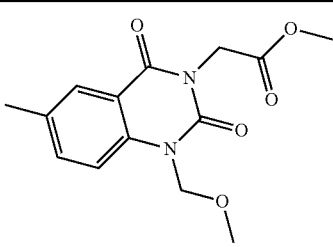 | / | 149 | 466 |
| 31 | —OMe | Me | 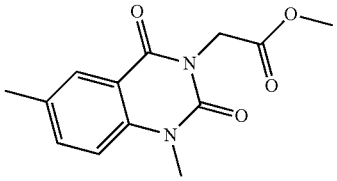 | / | 176 | 436 |
| 32 | —OMe | Me | 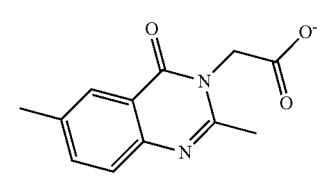 | Na | 344 | 406 |
| 33 | —OMe | phenyl | 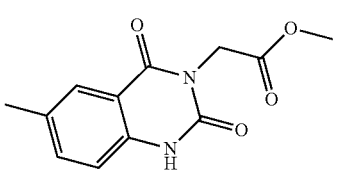 | / | 250 | 484 |
| 34 | —OMe | Me | 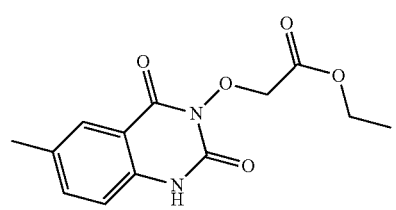 | / | 230 | 452 |
| 35 | —OMe | Me | 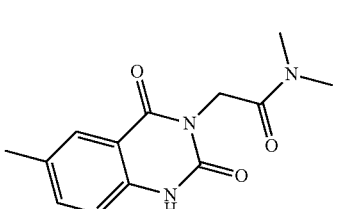 | / | 290 | 435 |

TABLE-continued
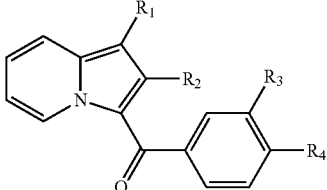
(I)
| No. | R₁ | R₂ | | Salt | Mp (° C.) | M + H⁺ |
|---|---|---|---|---|---|---|
| 36 | —OMe | Me | 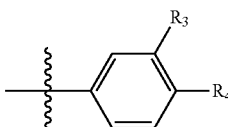 | / | 176 | 446 |
| 37 | —OMe | Me | 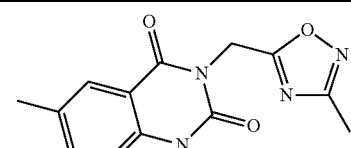 | / | 145 | 389 |
| 38 | —OMe | Me | 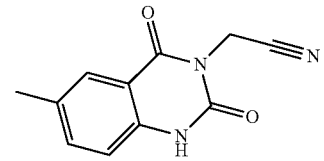 | Na | 339 | 432 |
| 39 | —OMe | Me | 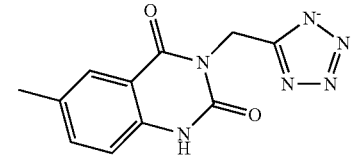 | / | 297 | 437 |
| 40 | —OMe | phenyl | 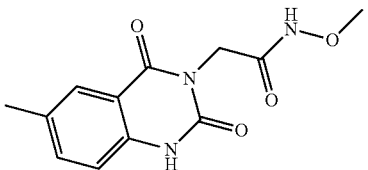 | / | 353 | 483 |
| 41 | —OMe | phenyl | 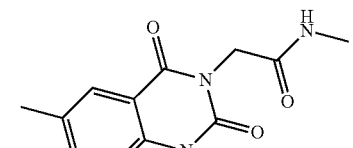 | / | 313 | 497 |
| 42 | —OMe | phenyl | 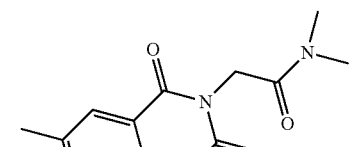 | / | 274 | 499 |

TABLE-continued (I)

| No. | R₁ | R₂ | (Ar group) | Salt | Mp (°C.) | M + H⁺ |
|---|---|---|---|---|---|---|
| 43 | (3-methylbenzoate) | Me | (6-methyl-2-methyl-quinazolin-4(3H)-one) | Na | 344 | 438 |
| 44 | —OMe | phenyl | (6-methyl-2,4-dioxo-1,2,3,4-tetrahydroquinazolin-3-yl propanoate) | Na | 304 | 484 |
| 45 | —OMe | phenyl | (6-methyl-3-((3-methyl-1,2,4-oxadiazol-5-yl)methyl)quinazoline-2,4(1H,3H)-dione) | / | 228 | 508 |
| 46 | —OMe | Me | (6-methyl-3-((5-methyl-1,3,4-oxadiazol-2-yl)methyl)quinazoline-2,4(1H,3H)-dione) | / | 267 | 446 |
| 47 | —OMe | Me | (2-(6-methyl-4-oxoquinazolin-3(4H)-yl)acetate) | Na | 310 | 392 |
| 48 | —O—(CH₂)₂—OCH₃ | Me | (6-methyl-3-propylquinazoline-2,4(1H,3H)-dione) | / | 215 | 436 |

TABLE-continued
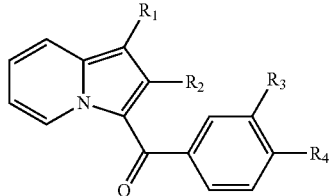
(I)
| No. | $R_1$ | $R_2$ | 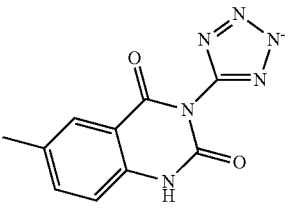 [SMILES: Cc1ccc2[nH]c(=O)n(-c3nn[n-]n3)c(=O)c2c1] | Salt | Mp (° C.) | M + H+ |
|---|---|---|---|---|---|---|
| 49 | —OMe | Me | 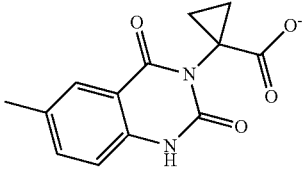 | Na | / | 418 |
| 50 | —OMe | phenyl | 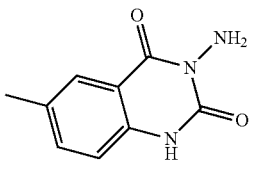 | Na | 321 | 496 |
| 51 | —OMe | Me | 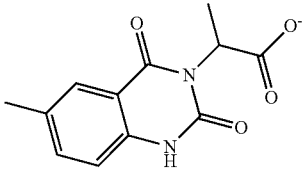 | / | 220 | 365 |
| 52 | —OMe | Me | 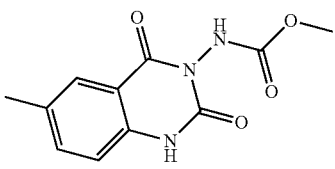 | Na | 283 | 422 |
| 53 | —OMe | Me | 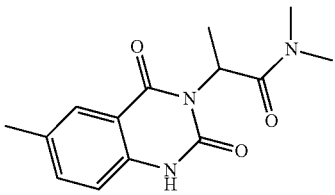 | / | 266 | 423 |
| 54 | —OMe | Me | | / | 268 | 449 |

TABLE-continued
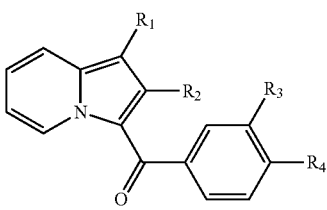
| No. | R₁ | R₂ | [structure] | Salt | Mp (°C.) | M + H⁺ |
|---|---|---|---|---|---|---|
| 55 | —OMe | Me | | / | 226 | 479 |
| 56 | —OMe | Me | | / | 262 | 419 |
| 57 | —OMe | phenyl | | / | 236 | 525 |
| 58 | —OMe | phenyl | (chiral) | / | 249 | 484 |
| 59 | —OMe | Me | | / | 249 | 436 |
| 60 | —OMe | phenyl | | / | / | 512 |

TABLE-continued
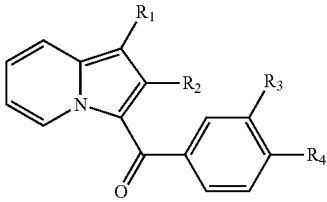
(I)
| No. | R₁ | R₂ | | Salt | Mp (° C.) | M + H⁺ |
|---|---|---|---|---|---|---|
| 61 | —OMe | Me | 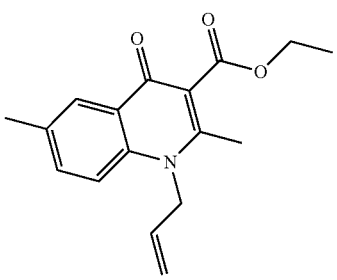 | / | 101 | 459 |
| 62 | —OMe | Me | 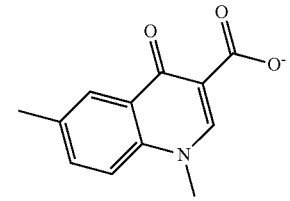 | Na | 258 | 391 |
| 63 | —OMe | Me | 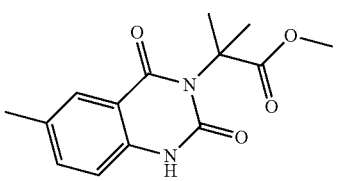 | / | 150 | 450 |
| 64 | —OMe | phenyl | 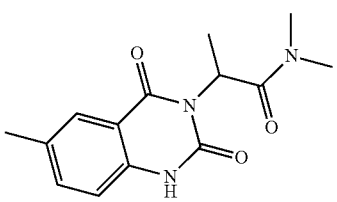 | / | 265 | 511 |
| 65 | —OMe | phenyl | 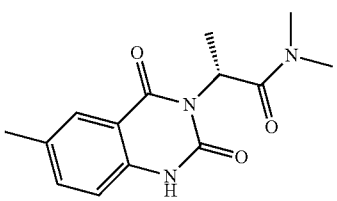<br>(chiral) | / | 225 | 511 |

TABLE-continued
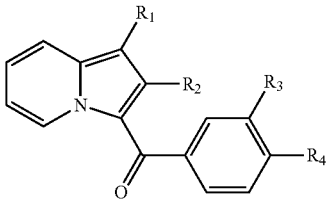
(I)
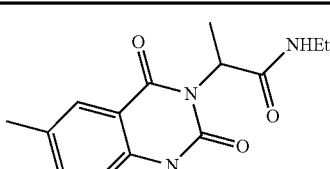
| No. | R₁ | R₂ | (structure) | Salt | Mp (°C.) | M + H⁺ |
|-----|-----|-----|-----|------|----------|--------|
| 66 | —OMe | phenyl | 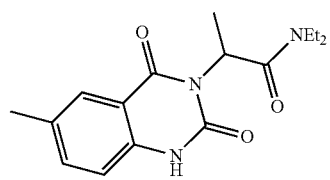 | / | 307 | 511 |
| 67 | —OMe | phenyl | 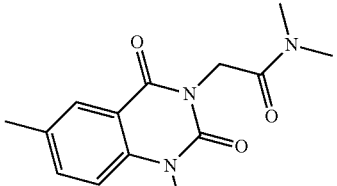 | / | 324 | 539 |
| 68 | —OMe | Me | 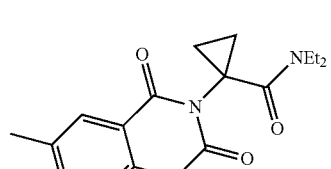 | / | 276 | 449 |
| 69 | —OMe | Me | 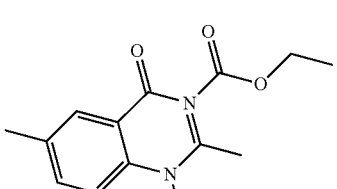 | / | 290 | 461 |
| 70 | —OMe | Me | 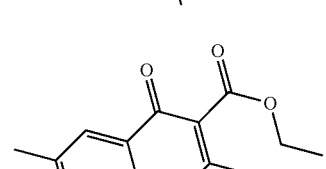 | / | / | 433 |
| 71 | —OMe | Me |  | / | 257 | 419 |

TABLE-continued
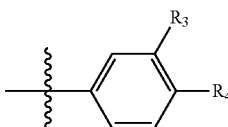
| No. | R₁ | R₂ | [Ar group] | Salt | Mp (°C.) | M + H⁺ |
|---|---|---|---|---|---|---|
| 72 | —OMe | Me | 1,2,6-trimethyl-4-oxo-1,4-dihydroquinoline-3-carboxylate | Na | 254 | 405 |
| 73 | —OMe | Me | 2,6-dimethyl-4-oxo-1,4-dihydroquinoline-3-carboxylate | Na | / | 391 |
| 74 | —OMe | Me | N,N,1,2,6-pentamethyl-4-oxo-1,4-dihydroquinoline-3-carboxamide | / | 268 | 432 |
| 75 | —OMe | Me | N,1,2,6-tetramethyl-4-oxo-1,4-dihydroquinoline-3-carboxamide | / | 258 | 418 |
| 76 | —OMe | Me | 1,2,6-trimethyl-4-oxo-1,4-dihydroquinoline-3-carboxamide | / | 313 | 404 |

TABLE-continued
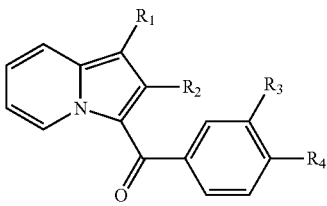
(I)
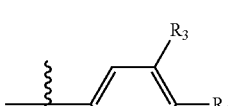
| No. | R₁ | R₂ | | Salt | Mp (° C.) | M + H⁺ |
|---|---|---|---|---|---|---|
| 77 | —OMe | Me | 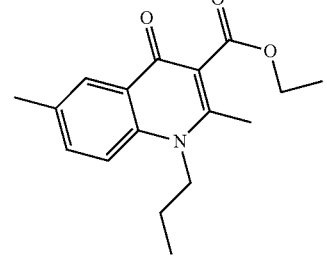 | / | 91 | 461 |
| 78 | —OMe | Me | 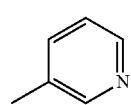 | Na | 267 | 433 |
| 79 | 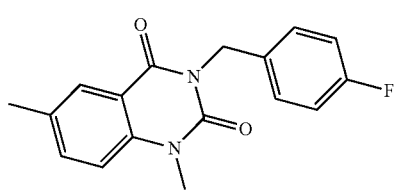 | Me | 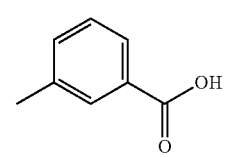 | HCl | 264 | 519 |
| 80 | 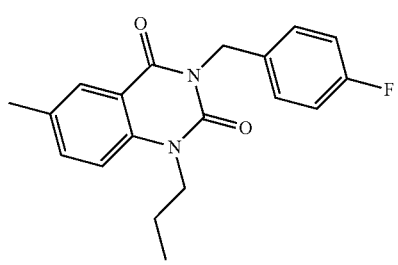 | Me | 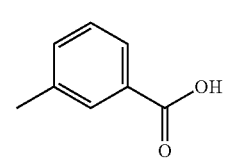 | Na | 246 | 590 |
| 81 | 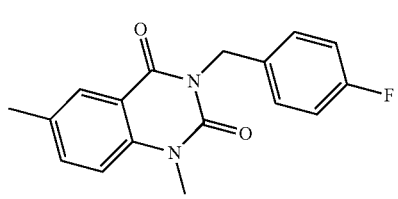 | Me | | Na | 267 | 562 |

TABLE-continued
(I)
| No. | R₁ | R₂ | 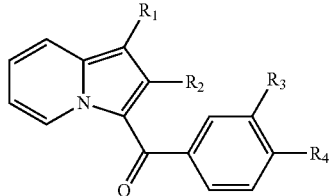 | Salt | Mp (° C.) | M + H⁺ |
|---|---|---|---|---|---|---|
| 82 | OMe | Me | 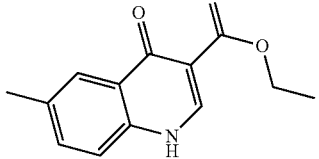 | / | 271 | 405 |
| 83 | OMe | Me | 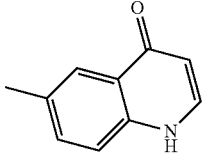 | Na | 270 | 377 |
| 84 | OMe | Me | 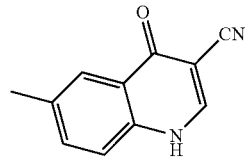 | / | / | 333 |
| 85 | OMe | Me | 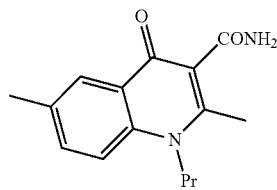 | / | 325 | 358 |
| 86 | OMe | Me | 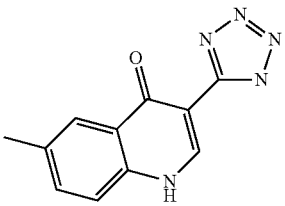 | / | 224 | 432 |
| 87 | OMe | Me |  | Na | 336 | 401 |

TABLE-continued
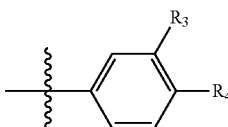
| No. | R₁ | R₂ | | Salt | Mp (° C.) | M + H⁺ |
|---|---|---|---|---|---|---|
| 88 | OMe | Me | 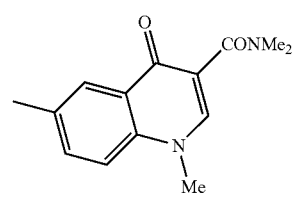 | / | 298 | 418 |
| 89 | OMe | Me | 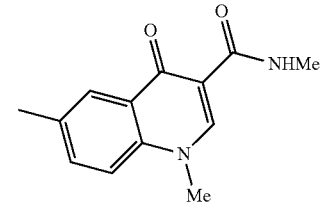 | / | 294 | 404 |
| 90 | OMe | Me | 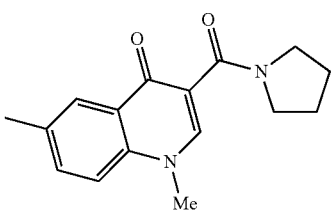 | / | 207 | 444 |
| 91 | OMe | Me | 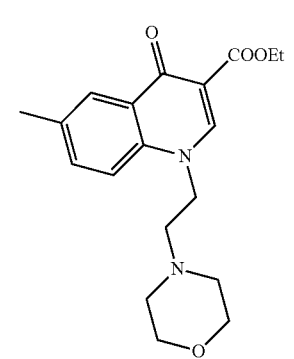 | / | 144 | 518 |

TABLE-continued
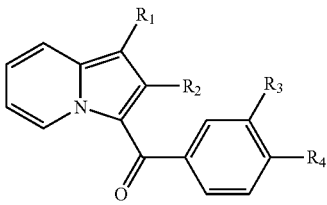
(I)
| No. | R₁ | R₂ | [Ar group] | Salt | Mp (°C.) | M + H⁺ |
|---|---|---|---|---|---|---|
| 92 | OMe | Me | 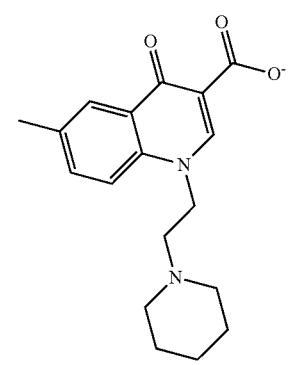 | / | 216 | 488 |
| 93 | OMe | Me | 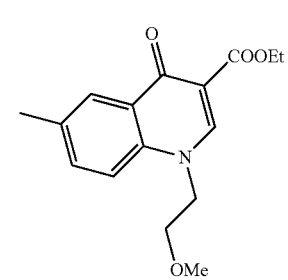 | / | 163 | 463 |
| 94 | OMe | Me | 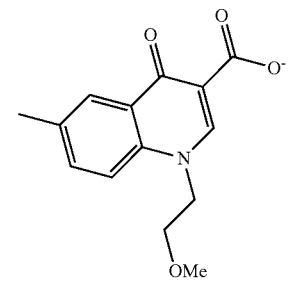 | Na | 289 | 435 |
| 95 | OMe | Me | 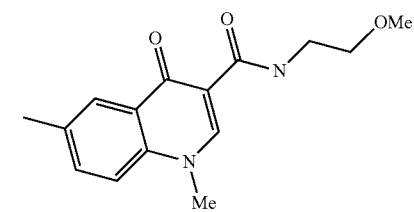 | / | 208 | 448 |

TABLE-continued
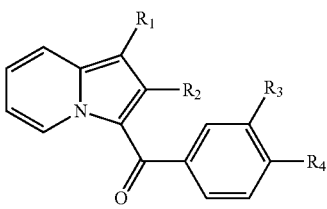
(I)
| No. | R₁ | R₂ | (structure) | Salt | Mp (° C.) | M + H⁺ |
|---|---|---|---|---|---|---|
| 96 | OMe | Me | 6-methyl-4-oxo-1H-quinoline-3-C(O)NHMe | / | 324 | 390 |
| 97 | OMe | Me | 6-methyl-1-Me-4-oxo-quinoline-3-C(O)NHPr | / | 220 | 432 |
| 98 | OMe | Me | 6-methyl-1-(CH₂CH₂OMe)-4-oxo-quinoline-3-C(O)NHMe | / | 239 | 448 |
| 99 | OMe | Me | 6-methyl-1-Me-4-oxo-quinoline-3-CN | / | 304 | 372 |
| 100 | OMe | Ph | 6-methyl-1-Me-4-oxo-quinoline-3-COOEt | / | / | 481 |

TABLE-continued (I)

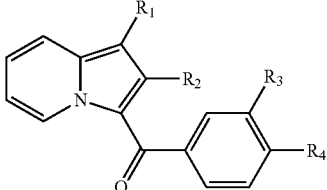

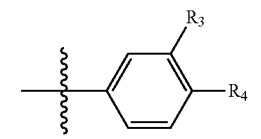

| No. | R₁ | R₂ | (Ar group) | Salt | Mp (°C.) | M+H⁺ |
|---|---|---|---|---|---|---|
| 101 | OMe | Ph | 6-methyl-1-methyl-4-oxo-1,4-dihydroquinoline-3-carboxylate | Na | 240 | 453 |
| 102 | H | Me | ethyl 6-methyl-1-methyl-4-oxo-1,4-dihydroquinoline-3-carboxylate (COOEt) | / | 232 | 389 |
| 103 | —O—(CH₂)₂—OCH₃ | Me | 6-methyl-1-methyl-4-oxo-1,4-dihydroquinoline-3-carboxylate | Na | / | 435 |
| 104 | 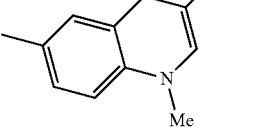 | Me | 6-methyl-1-methyl-4-oxo-1,4-dihydroquinoline-3-carboxylate | / | 163 | 488 |
| 105 | H | Me | N-methyl 6-methyl-1-methyl-4-oxo-1,4-dihydroquinoline-3-carboxamide (CONHMe) | / | 328 | 374 |
| 106 | 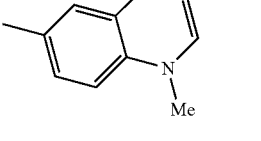 | Me | N-methyl 6-methyl-1-methyl-4-oxo-1,4-dihydroquinoline-3-carboxamide (CONHMe) | HCl | 228 | 451 |

TABLE-continued
(I)
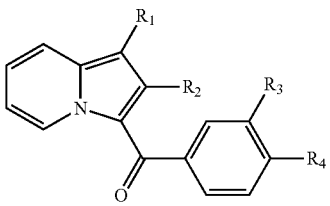
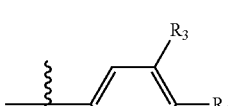
| No. | R₁ | R₂ | | Salt | Mp (°C.) | M + H⁺ |
|---|---|---|---|---|---|---|
| 107 | 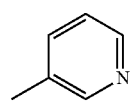 | Me | 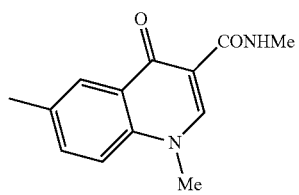 | HCl | 324 | 451 |
| 108 | 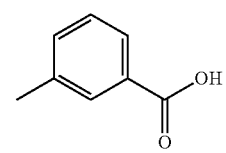 | Me | 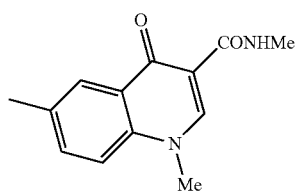 | Na | 311 | 494 |
| 109 | O—(CH₂)₂—OCH₃ | Me | 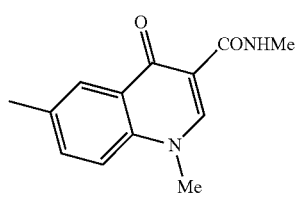 | / | / | 448 |
| 110 | 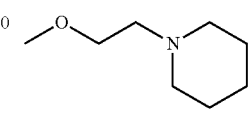 | Me | 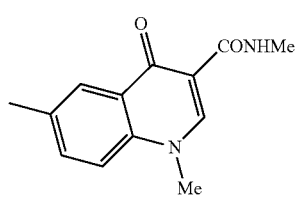 | HCl | / | 501 |
| 111 | Ph | Me | 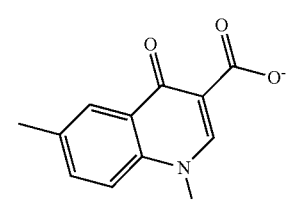 | Na | | 521 |
| 112 | Ph | Me | 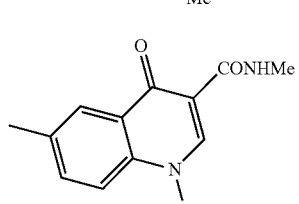 | / | / | 450 |

The compounds according to the invention were the subject of pharmacological assays for determining their FGF-inhibiting effect.

EXAMPLE 16

FGF-2-Induced In Vitro Angiogenesis of HUVEC Cells

In order to demonstrate the ability of the FGF-R antagonists of the present invention to inhibit FGF-induced angiogenesis, in vitro angiogenesis experiments were carried out with human endothelial cells of HUVEC type stimulated with FGF-2 or b-FGF.

To do this, matrices composed of matrigel (growth factor reduced matrigel, Becton Dickinson 356230) and collagen (rat tail collagen type I, Becton Dickinson 354236) are deposited, at a rate of 160 µl, into each chamberslide well (Biocoat Cellware collagen, Type I, 8-well culturesides: Becton Dickinson 354630), or 60 µl per well of 96-well plates (Biocoat collagen I cellware, Becton Dickinson 354407). The matrix is prepared by mixing ⅓ of matrigel, 1 mg/ml final concentration of collagen, NaOH (0.1N) (0.026× the volume of collagen in µl) and 1×PBS, and the volume is then adjusted with water. The gels are kept at 37° C. for 1 hour so as to allow them to polymerize. Next, the human vein endothelial cells (HUVECs ref: C-12200-Promocell) were seeded at 15×10$^3$ or 6×10$^3$ cells/well in 400 or 120 µl (for the 8-well or 96-well plates respectively) of EBM medium (Clonetics C3121)+2% FBS+10 µg/ml hEGF. They were stimulated with 1 or 3 ng/ml of FGF-2 (R&D systems, 133-FB-025; Invitrogen, PHG0026) for 24 h at 37° C. in the presence of 5% $CO_2$. After 24 hours, the length of the network of microtubules formed was measured using a computer-assisted image analysis system (Imagenia Biocom, Courtaboeuf, France) and the total length of the pseudotubules in each well was determined. The average total length of the microcapillary network was calculated in µm for each condition corresponding to the average of 6 replicates.

Stimulation with FGF2 makes it possible to induce the formation of new tubules. An FGF-R antagonist is considered to be active in this test as long as it is capable of partially inhibiting this angiogenesis at a dose less than or equal to 300 nM.

Example of Screening for FGF-R Antagonists

In this experiment, the molecules are evaluated at 3 and 30 nM on induction of the angiogenesis of HUVEC human cells by FGF-2. Antagonist compounds No. 87, 88, 89 and 90 are declared active since they exhibit an inhibitory activity of pseudotubule formation which is greater than or equal to 20% at a dose less than or equal to 300 nM.

TABLE 1

In vitro angiogenesis of HUVEC cells stimulated with FGF-2 and effect of FGF-R antagonists (inhibition of angiogenesis as a percentage of the control)

| Compounds No. | Percentage inhibition of angiogenesis (%) | |
|---|---|---|
| | 3 nM | 30 nM |
| 87 | 41 | 33 |
| 88 | 39 | 33 |
| 89 | 39 | 46 |
| 90 | 26 | 46 |
| 96 | 123 | 129 |
| 105 | 25 | 105 |

EXAMPLE 17

FGF-2-Induced In Vitro Proliferation of HUVEC Cells

In order to demonstrate the ability of the FGF-R antagonists of the present invention to inhibit FGF-induced cell proliferation, in vitro proliferation experiments were carried out with human endothelial cells of HUVEC type stimulated with FGF-2 or b-FGF.

To do this, HUVEC human vein endothelial cells (promocell, C-12200) are seeded at a rate of 5000 cells per well of a 96-well plate (Biocoat collagen I cellware, Becton Dickinson 354650) in 100 µl of RPMI 1640 deprivation medium (Invitrogen, 31872-025) supplemented with 0.5% or 1% FCS, 2 mM glutamine, 1× sodium pyruvate (Invitrogen, 11360-039) and 1×NEAA (Invitrogen, 11140-035), overnight at 37° C. in the presence of 5% $CO_2$. The following morning, the medium is suctioned-off and replaced with 50 µl of deprivation medium containing the antagonists at a 2× concentration, to which are added 50 µl of FGF-2 (R&D systems, 133-FB-025; Invitrogen, PHG0026) at 0.2 ng/ml (i.e. 2×). After 48 or 72 h, 100 µl of Cell Titer-GLOW Luminescent Cell Viability Assay (Promega, G7571) are added for 10 min in order to measure, by means of a luminometer, the amount of ATP present in the cells and which is in relation to the number of cells per well corresponding to the cell proliferation.

The antagonists of the present invention are considered to be active as long as they are capable of inhibiting FGF-2-induced proliferation of HUVEC cells at a dose less than or equal to 300 nM.

Example of HUVEC Cell Proliferation Induced by FGF-2 and Inhibited by FGF-R Antagonists Compounds No. 66 and No. 69 inhibit the FGF-2-induced cell proliferation since, in their presence, a reduction in proliferation of greater than or equal to 20% is observed for doses less than or equal to 300 nM.

TABLE 2

Cell proliferation of HUVEC cells stimulated with FGF-2 and effect of FGF-R antagonists (inhibition of proliferation as percentage of the control)

| Compounds No. | Percentage inhibition of angiogenesis (%) | |
|---|---|---|
| | 30 nM | 300 nM |
| 69 | 26 | 49 |
| 66 | 17 | 45 |
| 96 | 123 | 129 |
| 105 | 14 | 123 |

More generally, all the compounds according to the invention are active, at the dose of 300 nM, in in vitro angiogenesis of HUVEC cells induced by FGF-2 or in in vitro proliferation of HUVEC cells induced by FGF-2.

EXAMPLE 18

Model of Inflammatory Angiogenesis in Mice

Angiogenesis is required for the development of chronic inflammatory diseases such as rheumatoid arthritis. The formation of new vessels allows not only the perfusion of pathological tissues, but also the transport of cytokines responsible for establishing the chronicity of the disease.

The model described by Colville-Nash et al., in 1995, makes it possible to study pharmacological agents capable of modulating the occurrence of angiogenesis in an inflammatory context. The model is developed on OF1 female mice (Charles River Laboratories) weighing approximately 25 g, and by groups of 12. The animals are anaesthetized with sodium pentobarbital (60 mg/kg; Sanofi Nutrition Santé animale)) intraperitoneally. An air pocket is created on the back of the mouse by subcutaneous injection of 3 ml of air. After they have awoken, the animals receive a treatment generally by gavage, and receive an injection of 0.5 ml of Freund's adjuvant (Sigma) with 0.1% of croton oil (Sigma) in the pocket. Seven days later, the mice are again anaesthetized and placed on a hot plate at 40° C. One ml of carmine red (Aldrich Chemicals, 5% in 10% of gelatin) is injected into the tail vein. The animals are then placed at 4° C. for 2-3 hours. The skins are then taken and dried for 24 h in an oven at 56° C. The dry tissues are weighed and placed in 1.8 ml of digestion solution (2 mM dithiothreitol, 20 mM $Na_2HPO_4$, 1 mM EDTA, 12 U/ml papain) for 24 h. The dye is then dissolved in 0.2 ml of 5M NaOH. The skins are centrifuged at 2000 rpm for 10 min at ambient temperature. The supernatants are filtered through 0.2 μm cellulose acetate membranes. The filtrates are read in a spectrophotometer at 492 nm against a carmine red calibration range. Two parameters are studied: the dry weight of the granuloma and the amount of dye after digestion of the tissues. The results are expressed as mean values (±sem). The differences between the groups are tested with an ANOVA followed by a Dunnett's test, of which the reference group is the "solvent control" group.

The FGF-R antagonists are evaluated between 1 and 50 mg/kg using methylcellulose/tween (0.6% v/v) as vehicle or any other vehicle which allows the active ingredient to be solubilized. The molecules are administered daily, orally (one or two times a day) by gavage. The antagonists of the present invention are considered to be active as long as they enable a significant reduction in the angiogenic parameter, i.e. a reduction in the amount of carmine red dye in the skins of the animals tested.

Example of evaluation of FGF-R antagonists in the model of inflammatory angiogenesis in mice. Compounds No. 76 and No. 35 (example 1) at 10 or 30 mg/kg, after one week of daily treatment, significantly reduce the two parameters measured: the weight of the granuloma (dry weight of the skin) corresponding to the inflammation part of the model, and the dye content corresponding to the angiogenesis.

TABLE 3

Effect of the FGF-R antagonists, in a model of inflammatory angiogenesis, on the dry weight of the skins or on their content of carmine red dye.

| Model of inflammatory angiogenesis | % inhibition of the inflammatory parameter (mass of the granuloma) | % inhibition of the angiogenic parameter (dye content) |
|---|---|---|
| Compound No. 76; 10 mg/kg | 19 | 23 |
| Compound No. 62 (example 11); 10 mg/kg | 38 | 43 |
| Compound No. 35 (example 1); 30 mg/kg | 36 | 36 |
| Compound No. 1; 30 mg/kg | 24 | 44 |
| Compound No. 11; 10 mg/kg | 23 | 14 |
| Compound No. 20; 30 mg/kg | 28 | 25 |
| Compound No. 15 (example 8); 30 mg/kg | 21 | 21 |
| Compound No. 69; 30 mg/kg | 35 | 11 |
| Compound No. 76; 10 mg/kg | 19 | 23 |

EXAMPLE 19

4T1 Orthotopic Mammary Carcinoma Model in Mice

In order to evaluate the effect of the FGF-R antagonists in a murine tumour model, 4T1 mouse mammary carcinoma cells are injected into the mammary gland. The cells proliferate until the formation of a tumour after infiltration of the cells of the tumour microenvironment.

The 4T1 cells are cultured in RPM 1640 medium containing 10% FCS and 1% glutamine, supplemented with 1 mg/ml of geneticin. On the day of the injection into the mouse, the 4T1 cell concentration is adjusted to $2\times10^6$ cells/ml in PBS in order to inject $1\times10^5$ cells in 50 μl.

Mice (Balb/c, female, Charles River, approximately 8+/−2 weeks old) are anaesthetized by intraperitoneal injection of a mixture of 5% Rompun (xylazine), 10% Imalgene (ketamine) and 85% NaCl, in a proportion of 10 ml/kg. The injection zone (top-right nipple) is disinfected with hexomedine. After having vortexed the cells, 50 μl are removed in a syringe and injected into the nipple with a 26 G needle. The day of injection corresponds to D1. There are 15 mice in each group of mice (10 mice will be devoted to the ELISA assays and 5 mice to the histology). The FGF-R antagonists are evaluated at between 1 and 50 mg/kg in methylcellulose/tween (0.6% v/v) or any other vehicle which makes it possible to solubilize the active ingredient. The molecules are administered daily, orally (one or two times a day) by gavage, this taking place from D5 to D21, which is the day before the samples are taken. From D5, the tumours are measured as soon as possible, every two days, or even every day at the end of the experiment, using a caliper (sliding caliper). It is done in the following way: the longest length (L) and the perpendicular to the centre (I) are measured in mm. The volume in $mm^3$ is then defined by means of the mathematical formula which determines the volume of an ellipsoid: $(I^2 \times L) \times 0.52$. On the day the samples are taken, generally D22, the mice are sacrificed by means of an excess of sodium pentobarbital after having measured the volume of the tumours. The tumours are then cleared, photographed and weighed. The lungs are also removed and the metastases are counted after boin staining.

The antagonists of the present invention are considered to be active as long as they allow a significant reduction in the volume of the tumour and/or any number of lung metastases.

Example of 4T1 Mammary Carcinoma in Mice

The compounds considered to be active in the inflammatory angiogenesis model are evaluated in the 4T1 mammary carcinoma model in mice at between 1 and 50 mg/kg and showed a reduction in tumour volume of up to 37% and a decrease in the number of lung metastases of up to 38%.

It therefore appears that the compounds of formula (I) according to the present invention, by virtue of their FGF antagonist effect, reduce in vitro and in vivo, angiogenesis, tumour growth and metastasization.

Generally, FGFs and their receptors play an important role, by means of autocrine, paracrine or juxtacrine secretions, in phenomena where there is dysregulation of the stimulation of cancer cell growth. Furthermore, FGFs and their receptors affect tumour angiogenesis which plays a predominant role both on tumour growth and also on metastasization phenomena.

Angiogenesis is a process in which new capillary vessels are generated from pre-existing vessels or by mobilization and differentiation of bone marrow cells. Thus, both uncontrolled proliferation of endothelial cells and mobilization of angioblasts from the bone marrow are observed in tumour neovascularization processes. It has been shown, in vitro and in vivo, that several growth factors stimulate endothelial, proliferation, and in particular FGF-1 or a-FGF and FGF-2 or b-FGF. These two factors induce proliferation, migration and protease production by endothelial cells in culture and neovascularization in vivo. a-FGF and b-FGF interact with endothelial cells by means of two classes of receptors, high-affinity receptor tyrosine kinases (FGF-Rs) and low-affinity receptors of heparin sulphate proteoglycan type (HSPGs) located at the surface of cells and in extracellular matrices. Although the paracrine role of these two factors on endothelial cells is widely described, these FGFs could also intervene on the cells through an autocrine process. Thus, FGFs and their receptors represent very relevant targets for therapies aimed at inhibiting angiogenesis processes (Keshet E, Ben-Sasson S A., *J. Clin. Invest*, (1999), Vol. 501, pp. 104-1497; Presta M, Rusnati M, Dell'Era P, Tanghetti E, Urbinati C, Giuliani R et al, New York: Plenum Publishers, (2000), pp. 7-34, Billottet C, Janji B, Thiery J. P., Jouanneau J, Oncogene, (2002) Vol. 21, pp. 8128-8139).

Moreover, systematic studies aimed at determining the expression due to FGFs and their receptors (FGF-Rs) of various types of tumour cells demonstrate that a cell response to these two factors is functional in a large majority of human tumour lines studied. These results support the hypothesis that an FGF receptor antagonist could also inhibit tumour cell proliferation (Chandler L A, Sosnowski B A, Greenlees L, Aukerman S L, Baird A, Pierce G F., *Int. J. Cancer*, (1999), Vol. 58, pp. 81-451).

FGFs play an important role in the growth and maintenance of prostate cells. It has been shown, both in animal models and in humans, that an impairment in the cell response to these factors plays an essential role in the progression of prostate cancer. Specifically, in these pathological conditions, both an increase in the production of a-FGF, b-FGF, FGF-6, FGF-8 etc., by the fibroblasts, stromal cells, residual basal cells and endothelial cells present in the tumour and an increase in the expression of FGF receptors and ligands by the tumour cells are recorded. Thus, a paracrine stimulation of prostate cancer cells takes place, and this process appears to be a major component of this pathological condition. A compound which has an FGF receptor antagonist activity, such as the compounds of the present invention, may represent a therapy of choice in these pathological conditions (Giri D, Ropiquet F., *Clin. Cancer Res.*, (1999), Vol. 71, pp. 5-1063; Doll J A, Reiher F K, Crawford S E, Pins M R, Campbell S C, Bouck N P., *Prostate*, (2001), Vol. 305, pp. 49-293) (Sahadevan et al., 2007) (Kwabi-Addo et al, 2004).

Several studies show the presence of FGFs and of their receptors, FGF-Rs, both in human breast tumour lines (in particular MCF7) and in tumour biopsies. These factors appear to be responsible, in this pathological condition, for the appearance of the very aggressive phenotype and induce a strong metastasization. Thus, a compound which has FGF-R receptor antagonist activity, such as the compounds of formula I, may represent a therapy of choice in these pathological conditions (Vercoutter-Edouart A-S, Czeszak X, Crepin M, Lemoine J, Boilly B, Le Bourhis X et al., *Exp. Cell Res.*, (2001), Vol. 262, pp. 59-68) (Schwertfeger, 2009).

Cancerous melanomas are tumours which induce metastases with a high frequency and which are very resistant to the various chemotherapy treatments. The angiogenesis processes play a predominant role in the progression of a cancerous melanoma. Furthermore, it has been shown that the probability of the occurrence of metastases increases very greatly with the increase in the vascularization of the primary tumour. Melanoma cells produce and secrete various angiogenic factors, including a-FGF and b-FGF. Moreover, it has been shown that inhibition of the cellular effect of these two factors by means of the soluble FGF-R1 receptor blocks melanoma tumour cell proliferation and survival in vitro and blocks tumour progression in vivo. Thus, a compound which has an FGF receptor antagonist activity, such as the compounds of the present invention, may represent a therapy of choice in these pathological conditions (Rofstad E K, Halsor E F., *Cancer Res.*, (2000); Yayon A, Ma Y-S, Safran M, Klagsbrun M, Halaban R., *Oncogene*, (1997), Vol. 14, pp. 2999-3009).

Glyoma cells produce a-FGF and b-FGF in vitro and in vivo, and have various FGF receptors at their surface. This therefore suggests that these two factors play a pivotal role, by means of an autocrine and paracrine effect, in the progression of this type of tumour. Furthermore, like most solid tumours, the progression of gliomas and their ability to induce metastases is highly dependent on the angiogenic processes in the primary tumour. It has also been shown that FGF-R1 receptor antisenses block human astrocytoma proliferation. In addition, naphthalenesulphonate derivatives are described for inhibiting the cellular effects of a-FGF and b-FGF in vitro and the angiogenesis induced by these growth factors in vivo. An intracerebral injection of these compounds induces a very significant increase in apoptosis and a considerable decrease in angiogenesis, reflected by a considerable regression of gliomas in rats. Thus, a compound which has an a-FGF antagonist and/or b-FGF antagonist and/or FGF receptor antagonist activity, such as the compounds of the present invention, may represent a therapy of choice in these pathological conditions (Yamada S M, Yamaguchi F, Brown R, Berger M S, Morrison R S, *Glia*, (1999), Vol. 76, pp. 28-66; Auguste P, Gürsel D B, Lemière S, Reimers D, Cuevas P, Carceller F et al., *Cancer Res.*, (2001), Vol. 26, pp. 61-1717) (Loilome et al., 2008).

Active angiogenesis is also described for hepatocarcinomas or hepatocellular carcinoma (HCC). In vivo, tumour progression in HCCs requires a considerable supply of oxygen and nutrients. Hepatocarcinomas are tumours which are typically angiogenic, because a drastic modification is observed with respect to arterial vascularization, and this results in the acquisition of an uvasive and metastatic potential (Tanaka et al., 2006). FGFs participate actively in the development of tumour angiogenesis within HCCs and are frequently associated with the inflammatory process. They are also overexpressed in the context of chronic hepatitis and liver sclerosis (Uematsu et al., 2005) and the serum FGF level has been correlated with the clinicopathological progression of HCCs. Furthermore, the FGF-R4 receptor, and also FGF-R1, have been described as participating actively in HCC tumour genesis (Huang et al., 2006) (Nicholes et al., 2002). The antagonists of the present invention may therefore be a treatment of choice for hepatocellular carcinomas or hepatocarcinomas.

In lung cancers of NSCLC (Non-Small Cell Lung Cancer) type, recent studies show that b-FGF, FGF-9, FGF-R1 and FGF-R2 are regularly coexpressed in NSCLC cancer lines and especially in those resistant to anti-EGFR treatment such as gefitinib. These expressions are connected to the capacity for proliferation via autocrine cell signalling and anchorage-independent growth of tumours of NSCLC type and mainly the type insensitive to treatment with gefitinib (Marek et al., 2008). Furthermore, b-FGF has been suggested as playing an important role in the survival of NSCLC cells during treatment by chemotherapy, by inducing the overexpression of the anti-apoptotic proteins BCL-2, BCL-X, XIAP or BIRC3 (Pardo et al., 2002, 2003 and 2006). Thus, an FGF receptor antagonist, such as those of the present invention, may represent a therapy of choice for lung cancers of NSCLC type, alone or in combination with EGF receptor inhibitors or chemotherapies.

In approximately 10% of gastric cancers, this FGF-R2 gene amplification is observed. This amplification is associated with a poor vital prognosis for cancers of diffuse type. The proliferation of tumour cells may be ligand-independent or dependent on paracrine activation by FGF-7 (Turner et al., 2010). The antagonists of the present invention may therefore be a treatment of choice for gastric cancers.

More recently, the potential role of pro-angiogenic agents in leukaemias and lymphomas has been documented. Indeed, in general, it has been reported that cell clones in these pathological conditions can be destroyed naturally by the immune system or switch into an angiogenic phenotype which promotes their survival and then their proliferation. This change in phenotype is induced by an overexpression of angiogenic factors, in particular by macrophages, and/or a mobilization of these factors from the extracellular matrix (Thomas D A, Giles F J, Cortes J, Albitar M, Kantarjian H M., *Acta Haematol*, (2001), Vol. 207, pp. 106-190). Among the angiogenic factors, b-FGF has been detected in many lymphoblastic and hematopoietic tumour cell lines. FGF receptors are also present on the majority of these lines, suggesting a possible autocrine cellular effect of a-FGF and b-FGF inducing proliferation of these cells. Moreover, it has been reported that bone marrow angiogenesis via paracrine effects is correlated with the progression of some of these pathological conditions.

More particularly, it has been shown, in CLL (chronic lymphocytic leukaemia) cells, that b-FGF induces an increase in anti-apoptotic protein (Bcl2) expression, resulting in an increase in the survival of these cells, and that it therefore participates considerably in their cancerization. In addition, the b-FGF levels measured in these cells are very well-correlated with the stage of clinical advancement of the disease and the resistance to the chemotherapy applied in this pathological condition (fludarabine). Thus, a compound which has an FGF receptor antagonist activity, such as the compounds of the present invention, may represent a therapy of choice, either alone or in combination with fludarabine or other products that are active in this pathological condition (Thomas D A, Giles F J, Cortes J, Albitar M, Kantarjian H M., *Acta Haematol*, (2001), Vol. 207, pp. 106-190; Gabrilove J L, *Oncologist*, (2001), Vol. 6, pp. 4-7).

Furthermore, it has been shown in many recent studies that FGFs and FGF-Rs participate actively in the resistance of tumour and/or endothelial cells to treatments by chemotherapy, radiotherapy or else anti-VEGF treatments. These resistances use various cell mechanisms, such as protection against apoptosis by positive regulation of the Bcl-xl protein by FGF-R4 in the case of breast cancer resistance to doxorubicin (Roidl et al., 2009) or by FGF-2 production in the case of resistance of bladder tumours to cisplatin (Miyake et al., 1998), by activation of the Pi3K/AKT pathway by the FGF2/FGF-R1 couple in the case of resistance of acute myeloidal leukaemia cells to cytarabin (Karajannis et al., 2006), by stimulation of the RAS/MAP-K, PI3-K and mTOR pathway by FGF-1 for certain breast tumours resistant to anti-oestrogen treatments (Manuvakhova et al., 2006). The FGFs/FGF-Rs couple is also involved in resistance to anti-VEGF treatments in the case of pancreatic carcinomas (Casanovas et al., 2005) or of glioblastomas (Batchelor et al., 2007) or else in radiotherapy resistance phenomena (Gu et al., 2004; Moyal et al., 2009). Thus, the compounds of the present invention could be combined with existing therapies in order to limit the appearance of resistance phenomena.

Furthermore, tumour invasion, which is one of the marks of malignancy, consists of the translocation of tumour cells from the initial neoplastic locus to the surrounding host tissues, allowing the tumour to penetrate into the vascular endothelium in order to circulate and to form metastatic loci remote from the primary tumour. An increasing number of recent articles suggest that changes in the tissue architecture at the periphery of the tumour appear to be responsible for the epithelial-mesenchymal transition (EMT) process. EMT is a cell process by which epithelial cells modulate their phenotype and acquire mesenchymal cell properties through the disruption of intercellular adhesion and an increase in cell motility, thus playing an essential role in tumour progression by conferring an invasive and metastatic phenotype on carcinomas. Growth factors such as FGFs participate in this cell process by virtue of their stimulatory activity on cell migration and invasion, but also, as regards FGF receptors, by virtue of their ability to interact with cadherins, thus facilitating tumour cell migration (Cowin et al., 2005). The FGF-R antagonists described herein may be used for preventing these metastatic phases in a large number of cancers.

A correlation exists between the bone marrow angiogenesis process and "extramedullar disease" in CML (chronic myelomonocytic leukaemia). Various studies demonstrate that the inhibition of angiogenesis, in particular by means of a compound which has an FGF receptor antagonist activity, could represent a therapy of choice in this pathological condition.

The proliferation and migration of vascular smooth muscle cells contributes to intimal hypertrophy of the arteries and thus plays a predominant role in atherosclerosis and in restenosis after angioplasty and endoarterectomy.

In vivo studies show, after lesion of the carotid "balloon injury", a local production of a-FGF and of b-FGF. In this same model, an anti-FGF2 neutralizing antibody inhibits vascular smooth muscle cell proliferation and thus decreases intimal hypertrophy.

A chimeric protein consisting of FGF2 linked to a molecule such as saporin inhibits vascular smooth muscle cell proliferation in vitro and intimal hypertrophy in vivo (Epstein C E, Siegall C B, Biro S, Fu Y M, FitzGerald D., *Circulation*, (1991), Vol. 87, pp. 84-778; Waltenberger J., *Circulation*, (1997), pp. 96-4083).

Thus, FGF receptor antagonists, such as the compounds of the present invention, represent a therapy of choice, either alone or in combination with compounds that are antagonists of other growth factors involved in these pathological conditions, such as PDGF, in the treatment of pathological conditions related to vascular smooth muscle cell proliferation, such as atherosclerosis, post-angioplasty restenosis or restenosis following the implantation of endovascular prostheses (stents) or during aortocoronary bypasses.

Cardiac hypertrophy occurs in response to a stress of the ventricular wall induced by an overload in terms of pressure or volume. This overload can be the consequence of numerous physiopathological states, such as hypertension, AC (aortic coarctation), myocardial infarction, and various vascular disorders. The consequences of this pathological condition are morphological, molecular and functional changes such as cardiac myocyte hypertrophy, matrix protein accumulation and foetal gene reexpression. b-FGF is implicated in this pathological condition. Specifically, the addition of b-FGF to cultures of newborn rat cardiomyocytes modifies the profile of the genes corresponding to the contractile proteins, resulting in a foetal-type gene profile. In a complementary manner, adult rat myocytes show a hypertrophic response under the effect of b-FGF, this response being blocked by anti-b-FGF neutralizing antibodies. Experiments carried out in vivo in b-FGF-knock-out transgenic mice show that b-FGF is the major factor stimulating cardiac myocyte hypertrophy in this pathological condition (Schultz JeJ, Witt S A, Nieman M L, Reiser P J, Engle S J, Zhou M et al., *J. Clin. Invest*., (1999), Vol. 19, pp. 104-709). Thus, a compound, such as the compounds of the present invention, which has an FGF receptor antagonist activity represents a therapy of choice in the treatment of heart failure and any other pathological condition associated with cardiac tissue degeneration. This treatment could be carried out alone or in combination with the common treatments (beta-blockers, diuretics, angiotensic antagonists, antiarrythmics, anti-calcium agents, antithrombotics, etc.).

Vascular disorders due to diabetes are characterized by an impairment of vascular reactivity and of blood flow, hyperpermeability, an exacerbated proliferative response and an increase in matrix protein deposits. More specifically, a-FGF and b-FGF are present in the preretinol membranes of patients having diabetic retinopathies, in the membranes of the underlying capillaries and in the vitreous humour of patients suffering from proliferative retinopathies. A soluble FGF receptor capable of binding both a-FGF and b-FGF is developed in diabetes-related vascular disorders (Tilton R G, Dixon R A F, Brock T A., *Exp. Opin. Invest. Drugs*, (1997), Vol. 84, pp. 6-1671). Thus, a compound, such as the compounds of formula I, which has an FGF receptor antagonist activity represents a therapy of choice, either alone or in combination with compounds that are antagonists of other growth factors involved in these pathological conditions, such as VEGF.

Fibrosis is the abnormal formation of scar tissues following a tissue lesion, and results in a chronic and progressive impairment of the affected organs that can result in serious dysfunction of the affected organ. It can occur in all tissues, but is mainly prevalent in organs exposed to chemical or biological attacks, such as the lungs, the skin, the kidneys, the digestive tract, the liver, etc. FGFs participate in this cell process by promoting the production and accumulation of extracellular matrices by fibroblasts, the proliferation of said fibroblasts and infiltration into many organs such as the kidneys or the lungs (Khalil et al., 2005) (Strutz et al., 2003). Antagonists of the activity of these FGFs, such as the molecules of the present invention, may be used alone or in combination in the treatment of fibrosis.

Rheumatoid arthritis (RA) is a chronic disease with an unknown aetiology. Although it affects many organs, the most serious form of RA is a progressive synovial inflammation of the joints resulting in destruction. Angiogenesis appears to considerably affect the progression of this pathological condition. Thus, a-FGF and b-FGF have been detected in the synovial tissue and in the joint fluid of patients suffering from RA, indicating that this growth factor is involved in the initiation and/or the progression of this pathological condition. In models of AIA (adjuvant-induced model of arthritis) in rats, it has been shown that the overexpression of b-FGF increases the severity of the disease, whereas an anti-b-FGF neutralizing antibody blocks the progression of RA (Malemud, 2007) (Yamashita A, Yonemitsu Y, Okano S, Nakagawa K, Nakashima Y, Irisa T et al., *J. Immunol.*, (2002), Vol. 57, pp. 168-450; Manabe N, Oda H, Nakamura K, Kuga Y, Uchida S, Kawaguchi H, *Rheumatol*, (1999), Vol. 20, pp. 38-714). Thus, the compounds according to the invention represent a therapy of choice in this pathological condition.

Recent scientific articles document the involvement of b-FGF in neuropathic pain. Specifically, an increase in astroglial b-FGF production is observed in astrocytes following a spinal cord lesion (Madiai at al., 2003). This b-FGF contributes to neuropathic pain due to contact or allodynia. Treatment using an anti-FGF2 neutralizing antibody reduces this mechanical allodynia (Madiai et al., 2005). The antagonists of the present invention are treatments of choice for pain by inhibiting the effect of FGF-2 on these receptors.

It has also been described that the level of growth factors having a pro-angiogenic activity, such as FGF-1 and -2, are greatly increased in the synovial fluid of patients suffering from osteoarthritis. In this type of pathological condition, a considerable modification is recorded in the balance between the pro- and anti-angiogenic factors inducing the formation of new vessels, and consequently, the vascularization of nonvascularized structures, such as joint cartilages or intervertebral discs. Thus, angiogenesis represents a key factor in bone formation (osteophytes), thus contributing to the progression of the disease. Additionally, the inervation of the new vessels can also contribute to the chronic pain associated with this pathological condition (Walsh D A., Curr Opin Rheumatol. 2004 September; 16(5):609-15). Thus, the compounds according to the invention represent a therapy of choice in this pathological condition.

IBD (inflammatory bowel disease) includes two forms of chronic inflammatory diseases of the intestine: UC (ulcerative colitis) and Crohn's disease (CD). IBD is characterized by an immune dysfunction reflected by an inappropriate production of inflammatory cytokines inducing the establishment of a local microvascular system. This angiogenesis of inflammatory origin results in an intestinal ischemia induced by vasoconstriction. High circulating and local levels of b-FGF have been measured in patients suffering from these pathological conditions (Kanazawa S, Tsunoda T, Onuma E, Majima T, Kagiyama M, Kkuchi K., *American Journal of Gastroenterology*, (2001), Vol. 28, pp 96-822; Thorn M, Raab Y, Larsson A, Gerdin B, Hallgren R., *Scandinavian Journal of Gastroenterology*, (2000), Vol. 12, pp. 35-408). The compounds of the invention which exhibit a high anti-angiogenic activity in an inflammatory angiogenesis model represent a therapy of choice in these pathological conditions.

Another disease which has a considerable inflammatory component and for which a strong implication of FGFs and FGF-Rs is described is benign prostatic hyperplasia (BPH). BPH is a disease related to ageing which is characterized by hyperplasia of the glandular tissues and of the stroma around the urethra until it becomes obstructed. At the cellular level, this pathological condition involves hyperplasia of the basal cells, an increase in the stromal mass, amplified matrix deposit or else a reduction in tissue elasticity (Untergasser et al., 2005). FGFs participate in the development of this disease by stimulating the proliferation of the prostatic stroma and epithelial cells, and in particular FGF-7 or KGF, but also FGF-2 or FGF-17 (Wang 2008, Boget 2001, Gir2001). In addition, FGFs promote the transdifferentiation step by modifying epithelial cell/stromal cell interactions, in combination with TGF-β (Untergasser 2005). Finally, certain receptors, such as FGF-R1, are overexpressed in BPH, promoting induction of the pathological condition and potentiating the paracrine effects of FGF-2 (Boget 2001). An antagonist of the effect of these FGFs is therefore a treatment of choice for benign prostatic hyperplasia.

Psoriasis is a chronic skin disease caused by a hyperproliferation of the epidermal keratinocytes, while clear cell acanthoma (CCA) is a benign neoplasm of the epidermis which also involves an abnormal proliferation of keratinocytes. These two skin diseases have similar histological characteristics despite different underlying causes: a thickening of the epidermis, inflammatory infiltrations of lymphocytes and neutrophils, dilation and tortuosity of the papillary capillaries. In both cases, KGF or FGF-7 plays a predominant role in the development of the pathological condition (Kovacs et al., 2006) (Finch et al., 1997). The use of the antagonists of the present invention may make it possible to slow down the development of such skin diseases.

FGF-R1, -R2 and -R3 receptors are involved in chronogenesis and osteogenesis processes. Mutations resulting in the expression of FGF-Rs that are always activated have been connected to a large number of human genetic diseases reflected by malformations of the skeleton, such as Pfeiffer syndrome, Crouzon syndrome, Apert syndrome, Jackson-Weiss syndrome and Bear-Stevenson cutis gyrate syndrome. Some of these mutations affect more particularly the FGF-R3 receptor, resulting in particular in achondroplasias (ACH), hyperchondroplasias (HCH) and TD (thanatophoric dysplasia); ACH being the most common form of dwarfism. From a biochemical point of view, the sustained activation of these receptors takes place via a dimerization of the receptor in the absence of ligand (Chen L., Adar R., Yang X. Monsonego E. O., LI C., Hauschka P. V, Yagon A. and Deng C. X., (1999), *The Journ. Of Clin. Invest.*, Vol. 104, no 11, pp. 1517-1525). Thus, the compounds of the invention which exhibit an FGF antagonist or FGF receptor antagonist activity and which inhibit FGF-R-dependent intracellular signalling represent a therapy of choice in these pathological conditions.

It is also known that adipose tissue is one of the rare tissues that, in adults, can develop or regress. This tissue is highly vascularized and a very dense network of microvessels surrounds each adipocyte. These observations have resulted in the testing of the effect of anti-angiogenic agents on adipose tissue development in adults. Thus, it appears that, in pharmacological models in ob/ob mice, the inhibition of angiogenesis is reflected by significant weight loss in the mice (Rupnick M A et al, (2002), *PNAS*, Vol. 99, No. 16, pp. 10730-10735). Furthermore, FGFs appear to be key regulators of adipogenesis in humans (Nutley et al., 2004). Thus, an FGF receptor antagonist compound which has a powerful anti-angiogenic activity may represent a therapy of choice in obesity-related pathological conditions.

By virtue of their low toxicity and their pharmacological and biological properties, the compounds of the present invention are of use in the treatment and prevention of any carcinoma which has a high degree of vascularization, such as lung, breast, prostate, oesophageal, pancreatic, liver, colon or kidney carcinomas, or which induces metastases, such as colon, breast, liver or stomach carcinomas, or melanomas, or which is sensitive to a-FGF or to b-FGF in an autocrine manner or else in pathological conditions of glioma type, lymphomas and leukaemias or, finally, in any therapy-resistance phenomenon. These compounds represent a therapy of choice, either alone or in combination with a chemotherapy, a radiotherapy or any other suitable treatment. The compounds according to the invention are also of use in the treatment and prevention of cardiovascular diseases, such as atherosclerosis, or restenosis post-angioplasty, in the treatment of diseases related to complications occurring following the implantation of endovascular stents and/or aortocoronary bypasses or other vascular grafts, and cardiac hypertrophy or vascular complications of diabetes, such as diabetic retinopathies. The compounds according to the invention are also of use in the treatment and prevention of chronic inflammatory diseases such as rheumatoid arthritis, IBD or benign prostatic hyperplasia. Finally, the compounds according to the invention can be used in the treatment and prevention of achondroplasias (ACH), hypochondroplasias (HCH) and TD (thanatophoric dysplasia), as also in the treatment of obesity.

The products according to the invention are also of use in the treatment and prevention of macular degeneration, in particular age-related macular degeneration (or ARMD). A major characteristic of the loss of sight in adults is the neovascularization and the subsequent haemorrhages which cause considerable functional disorders in the eye and which are reflected by early blindness. Recently, studying the mechanisms involved in ocular neovascularization phenomena has made it possible to demonstrate the involvement of pro-angiogenic factors in these pathological conditions. By using a laser-induced choroidial neoangiogenesis model, it has been possible to confirm that the products according to the invention also make it possible to modulate neovascularization of the choroid.

Moreover, the products of the invention can be used in the treatment or prevention of thrombopenias due in particular to anticancer chemotherapy. It has in fact been demonstrated that the products of the invention can improve circulating platelet levels during chemotherapy.

Finally, the products according to the invention are of use in the treatment and prevention of skin diseases, such as psoriasis or clear cell acanthoma, in combating the progression of liver, kidney or lung fibrosis, and also in the treatment of neuropathic pain.

A subject of the invention is, according to another of its aspects, medicaments which comprise a compound of formula (I), or an addition salt thereof with a pharmaceutically acceptable acid or base, or else a hydrate or a solvate of the compound of formula (I).

According to another of its aspects, the present invention relates to pharmaceutical compositions comprising, as active ingredient, a compound of formula (I) according to the invention. These pharmaceutical compositions contain an effective dose of at least one compound according to the invention, or a pharmaceutically acceptable salt or a hydrate or solvate of said compound, and also at least one pharmaceutically acceptable excipient. Said excipients are selected, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or optional salt, solvate or hydrate thereof, can be administered in unit administration form, as a mixture with conventional pharmaceutical excipients, to animals and to human beings for the prophylaxis or the treatment of the disorders or the diseases mentioned above.

The suitable unit administration forms comprise forms for oral administration, such as tablets, soft or hard gel capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

The pharmaceutical compositions according to the present invention are preferably administered orally.

By way of example, a unit administration form of a compound according to the invention in tablet form may comprise the following components:

| | |
|---|---|
| Compound according to the invention | 50.0 mg |
| Mannitol | 223.75 mg |
| Sodium croscaramellose | 6.0 mg |
| Maize starch | 15.0 mg |
| Hydroxypropylmethylcellulose | 2.25 mg |
| Magnesium stearate | 3.0 mg |

The present invention also relates to a pharmaceutical composition as defined above, as a medicament.

A subject of the present invention is also the use of a compound of formula (I), as defined above, for use thereof in the treatment and prevention of diseases requiring a modulation of FGFs.

A subject of the present invention is also the use of a compound of formula (I), as defined above, for use thereof in the treatment and prevention of cancers, in particular carcinomas which have a high degree of vascularization, such as lung, breast, prostate, pancreatic, colon, kidney and oesophageal carcinomas, cancers which induce metastases, such as colon cancer, liver cancer and stomach cancer, melanomas, gliomas, lymphomas and leukaemias.

A compound of formula (I) according to the present invention can be administered alone or in combination with one or more compound(s) which has (have) an anti-angiogenic activity or with one or more cytotoxic compound(s) (chemotherapy), or else in combination with a radiation treatment. Thus, a subject of the present invention is also the use of a compound of formula (I), as defined above, in combination with one or more anticancer active ingredient(s) and/or with radiotherapy.

A subject of the present invention is also the use of a compound of formula (I), as defined above, in the treatment and prevention of cardiovascular diseases, such as atherosclerosis or post-angioplasty restenosis, diseases related to complications occurring following the implantation of endovascular stents and/or aortocoronary bypasses or other vascular grafts, cardiac hypertrophy, or vascular complications of diabetes, such as diabetic retinopathies.

A subject of the present invention is also the use of a compound of formula (I), as defined above, in the treatment or prevention of chronic inflammatory diseases such as rheumatoid arthritis or IBD.

A subject of the present invention is also the use of a compound of formula (I), as defined above, in the treatment or prevention of osteoarthritis, achondroplasias (ACH), hypochondroplasias (HCH) and TD (thanatophoric dysplasia).

A subject of the present invention is also the use of a compound of formula (I), as defined above, in the treatment or prevention of obesity.

A subject of the present invention is also the use of a compound of formula (I), as defined above, in the treatment or prevention of macular degeneration, such as age-related macular degeneration (ARMD).

The compositions according to the invention, for oral administration, contain recommended doses of 0.01 to 700 mg. There may be particular cases where higher or lower dosages are appropriate; such dosages do not depart from the context of the invention. According to the usual practice, the dosage appropriate for each patient is determined by the physician according to the method of administration and the age, weight and response of the patient, and also according to the degree of progression of the disease.

According to another of its aspects, the present invention also relates to a method for treating the pathological conditions indicated above, which comprises the administration, to a patient, of an effective dose of a compound according to the invention, or a pharmaceutically acceptable salt, hydrate or solvate thereof.

The invention claimed is:
1. A compound of formula (I):

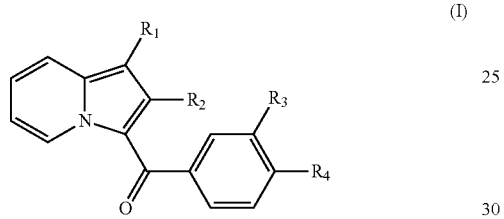

(I)

wherein:
$R_1$ represents
  a hydrogen or halogen atom,
  an alkyl group optionally substituted with —$COOR_5$,
  an alkenyl group optionally substituted with —$COOR_5$,
  a —$COOR_5$ or —$CONR_5R_6$ group,
  an —$NR_5COR_6$ or —$NR_5$—$SO_2R_6$ group,
  an —$OR_5$, —O-Alk-$OR_5$, —O-Alk-$COOR_5$, —O-Alk-$OR_5$, —O-Alk-$NR_5R_6$ or —O-Alk-$NR_7R_8$ group or
  an aryl group, or a heteroaryl group, said aryl or heteroaryl group being optionally substituted with one or more groups selected from: halogen atoms, alkyl groups, cycloalkyl groups, —$COOR_5$, —$CF_3$, —$OCF_3$, —CN, —$C(NH_2)NOH$, —OR $R_5$, —O-Alk-$COOR_5$, —O-Alk-$NR_5R_6$, —O-Alk-$NR_7R_8$, -Alk-$OR_5$, -Alk-$COOR_5$, —$CONR_5R_6$, —CO-$NR_5$—$OR_6$, —CO-$NR_5$—$SO_2R_7$, —$CONR_5$-Alk-$NR_5R_6$, —$CONR_5$-Alk-$NR_7R_8$, -Alk-$NR_5R_6$, —$NR_5R_6$, —$NC(O)N(CH_3)_2$, —CO-Alk, —CO (OAlK)$_n$ OH, —COO-Alk-$NR_5R_6$, —COO-Alk-$NR_7R_8$ and 5-membered heteroaryl groups, said heteroaryl groups being optionally substituted with one or more groups selected from halogen atoms and alkyl, —$CF_3$, —CN, —$COOR_5$, -Alk-$OR_5$, -Alk-$COOR_5$,—$CONR_5R_6$,—$CONR_7R_8$,—CO—$NR_5$— $OR_6$, —CO—$NR_5$—$SO_2R_6$, —$NR_5R_6$ and -Alk-$NR_5R_6$ groups, or with a hydroxyl group or with an oxygen atom,
n is an integer ranging from 1 to 3,
$R_2$ represents:
a hydrogen atom,
an alkyl group,
a phenyl group optionally substituted with one or more alkyl groups,
$R_3$ and $R_4$ together form, with the carbon atoms of the phenyl nucleus to which they are attached, a 6-membered nitrogenous heterocycle corresponding to one of formula (A), (B) or (C) below:

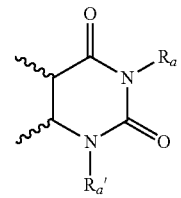

(A)

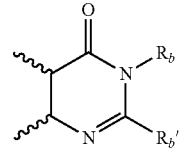

(B)

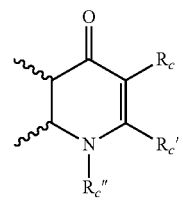

(C)

in which the wavy lines represent the phenyl nucleus to which $R_3$ and $R_4$ are attached and:
$R_a$ represents a hydrogen atom or an alkyl, haloalkyl, -Alk-$CF_3$, -Alk-$COOR_5$, -Alk'$COOR_5$ , -Alk-$CONR_5R_6$, -Alk'-$CONR_5R_6$, -Alk-$CONR_7R_8$, -Alk-$NR_5R_6$, -AlkCONR$_5$R$_6$, Alk-$NR_7R_8$, -Alk-cycloalkyl, -Alk-O-$R_5$, -Alk-S-$R_5$, -Alk-CN, —$OR_5$, —OAlk$COOR_5$, —$NR_5R_6$, —$NR_5$—$COOR_6$, -Alk-aryl, -Alk-O-aryl, -Alk-O-heteroaryl, -Alk-heteroaryl or heteroaryl group, where the aryl or heteroaryl group is optionally substituted with one or more halogen atoms and/or alkyl, cycloalkyl, —$CF_3$, —$OCF_3$, —O—$R_5$ or —S—$R_5$ groups,
$R_{a'}$ represents a hydrogen atom or a linear, branched, cyclic or partially cyclic alkyl group, or an -Alk-$OR_5$, -Alk-$NR_5R_6$ or -Alk-$NR_7R_8$ group, $R_{a'}$ being optionally substituted with one or more halogen atoms,
$R_b$ represents a hydrogen atom or an alkyl or -Alk-$COOR_5$ group,
$R_{b'}$ represents a hydrogen atom or an alkyl, haloalkyl, cycloalkyl, phenyl or -Alk $COOR_5$ group,
$R_c$ represents a hydrogen atom or an alkyl, —CN, —$COOR_5$, —CO—$NR_5R_6$, —$CONR_7R_8$, —CO—$NR_5$-Alk-$NR_5R_6$, —$CONR_5$-Alk-$OR_5$, —$CONR_5SO_2R_5$, -Alk-aryl or -Alk-heteroaryl group, where the aryl or heteroaryl group is optionally substituted with one or more halogen atoms and/or alkyl, cycloalkyl, —$CF_3$, —$OCF_3$, —O-alkyl or —S-alkyl groups,
$R_{c'}$ represents a hydrogen atom or an alkyl group,
$R_{c''}$ represents a hydrogen atom or an alkyl, alkenyl, haloalkyl, cycloalkyl, -Alk-$NR_5R_6$, -Alk-$NR_7R_8$, -Alk-$OR_5$ or -Alk-$SR_5$ group,
$R_5$ and $R_6$, which may be identical or different, represent hydrogen atoms, haloalkyl groups or alkyl groups, cycloalkyl groups or an Ms group,
$R_7$ and $R_8$, which may be identical or different, represent hydrogen atoms or alkyl or phenyl groups, or else $R_7$ and $R_8$ together form a 3- to 8-membered saturated ring which can optionally contain a heteroatom,
Alk represents a linear or branched alkylene chain, and
Alk' represents a linear, branched, cyclic or partially cyclic alkylene chain, optionally in the form of a pharmaceutically acceptable salt thereof.

2. The compound according to claim 1, wherein $R_1$ represents an —$OR_5$, —O-Alk-$OR_5$, —$COOR_5$ or —O-Alk-$COOR_5$ group or a phenyl group optionally substituted with one or more alkyl or —$COOR_5$ groups, in which $R_5$ represents a hydrogen atom or an alkyl group containing from 1 to 4 carbon atoms, and Alk represents an alkylene chain containing 1 or 2 carbon atoms, or a heteroaryl group.

3. The compound according to claim 1, wherein $R_1$ represents an —$OR_5$, —O-Alk-$OR_5$ or —O-Alk-$COOR_5$ group or a phenyl group optionally substituted with one or more alkyl or —$COOR_5$ groups, in which $R_5$ represents a hydrogen atom or a methyl group, and Alk represents an alkylene chain containing 1 or 2 carbon atoms, or a heteroaryl group.

4. The compound of formula (I) according to claim 1, wherein $R_2$ represents an alkyl group containing from 1 to 4 carbon atoms or a phenyl group.

5. The compound of formula (I) according to claim 1, wherein $R_3$ and $R_4$ together form, with the carbon atoms of the phenyl nucleus to which they are attached, a 6-membered nitrogenous heterocycle corresponding to one of formula (A), (B) or (C) defined above and in which:

$R_a$ represents a hydrogen atom or an alkyl or haloalkyl, —$OR_5$, -Alk-$OR_5$, -Alk'-$COOR_5$, —$NR_5R_6$, -Alk-$NR_7R_8$, -Alk-CN, —$NR_5$—$COOR_6$, -Alk'-CO—$NR_5R_6$, -Alk-CO—$NR_5$—$OR_6$ or —O-Alk-$COOR_5$ group, or a heteroaryl, -Alk-heteroaryl or -Alk-aryl group in which the aryl or heteroaryl group is optionally substituted with an alkyl group or a halogen atom, $R_{a'}$ represents a hydrogen atom or an alkyl or -Alk-$OR_5$ group, $R_b$ represents a hydrogen atom or an alkyl or -Alk-$COOR_5$ group, $R_{b'}$ represents a hydrogen atom or an alkyl, haloalkyl or -Alk-$COOR_5$ group, $R_c$ represents a hydrogen atom or an alkyl, —$COOR_5$, CN, —CO—$NR_5R_6$ or —CO—$NR_7R_8$ group, a heteroaryl or an Alk-heteroaryl, $R_{c'}$ represents a hydrogen atom or an alkyl group, $R_{e''}$ represents a hydrogen atom or an alkyl or alkenyl group, said alkyl or alkenyl groups mentioned above contain from 1 to 4 carbon atoms, $R_5$ and $R_6$ represent hydrogen atoms or alkyl or haloalkyl groups, said alkyl and haloalkyl groups containing from 1 to 4 carbon atoms, $R_7$ and $R_8$ represent hydrogen atoms or alkyl groups containing from 1 to 4 carbon atoms, or together form a 5- or 6-membered saturated ring, Alk represents a linear or branched alkylene chain containing from 1 to 4 carbon atoms, and Alk' represents a linear, branched, cyclic or partially cyclic alkylene chain containing from 1 to 4 carbon atoms.

6. The compound according to claim 5, wherein $R_3$ and $R_4$ together form, with the carbon atoms of the phenyl nucleus to which they are attached, a 6-membered nitrogenous heterocycle corresponding to either of formulae (A) and (C).

7. The compound of formula (I) according to claim 5, wherein $R_3$ and $R_4$ together form, with the carbon atoms of the phenyl nucleus to which they are attached, a 6-membered nitrogenous heterocycle corresponding to formula (C).

8. The compound of formula (I) according to claim 1, selected from the following compounds:

2-{6-[(1-methoxy-2-methylindolizin-3-yl)carbonyl]-2,4-dioxo-1,4-dihydroquinazolin-3(2H)-yl}N,N'-dimethylacetamide, 2-{6-[(1-methoxy-2-methylindolizin-3-yl)carbonyl]-1-methyl-2,4-dioxo-1,4-dihydroquinazolin-3(2H)-yl}-N,N'-dimethylacetamide, 6-[(1-methoxy-2-methylindolizin-3-yl)carbonyl]-3-[(3-methyl-1,2,4-oxadiazol-5-yl)methyl]quinazoline-2,4(1H,3H)-dione, 3-{3-(2,4-dioxo-3-propyl-1,2,3,4-tetrahydroquinazolin-6-yl)carbonyl}-2-methylindolizin-1-yl}benzoic acid, {6-[(1-methoxy-2-phenylindolizin-3-yl)carbonyl]-2,4-dioxo-1,4-dihydroquinazolin-3(2H)-yl}-acetic acid, Ethyl ({6-[(1-methoxy-2-methylindolizin-3-yl)carbonyl]-2,4-dioxo-1,4-dihydroquinazolin-3(2H)-yl}oxy)acetate, 3-amino-6-[(1-methoxy-2-methylindolizin-3y1)carbonyl]quinazoline-2,4(1H,3H)-dione, 6-[(1-methoxy-2-methylindolizin-3-yl)carbonyl]-2-methylquinazolin-4(3H)-one, 3-{2-methyl-3-[(2-methyl-4-oxo-3,4-dihydroquinazolin-6-yl)carbonyl]indolizin-1-yl}benzoic acid, 6-{[1(2-methoxyethoxy)-2-methylindolizin-3-yl]carbonyl}-3-propylquinazoline-2,4(1H,3H)-dione, 6-[(1-methoxy-2-methylindolizin-3-yl)carbonyl]-1-methyl-4-oxo-1,4-dihydroquinoline-3-carboxylic acid, 6-[(1-methoxy-2-methylindolizin-3-yl)carbonyl]-2-methyl-4-oxo-1,4-dihydroquinoline-3-carboxylic acid, 6-[(1-methoxy-2-methylindolizin-3-yl)carbonyl]-N-methyl-4-oxo-1,4-dihydroquinoline-3-carboxamide, N-1-dimethyl-6-[(2-methylindolizin-3-yl)carbonyl]-4-oxo-1,4-dihydroquinoline-3-carboxamide, and N-1-dimethyl-6-{[2-methyl-1-(pyridin-4-yl)indolizin-3-yl]carbonyl}-4-oxo-1,4-dihydro-quinoline-3-carboxamide hydrochloride.

9. A process for preparing the compound according to claim 1 wherein $R_3$ and $R_4$ together form, with the carbon atoms of the phenyl nucleus to which they are attached, a 6-membered nitrogenous heterocycle corresponding to formula (A), $R_1$ represents an —$OR_5$, —O Alk-$OR_5$, —$COOR_5$, —O-Alk-$COOR_5$, —O-Alk-$OR_5$, O-Alk-$NR_5R_6$ or —O-Alk-$NR_7R_8$ group, and $R_2$ is as defined in claim 1, comprising:

condensing the compound of formula (II)

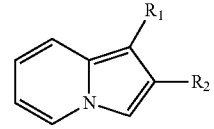

(II)

with the compound of formula (III)

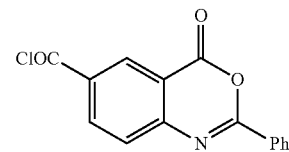

(III)

in order to obtain the compound of formula (IV)

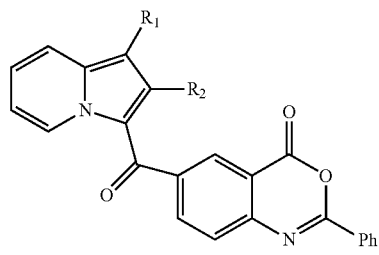

(IV)

subjecting the compound of formula (IV) to a basic hydrolysis reaction in order to obtain the compound of formula (V):

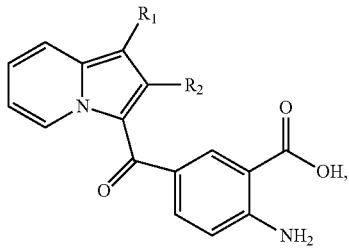

(V)

subjecting the compound formula (V) to an esterification to obtain the compound of formula (VI):

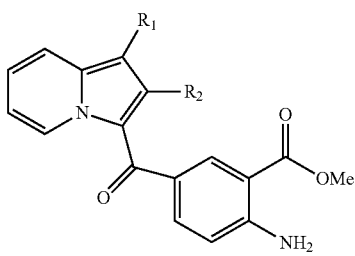

(VI)

subjecting the compound of formula (VI) to the action of triphosgene so as to form the isocyanate corresponding to the compound of formula (VI), and then condensing said isocyanate with an amine of formula $R_aNH_2$, $R_a$ being as defined in claim 1, in order to obtain the urea of formula (VII), (VII)

subjecting the compound of formula (VII) to a cyclization reaction in a basic medium, in order to obtain the compound of formula (VIII):

(VIII)

subjecting the compound of formula (VIII) to an alkylation reaction in the presence of a base and of a halogenated derivative Ra'X, Ra' being as defined in claim 1 and X being a halogen.

10. A process for preparing the compound according to claim 1 wherein $R_3$ and $R_4$ together form a nitrogenous heterocycle of formula (A) and in which $R_1$ is as defined in claim 1, with the proviso that $R_1$ does not represent one of the following groups: —$OR_5$, —O Alk-$OR_5$, —$COOR_5$, —O-Alk-$COOR_5$, —O-Alk-$OR_5$, O-Alk-$NR_5R_6$ and —O-Alk-$NR_7R_8$, $R_2$ being as defined in claim 1, comprising:

condensing the compound of formula (IX)

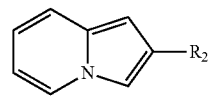

(IX)

with the compound of formula (III)

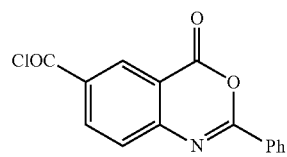

(III)

in order to obtain the compound of formula (X)

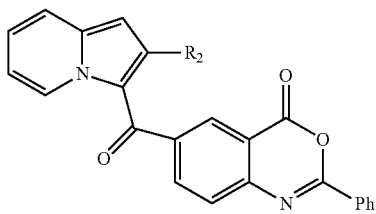

(X)

subjecting the compound of formula (X) to a basic hydrolysis reaction in order to obtain the compound of formula (XI):

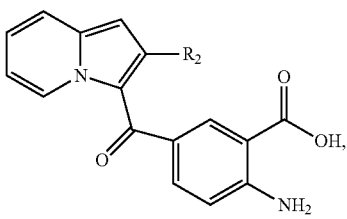

(XI)

subjecting the compound of formula (XI) to an esterification to obtain the compound of formula (XII):

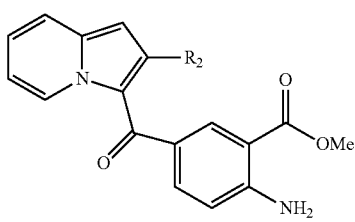

(XII)

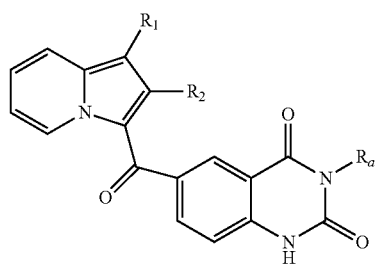

reacting the compound of formula (XII) with N-bromosuccinimide to obtain the compound of formula (XIII):

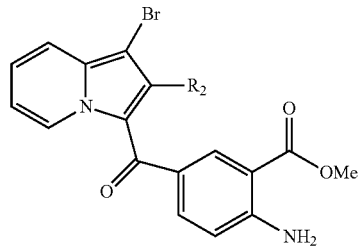

subjecting the compound of formula (XIII) to the action of triphosgene to form_the isocyanate corresponding to the compound of formula (XIII), and condensing with an amine of formula $R_a\cdot_{NH2}R_a$ being as defined in claim 1, in order to obtain the urea of formula (XIV):

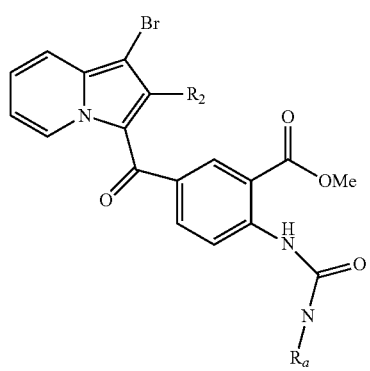

subjecting the compound of formula (XIV) to a cyclization reaction in a basic medium in order to obtain the compound of formula (XV):

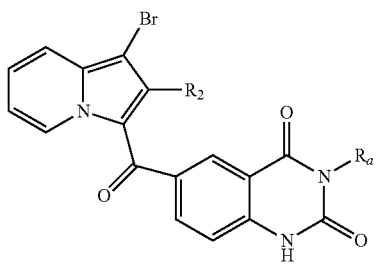

subjecting the compound of formula (XV), in the presence of a palladium catalyst, of a ligand and of a base:
  to a reaction with phenylboronic or heteroarylboronic or phenylboronate ester or heteroarylboronate ester derivatives according to a Suzuki coupling,
  or else to a cyanation reaction with zinc cyanide, followed by an acid hydrolysis, in order to obtain the compound of formula (XVI):

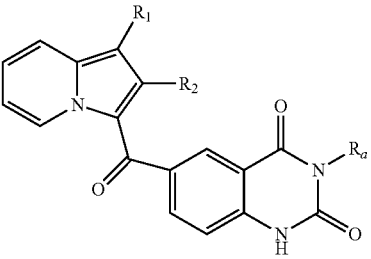

subjecting the compound of formula (XVI) to an alkylation reaction in the presence of a base and of a halogenated derivative Ra'X, Ra' being as defined in claim 1 and X being a halogen.

11. A process for preparing the compound according to claim 1, wherein $R_3$ and $R_4$ together form a nitrogenous heterocycle of formula (C), in which $R_1$ represents an $OR_5$, —O-Alk-$OR_5$, —$COOR_5$, —O-Alk-$COOR_5$, —O-Alk-$OR_5$, O-Alk-$NR_5R_6$ or —O-Alk-$NR_7R_8$ group, and $R_5$, $R_6$ and $R_2$ are as defined in claim 1, comprising:

condensing the compound of formula (II):

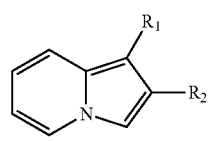

with the compound of formula (III):

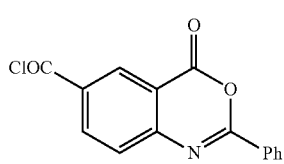

in order to obtain the compound of formula (IV):

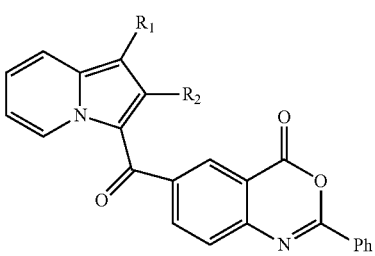

subjecting the compound of formula (IV) to a basic hydrolysis reaction in order to obtain the compound of formula (V):

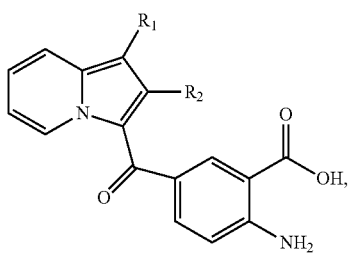

(V)

subjecting the compound (V) to a condensation reaction in order to obtain the compound (XXI):

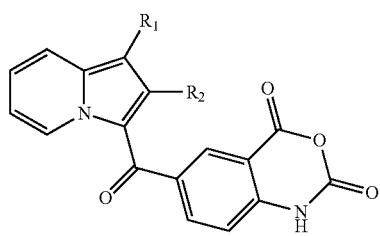

(XXI)

subjecting the compound (XXI) to an alkylation reaction in the presence of a base and of a halogenated derivative Rc"X, Rc" being as defined in claim 1 and X being a halogen, or of a protective group, to obtain the compound of formula (XXII):

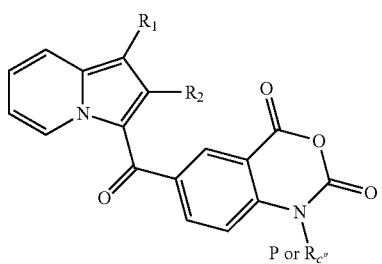

(XXII)

subjecting the compound (XXII) to a condensation reaction with a malonic derivative in order to obtain the compound of formula (XXIII):

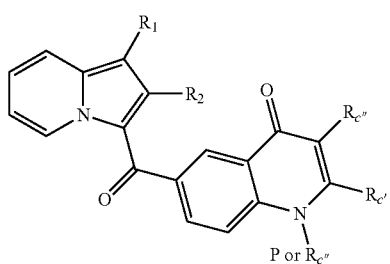

(XXIII)

in which Rc' and Rc are defined in claim 1, subjecting the compound of formula (XXIII) to a deprotection reaction.

12. A process for preparing the compound according to claim 1, wherein $R_3$ and $R_4$ together form a nitrogenous heterocycle of formula (C), $R_1$ represents an aryl or heteroaryl group, optionally substituted with one or more alkyl, —$OR_5$, $NR_5R_6$ or —$COOR_5$ groups, Rc' represents an alkyl, Rc" $R_5$, $R_6$ and $R_2$ being defined in claim 1, comprising:

condensing the compound of formula (IX):

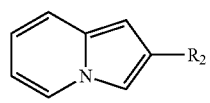

(IX)

with the compound of formula (III):

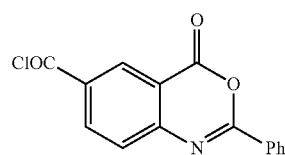

(III)

in order to obtain the compound of formula (X):

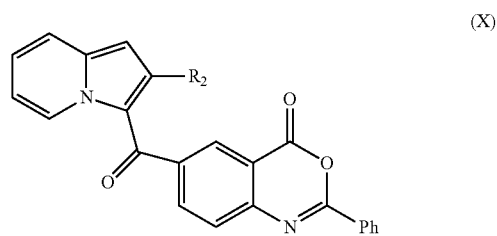

(X)

subjecting the compound of formula (X) to a basic hydrolysis reaction in order to obtain the compound of formula (XI):

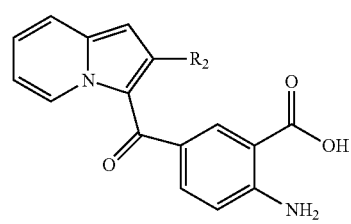

(XI)

subjecting the compound of formula (XI) to an esterification to obtain the compound of formula (XII):

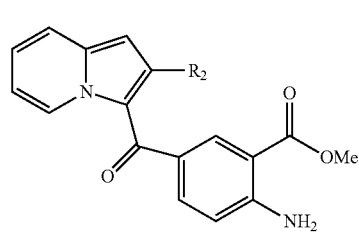

(XII)

reacting the compound of formula (XII) with N-bromosuccinimide to obtain the compound of formula (XIII):

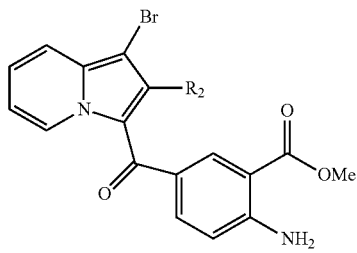
(XIII)

subjecting the compound of formula (XIII) to a saponification reaction in a basic medium in order to obtain the compound XVIII:

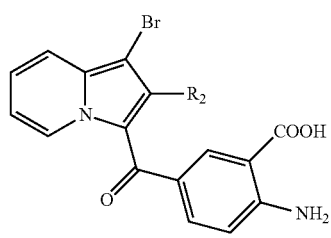
(XVIII)

subjecting the compound (XVIII) to a condensation reaction in order to obtain the compound (XXIV):

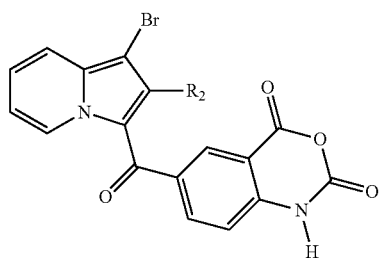
(XXIV)

subjecting the compound of formula (XXIV) to an alkylation reaction in the presence of a base and of a halogenated derivative $R_c"X$, $R_c"$ being as defined in claim 1 and X being a halogen, or of a protective group, in order to obtain the compound of formula (XXV):

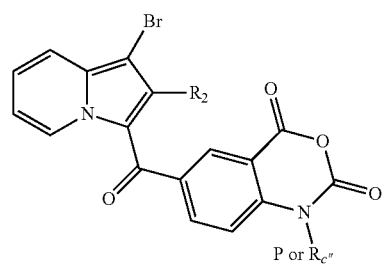
(XXV)

subjecting the compound of formula (XXV) to a condensation reaction with a malonic derivative in order to obtain the compound of formula (XXVI):

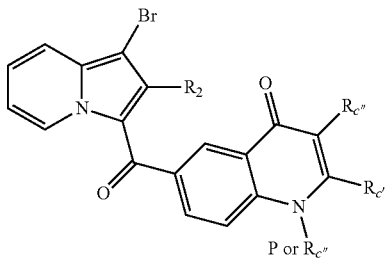
(XXVI)

in which $R_c'$ and $R_c$ are as defined in claim 1, subjecting the compound of formula (XXVI), in the presence of a palladium catalyst, of a ligand and of a base, to a reaction with phenylboronic or heteroarylboronic or phenylboronate ester or heteroarylboronate ester derivatives according to a Suzuki coupling, in order to obtain the compound of formula (XXVII):

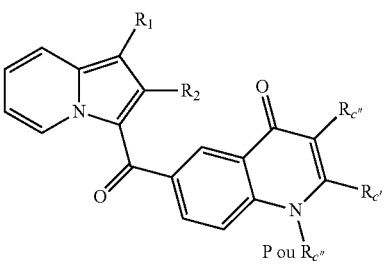
(XXVII)

subjecting the compound of formula (XXVII) to a deprotection reaction.

13. A process for preparing the compound according to claim 1, wherein $R_3$ and $R_4$ together form a nitrogenous heterocycle of formula (C), where Rc' represents a hydrogen, Rc and Rc" being as defined in claim 1, and $R_1$ represents hydrogen or an —$OR_5$, —O -Alk-$OR_5$, —$COOR_5$, —O-Alk-$COOR_5$, —O-Alk-$OR_5$, O-Alk-$NR_5R_6$ or —O-Alk-$NR_7R_8$ group being as defined in claim 1, comprising:

condensing the compound of formula (II):

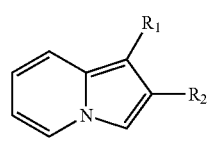
(II)

with 4-nitrobenzoic acid chloride to obtain the compound of formula (XXVIII):

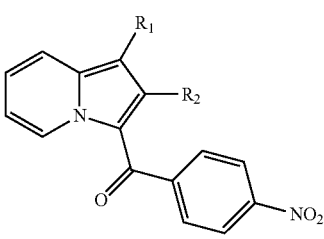
(XXVIII)

subjecting the compound of formula (XXVIII) to a reaction in the presence of iron and of acetic acid to obtain the compound of formula (XXIX):

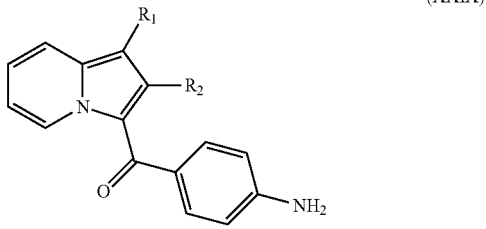
(XXIX)

subjecting the compound of formula (XXIX) to a condensation reduction to obtain the compound of formula (XXX):

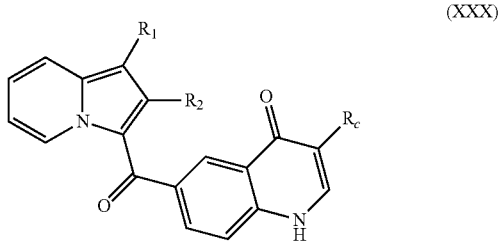
(XXX)

subjecting the compound of formula (XXX) to an alkylation reaction in the presence of a halide Rc"X, Rc" being as defined in claim 1 and X being a halogen, and in the presence of a base.

14. A pharmaceutical composition containing, as an active ingredient, a compound of formula (I) according to claim 1, optionally in combination with one or more suitable inert excipients.

15. A method of treating cancer in a patient in need thereof comprising administering to said patient a therapeutically effective amount of the pharmaceutical composition of claim 14.

16. The method according to claim 15, further comprising administering said pharmaceutical composition in combination with one or more anticancer active ingredient(s) and/or with radiotherapy and/or with any anti-VEGF treatment.

17. A method of treating cardiovascular diseases, diseases related to complications that occur following the implantation of endovascular stents and/or aortocoronary bypasses or other vascular grafts, cardiac hypertrophy, vascular complications of diabetes, liver, kidney and lung fibroses, neuropathic pain, chronic inflammatory diseases, prostatic hyperplasia, psoriasis, clear cell acanthoma, osteoarthritis, achondroplasias (ACH), hypochondroplasias (HCH), TD (thanatophoric dysplasia), obesity, and macular degeneration, in a patient in need thereof comprising administering to said patient a therapeutically amount of the pharmaceutical composition of claim 14.

18. The compound according to claim 1, wherein said aryl group is phenyl.

19. The compound according to claim 3, wherein said heteroaryl group is a pyridinyl group.

20. The method according to claim 15, wherein said cancer is selected from carcinomas which have a high degree of vascularization, cancers selected from metastases, melanomas, gliomas, lymphomas, leukaemias and thrombopenias.

21. The method according to claim 18 wherein the cardiovascular diseases is selected from atherosclerosis and post-angioplasty restenosis.

22. The method according to claim 17 wherein the vascular complications of diabetes is selected from diabetic retinopathies.

23. The method according to claim 17 wherein the chronic inflammatory diseases is selected from rheumatoid arthritis and inflammatory bowel disease (IBD).

24. The method according to claim 17 wherein the macular degeneration is age related macular degeneration (ARMD).

* * * * *